US009181552B2

(12) United States Patent
Lorenzi et al.

(10) Patent No.: US 9,181,552 B2
(45) Date of Patent: Nov. 10, 2015

(54) MATERIALS AND METHODS DIRECTED TO ASPARAGINE SYNTHETASE AND ASPARAGINASE THERAPIES

(75) Inventors: Philip L. Lorenzi, Washington, DC (US); John N. Weinstein, Chevy Chase, MD (US); Natasha J. Caplen, Silver Spring, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 544 days.

(21) Appl. No.: 13/151,420

(22) Filed: Jun. 2, 2011

(65) Prior Publication Data

US 2011/0229984 A1    Sep. 22, 2011

Related U.S. Application Data

(62) Division of application No. 12/281,589, filed as application No. PCT/US2007/005555 on Mar. 2, 2007, now Pat. No. 7,985,548.

(60) Provisional application No. 60/779,143, filed on Mar. 3, 2006, provisional application No. 60/833,027, filed on Jul. 25, 2006.

(51) Int. Cl.
*C12N 1/00* (2006.01)
*C12N 15/113* (2010.01)
*C12N 15/11* (2006.01)
*C12Q 1/68* (2006.01)

(52) U.S. Cl.
CPC .......... *C12N 15/1137* (2013.01); *C12N 15/111* (2013.01); *C12Q 1/6886* (2013.01); *C12N 2310/14* (2013.01); *C12N 2320/31* (2013.01); *C12Q 2600/106* (2013.01)

(58) Field of Classification Search
CPC .......................... C12N 2009/00; C12Q 1/6886
See application file for complete search history.

(56) References Cited

U.S. PATENT DOCUMENTS

| | | | |
|---|---|---|---|
| 4,450,150 A | 5/1984 | Sidman | |
| 5,169,939 A | 12/1992 | Gefter et al. | |
| 5,530,101 A * | 6/1996 | Queen et al. | 530/387.3 |
| 5,643,759 A | 7/1997 | Pfreundschuh | |
| 5,750,078 A | 5/1998 | Shitara et al. | |
| 6,020,153 A | 2/2000 | Hardman et al. | |
| 6,420,113 B1 | 7/2002 | Buechler et al. | |
| 6,423,511 B1 | 7/2002 | Nakamura et al. | |
| 6,632,927 B2 | 10/2003 | Adair et al. | |
| 6,800,738 B1 | 10/2004 | Carter et al. | |
| 7,700,293 B2 * | 4/2010 | Chinnaiyan | 435/6.14 |

FOREIGN PATENT DOCUMENTS

WO    WO 2006/095270 A1    9/2006

OTHER PUBLICATIONS

Weinstein (Disease Markers 17: 77-88, 2001).*
Aagaard et al., "A Facile Lentiviral Vector System for Expression of Doxycycline-Inducible shRNAs: Knockdown of the Pre-miRNA Processing Enzyme Drosha," Epub, 1-8, Feb. 20, 2007; *Molecular Therapy*, 15, 938-945 (2007).
Alley et al., "Feasibility of Drug Screening with Panels of Human Tumor Cell Lines Using a Microculture Tetrazolium Assay," *Cancer Res.*, 48, 589-601 (1988).
Ando et al., "Selective apoptosis of natural killer-cell tumours by 1-asparaginase," *Br. J Haematol.*, 130 (6), 860-868 (2005).
Appel et al., "Up-regulation of asparagine synthetase expression is not linked to the clinical response L-asparaginase in pediatric acute lymphoblastic leukemia," *Blood*, 107 (11), 4244-4249 (2006).
Aslanian et al., "Asparagine synthetase expression alone is sufficient to induce 1-asparaginase resistance in MOLT-4 human leukaemia cells," *Biochem. J.*, 357, 321-328 (2001).
Aslanian et al., "Multiple adaptive mechanisms affect asparagine synthetase substrate availability in asparaginase-resistant MOLT-4 human leukaemia cells," *Biochem. J.*, 358, 59-67 (2001).
Batist et al., "Overexpression of a Novel Anionic Glutathione Transferase in Multidrug-resistant Human Breast Cancer Cells," *J. Biol. Chem.*, 261 (33), 15544-15549 (1986).
Boehlein et al., "Characterization of Inhibitors Acting at the Synthetase Site of *Escherichia coli* Asparagine Synthetase B," *Biochemistry*, 40,11168-11175 (2001).
Bolhuis et al., "T cell targeting in cancer therapy," *Cancer Immunol. Immunother.*, 34, 1-8 (1991).
Bussey et al., "Integrating data on DNA copy number with gene expression levels and drug sensitivities in the NCI-60 cell line panel," *Mol. Cancer Ther.*, 5 (4), 853-867 (2006).
Capizzi et al., "Sequential high-dose ara-C and asparaginase versus high-dose ara-C alone in the treatment of patients with relapsed and refractory acute leukemias," *Semin. Oncol.*, 14 (2 Suppl 1), 40-50 (1987).
Carter et al., "Toward the Production of Bispecific Antibody Fragments for Clinical Applications," *J. Hematotherapy*, 4, 463-470 (1995).
Ciustea et al., "Efficient expression, purification, and characterization of C-terminally tagged, recombinant human asparagine synthetase," *Arch. Biochem. Biophys.*, 440 (1),18-27 (2005).
Cowan et al., "Similar biochemical changes associated with multidrug resistance in human breast cancer cells and carcinogen-induced resistance to xenobiotics in rats," *Proc. Natl. Acad. Sci. USA*, 83, 9328-9332 (1986).
Ding et al., "Epigenetic changes in the repression and induction of asparagines synthetase in human leukemic cell lines," *Leukemia*, 19, 420-426 (2005).
Engels et al., "Gene Synthesis," *Angew. Chem. Int. Ed. Engl.*, 28, 716-734 (1989).
Entrez Gene ID No. 440, Aug. 28, 2008.

(Continued)

*Primary Examiner* — Alana Harris Dent
(74) *Attorney, Agent, or Firm* — Leydig, Voit & Mayer

(57) ABSTRACT

Materials and Methods for use in treating cell proliferative disorders related to asparagine metabolism are provided. Cell proliferative disorders include such cancers as forms of leukemia, ovarian cancers, melanomas, renal cancers, breast cancers, brain cancers, and other cancers. Methods include the use of RNA interference targeted at asparagine synthetase to enhance the efficacy of L-asparaginase therapies.

13 Claims, 15 Drawing Sheets

(56) References Cited

OTHER PUBLICATIONS

Fine et al., "A Genome-Wide View of the In-vitro Response to L-Asparaginase in Acute Lymphoblastic Leukemia," *Cancer Res.*, 65 (1), 291-299 (2005).
Gantt et al., "Elevated levels of asparagine synthetase activity in physiologically and genetically derepressed Chinese hamster ovary cells are due to increased rates of enzyme synthesis," *J. Biol. Chem.*, 256 (14), 7311-7315 (1981).
GenBank Accession No. AAA36781, Aug. 3, 1993.
GenBank Accession No. M15798, Aug. 3, 1993.
GenBank Accession No. AAA51789, Oct. 31, 1994.
GenBank Accession No. M27396, Oct. 31, 1994.
GenBank Accession No. AAA52756, Nov. 9, 1994.
GenBank Accession No. L35946, Nov. 9, 1994.
GenBank Accession No. M27054, Mar. 7, 1995.
GenBank Accession No. AAA63266, Mar. 9, 1995.
GenBank Accession No. BG718826, updated May 8, 2001.
GenBank Accession No. AAP35777, May 13, 2003.
GenBank Accession No. BT007113, May 13, 2003.
GenBank Accession No. AAQ96856, Oct. 15, 2003.
GenBank Accession No. AC079781, Oct. 15, 2003.
GenBank Accession No. CH236949, Aug. 10, 2004.
GenBank Accession No. EAL24115, Aug. 10, 2004.
GenBank Accession No. AAH08723, Jul. 15, 2006.
GenBank Accession No. AAH14621, Jul. 15, 2006.
GenBank Accession No. BC008723, Jul. 15, 2006.
GenBank Accession No. BC014621, Jul. 15, 2006.
GenBank Accession No. BC030024, Aug. 4, 2006.
GenBank Accession No. AK000379, Sep. 12, 2006.
GenBank Accession No. NM_001673, Feb. 21, 2008.
GenBank Accession No. NM_133436, Feb. 21, 2008.
GenBank Accession No. NM_183356, Feb. 21, 2008.
GenBank Accession No. NP_001664, Feb. 21, 2008.
GenBank Accession No. NP_597680, Feb. 21, 2008.
GenBank Accession No. NP_899199, Feb. 21, 2008.
Gutierrez et al., "An Inhibitor of Human Asparagine Synthetase Suppresses Proliferation of an L-Asparaginase-Resistant Leukemia Cell Line," *Chemistry and Biology*, 13, 1339-1347 (2006).
Hak et al., "Asparaginase pharmacodynamics differ by formulation among children with newly diagnosed acute lymphoblastic leukemia," *Leukemia*, 18, 1072-1077 (2004).
International Search Report PCT/US2007/005555.
Karlin et al., "Methods for assessing the statistical significance of molecular sequence features by using general scoring schemes," *Proc. Natl. Acad. Sci. USA*, 87, 2264-2268 (1990).
Karlin et al., "Applications and statistics for multiple high-scoring segments in molecular sequences," *Proc. Natl. Acad. Sci. USA*, 90, 5873-5877 (1993).
Keating et al., "L-asparaginase and PEG asparaginase—past, present, and future," *Leuk. Lymphoma.*, 10 Suppl., 153-157 (1993)—Abstract Only.
Kononen et al., "Tissue microarrays for high-throughput molecular profiling of tumor specimens." *Nat. Med.*, 4 (7), 844-847 (1998).
Koroniak et al., "Synthesis and Characterization of an N-Acylsulfonamide Inhibitor of Human Asparagine Synthetase," *Organic Letters*, 5 (12), 2033-2036 (2003).
Krejci et al., "Upregulation of asparagines synthetase fails to avert cell cycle arrest induced by L-asparaginase in TEL/AML1-positive leukaemic cells," *Leukemia*, 18, 434-441 (2004).
Leslie et al., "Expression levels of asparagine synthetase in blasts from children and adults with acute lymphoblastic leukaemia," *Br. J. Haematol.*, 132 (6), 740-742 (2006).
Lorenzi et al., "Asparagine synthetase is a predictive biomarker of L-asparaginase activity in ovarian cancer cell lines," *Mol. Cancer Ther.*, 7 (10), 3123-3128 (2008).
Lorenzi et al., "Asparagine synthetase as a biomarker for L-asparaginase activity in ovarian cancer," *97th AACR Annual Meeting*, Abstract 3122 (2006).
Lorenzi et al., "Asparagine synthetase is a predictive biomarker of L-asparaginase activity in ovarian cancer cell lines," *Mol. Cancer Ther.*, 5 (11), 2613-2623 (2006).
Ludwig, "Biomarkers in Cancer Staging, Prognosis and Treatment Selection," *Nat. Rev. Cancer*, 5, 845-856 (2005).
Maul et al., "Methotrexate stimulation of asparagine synthetase activity in rat liver," *Life Sci.*, 30 (12), 1051-1057 (1982).
Nandy et al., "The synergism of 6-mercaptopurine plus cytosine arabinoside followed by PEG-asparaginase in human leukemia cell lines (CCRF/CEM/0 and (CCRF/CEM/ara-C/7A) is due to increased cellular apoptosis," *Anticancer Res.*, 18 (2A), 727-737 (1998).
Omim, "Human Complement for Hamster Temperature Sensitive Mutant ts11," No. 108370 (1986).
Pluckthun et al., "New protein engineering approaches to multivalent and bispecific antibody fragments," *Immunotechnology*, 3, 83-105 (1997).
Renner et al., "Tumor Therapy by Immune Recruitment with bispecific Antibodies," *Immunological Rev.*, 145, 179-209 (1995).
Richards et al., Asparagine Synthetase Chemotherapy, Annu. Rev. Biochem., 75, 629-654 (2006).
Ross et al., "Systematic variation in gene expression patterns in human cancer cell lines," *Nat. Genet.*, 24, 227-235 (2000).
Rotoli et al., "Inhibition of glutamine synthetase triggers apoptosis in asparaginase-resistant cells," *Cell Physiol Biochem.*, 15, 281-292 (2005).
Sakamoto et al., "Temporary effective treatment with L-asparaginase for a patient with refractory nasal NK/T-cell lymphoma," Gan to Kagaku Ryoho 32(12):1993-6 (2005)—Abstract Only.
Scherf et al., "A gene expression database for the molecular pharmacology of cancer," *Nat. Genet.*, 24, 236-244 (2000).
Segal et al., "Targeting of Anti-Tumor Responses with Bispecific Antibodies," *Immunobiology*, 185, 390-402 (1992).
Segal et al., "Alternative Triggering Molecules and Single Chain Bispecific Antibodies," *J. Hematotherapy*, 4, 377-382 (1995).
Siu et al., "CCAAT/enhancer-binding protein-beta is a mediator of the nutrient-sensing response pathway that activates the human asparagine synthetase gene," *J. Biol. Chem.*, 276, 48100-48107 (2001).
Stams et al., "Asparagine synthetase expression is linked with L-asparaginase resistance in TEL-AML1-negative but not TEL-AML1-positive pediatric acute lymphoblastic leukemia," *Blood*, 105, 4223-4225 (2005).
Stams et al., "Sensitivity to L-asparaginase is not associated with expression levels of asparagine synthetase in t(12;21)+ pediatric ALL," *Blood*, 101, 2743-2747 (2003).
Staunton et al., "Chemosensitivity prediction by transcriptional profiling," *Proc. Natl. Acad. Sci. USA*, 98, 10787-10792 (2001).
Teicher, "Assays for In Vitro and In Vivo Synergy," *Methods in Molecular Medicine*, 85, 297-321 (2003).
Uren et al., "Effects of asparagine synthetase inhibitors on asparaginase resistant tumors," *Biochem. Pharmacol.*, 26 (15), 1405-1410 (1977).
Worton et al., "Hypomethylation and reactivation of the asparagine synthetase gene induced by L-asparaginase and ethyl methanesulfonate," *Cancer Res.*, 51 (3), 985-989 (1991).
Ando et al., "Selective apoptosis of natural killer-cell tumours by l-asparaginase," *Br. J. Haematol.*, 130 (6), 860-868 (Sep. 2005).
Chan et al., "The glutaminase activity of L-asparaginase is not required for anticancer activity against ASNS-negative cells," *Blood*, 123 (23), 3596-3606 (2014).
Hutson et al., "Amino acid control of asparagine synthetase: relation to asparaginase resistance in human leukemia cells," *Am. J. Physiol.*, 272 (5 pt. 1), C1691-C1699 (May 1997).
Lorenzi et al., "Development of a robust nanoimmunoassay and immunohistochemical assay for asparagine synthetase," *103rd AACR Annual Meeting*, Apr. 1, 2012 (published abstract).

(56) References Cited

OTHER PUBLICATIONS

Lorenzi et al., "Development of a robust nanoimmunoassay and immunohistochemical assay for asparagine synthetase," *103rd AACR Annual Meeting*, Apr. 1, 2012 (poster) 4 pgs.
Lorenzi et al., "DNA fingerprinting of the NCI-60 cell line panel," *Mol. Cancer Ther.*, 8 (4), 713-724 (Apr. 2009).
Malla et al., "Limitations in doxorubicin production from *Streptomyces peucetius*," *Microbiol. Res.*, 165 (5), 427-435 (Jul. 2010).
Sheng et al., "High-Level Expression of Human Asparagine Synthetase and Production of Monoclonal Antibodies for Enzyme Purification," *Protein Expr. Purif.*, 3 (4), 337-346 (Aug. 1992).

* cited by examiner

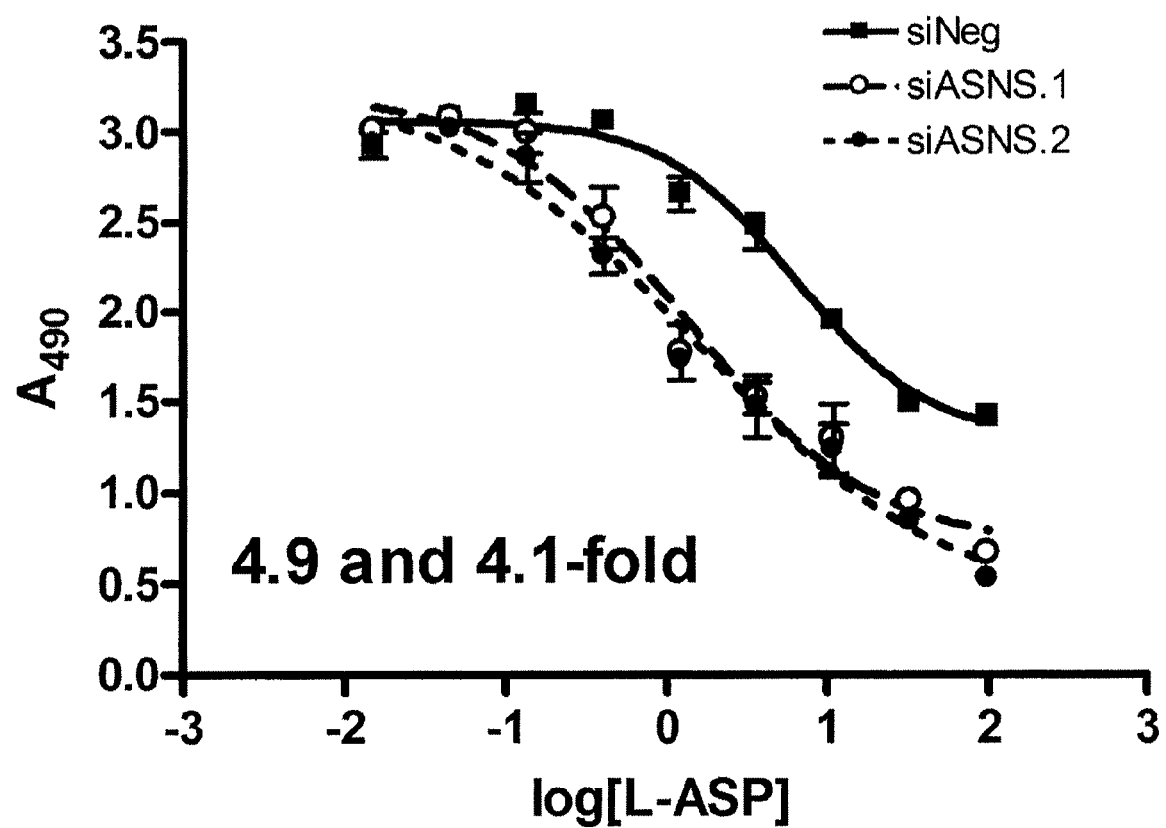

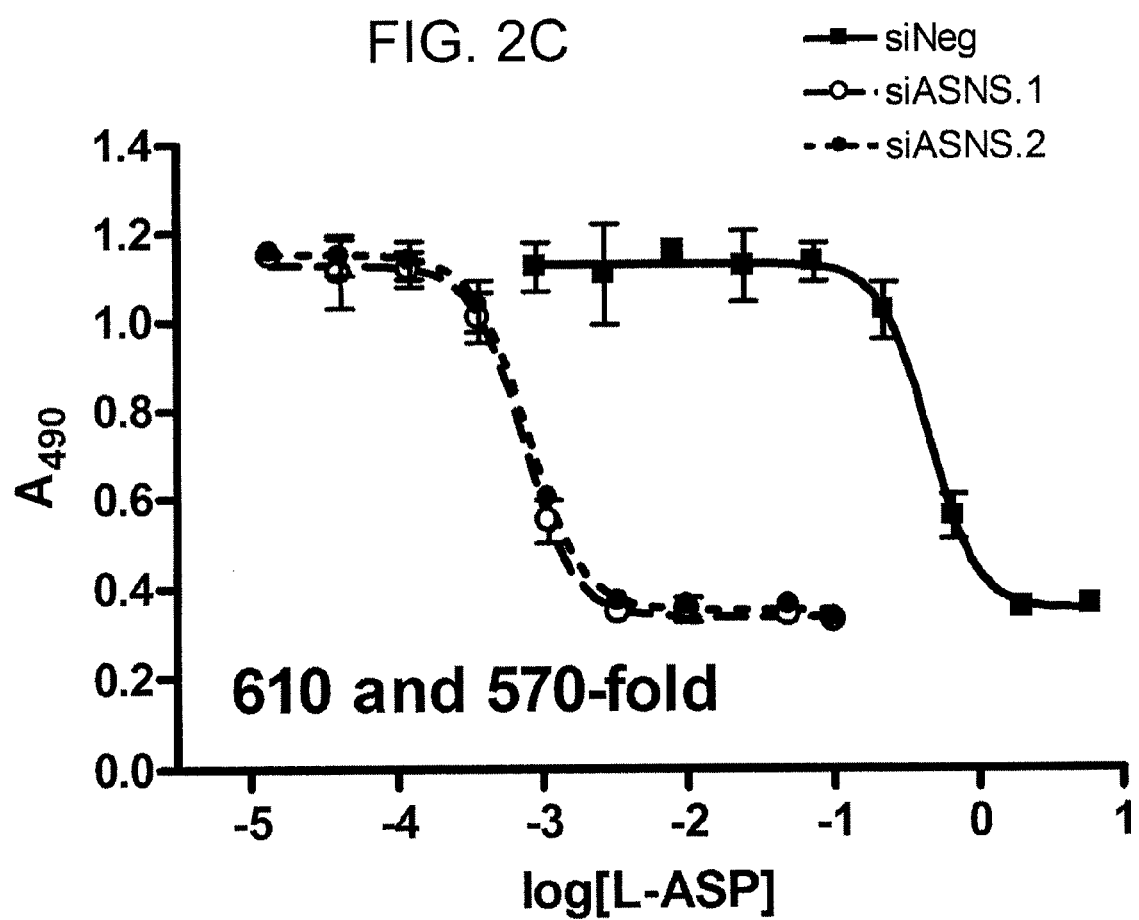

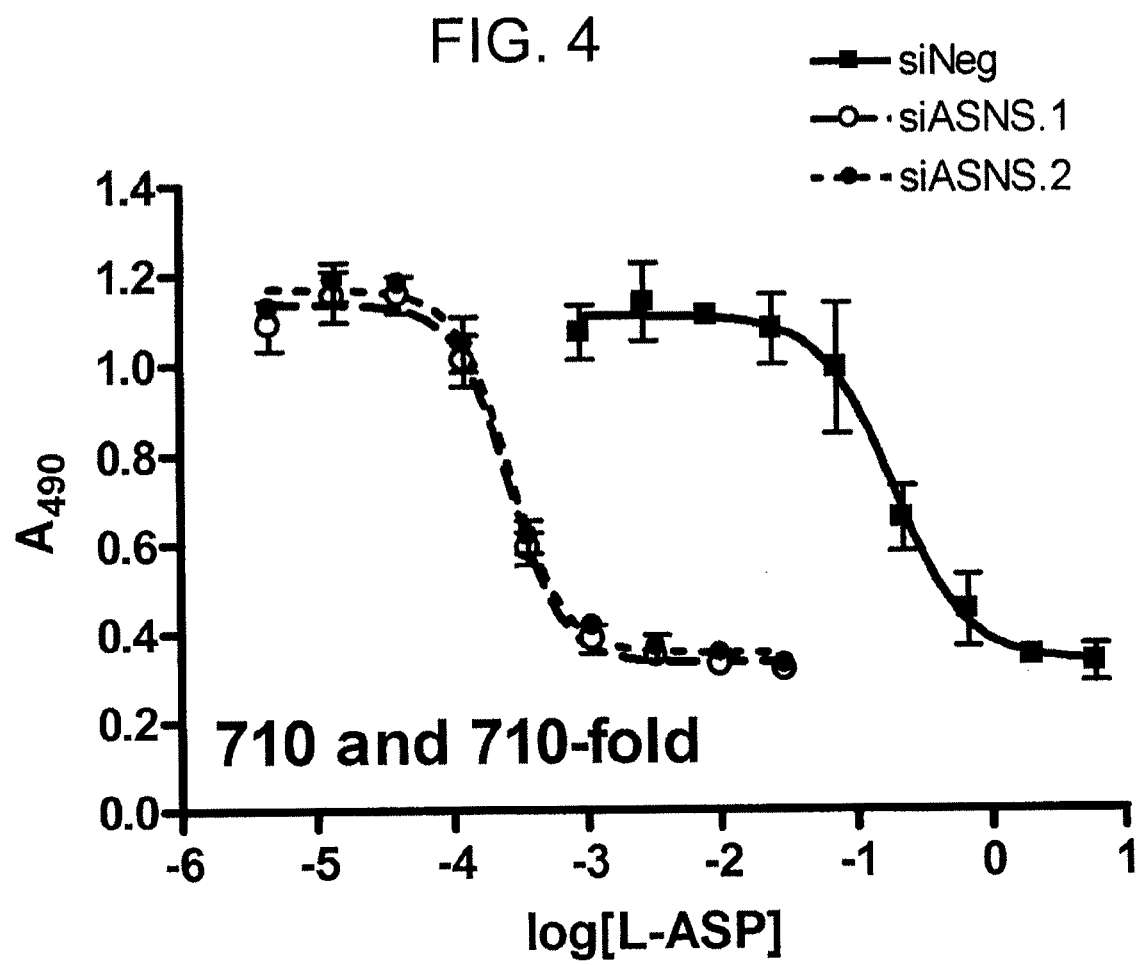

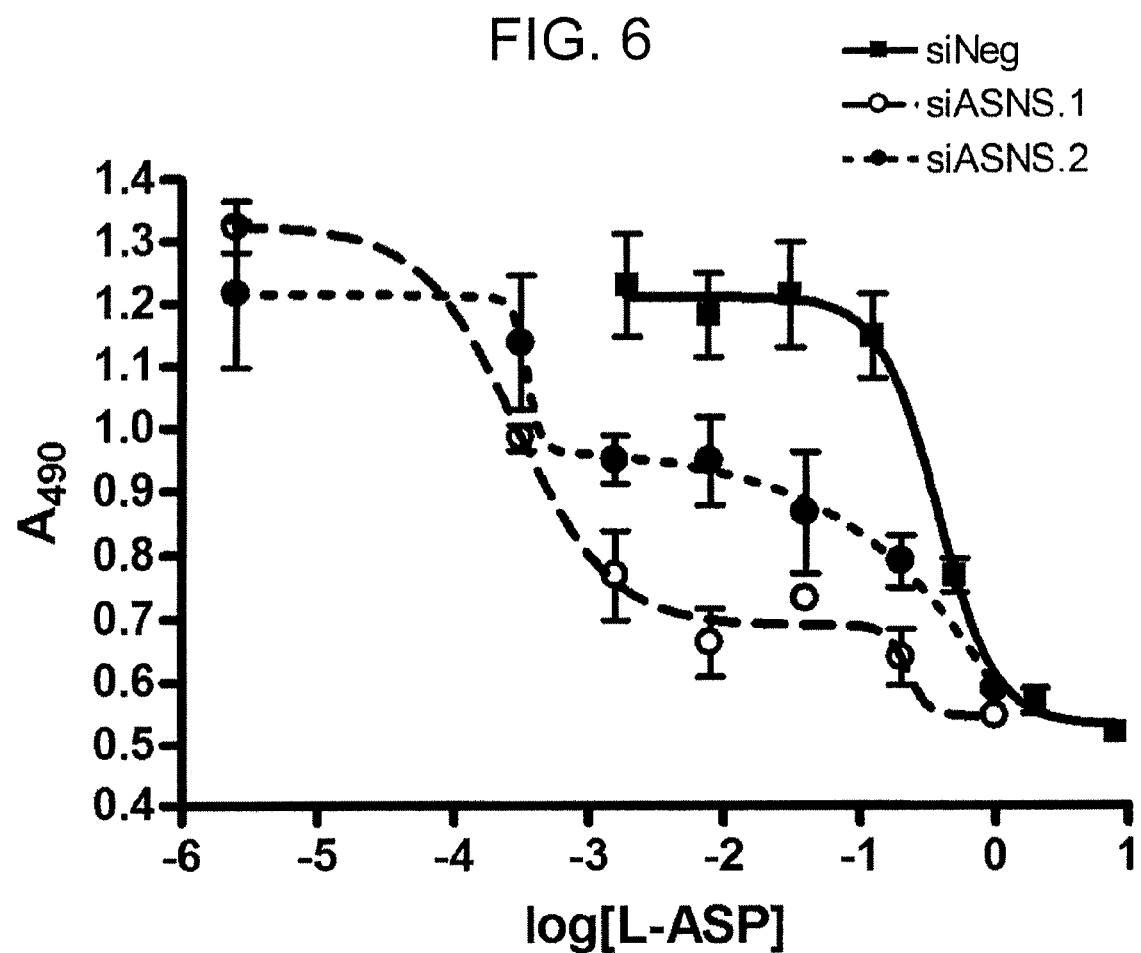

MATERIALS AND METHODS DIRECTED TO ASPARAGINE SYNTHETASE AND ASPARAGINASE THERAPIES

CROSS-REFERENCE TO RELATED APPLICATIONS

This patent application is a Divisional of U.S. patent application Ser. No. 12/281,589, filed Oct. 30, 2008, which is a U.S. National Phase of International Patent Application No. PCT/US07/05555, filed Mar. 2, 2007, which claims the benefit of U.S. Provisional Patent Application Nos. 60/779,143, filed Mar. 3, 2006, and 60/833,027, filed Jul. 25, 2006, the disclosures of which are herein incorporated by reference.

SEQUENCE LISTING

Incorporated by reference in its entirety herein is a computer-readable nucleotide/amino acid sequence listing submitted concurrently herewith and identified as follows: One 26,355 Byte ASCII (Text) file named "708084ST25.txt," created on May 2, 2011.

BACKGROUND OF THE INVENTION

Asparagine is a naturally occurring amino acid that is found in many proteins. Asparagine synthetase (ASNS) is involved in asparagine biosynthesis. L-asparaginase (L-ASP) is an enzyme that catabolizes asparagine. L-ASP has been used in the treatment of acute lymphoblastic leukemia (ALL). There is a desire to improve the efficacy of L-ASP and also to assess the efficacy of L-ASP in treating other forms of cancer. Accordingly, there exists a desire for improved therapies that can replace, complement, enhance, and make better use of existing L-ASP therapies.

BRIEF SUMMARY OF THE INVENTION

The present invention provides a method of decreasing cell proliferation, e.g., cancer, in a subject in need thereof, the method comprising administering to the subject an asparagine synthetase (ASNS) antagonist and at least one of a L-asparaginase (L-ASP) and a pegylated L-ASP thereby resulting in a greater decrease in cell proliferation in the subject than with the administration of the ASNS antagonist, L-ASP, or pegylated L-ASP alone. The ASNS antagonist and at least one of a L-asparaginase (L-ASP) and a pegylated L-ASP can be administered in synergistic amounts. The administration of the ASNS antagonist and at least one of a L-asparaginase (L-ASP) and a pegylated L-ASP can be simultaneous, sequential, or in combination. In some embodiments, the ASNS antagonist comprises an ASNS mRNA antagonist. Accordingly, the invention includes a method of decreasing cell proliferation in a subject in need thereof. The method can comprise administering to the subject synergistic amounts of an asparagine synthetase (ASNS) mRNA antagonist and at least one of a L-ASP and a pegylated L-ASP thereby resulting in a greater decrease in undesirable cell proliferation in the subject than with the administration of the ASNS mRNA antagonist, L-ASP, or pegylated L-ASP alone. In some embodiments, the ASNS mRNA antagonist is a small interfering (si)RNA.

The invention includes methods of decreasing expression of ASNS using nucleic acids targeted to one or more allele of an ASNS gene or mRNA encoded by the same. According to an aspect of the invention, a method of decreasing expression of asparagine synthetase (ASNS) in a subject in need thereof is provided. This method comprises introducing into a cell of a subject an effective amount of a therapeutic nucleic acid of at least 10 nucleotides in length that specifically binds to and is complementary to a target nucleic acid encoding ASNS, wherein the introduction of the therapeutic nucleic acid results in a decrease in the expression of a gene encoding ASNS. In another aspect of the invention, a method for interfering with expression of asparagine synthetase (ASNS) is provided. This method comprises introducing into a cell of a subject in need of ASNS inhibition, wherein the cell is capable of expressing ASNS, an effective amount of a small interfering RNA (siRNA) nucleic acid for a time and under conditions sufficient to interfere with expression of the ASNS. Expression can comprise transcription and/or translation.

A method of screening for the efficacy of L-ASP in a subject is provided. The method comprises detecting and identifying steps. A level of expression of an ASNS gene is detected in a sample from the subject, wherein the level is associated with an efficacy of L-asparaginase in decreasing cell proliferation. The efficacy is identified based on the level of expression. The L-ASP can be pegylated.

The invention provides compositions, kits and, uses of manufacturing a medicament. A composition is provided comprising an ASNS antagonist and at least one of a L-asparaginase (L-ASP) and a pegylated L-ASP. A kit is provided comprising an ASNS antagonist and at least one of a L-ASP and a pegylated L-ASP. A kit is also provided comprising a probe for detecting a level of expression of the ASNS gene in a sample from a subject, wherein the level is associated with an efficacy of at least one of a L-ASP and a pegylated L-ASP in decreasing cell proliferation and the efficacy is identified based on the level of expression. Use of an ASNS antagonist and at least one of a L-ASP and a pegylated L-ASP to manufacture a medicament for treatment of undesirable cell proliferation is provided. In some embodiments, a use comprises the use of a nucleic acid that interferes with the expression of ASNS to manufacture a medicament for treatment of undesirable cell proliferation.

BRIEF DESCRIPTION OF THE SEVERAL VIEWS OF THE DRAWING(S)

Figure 2B:
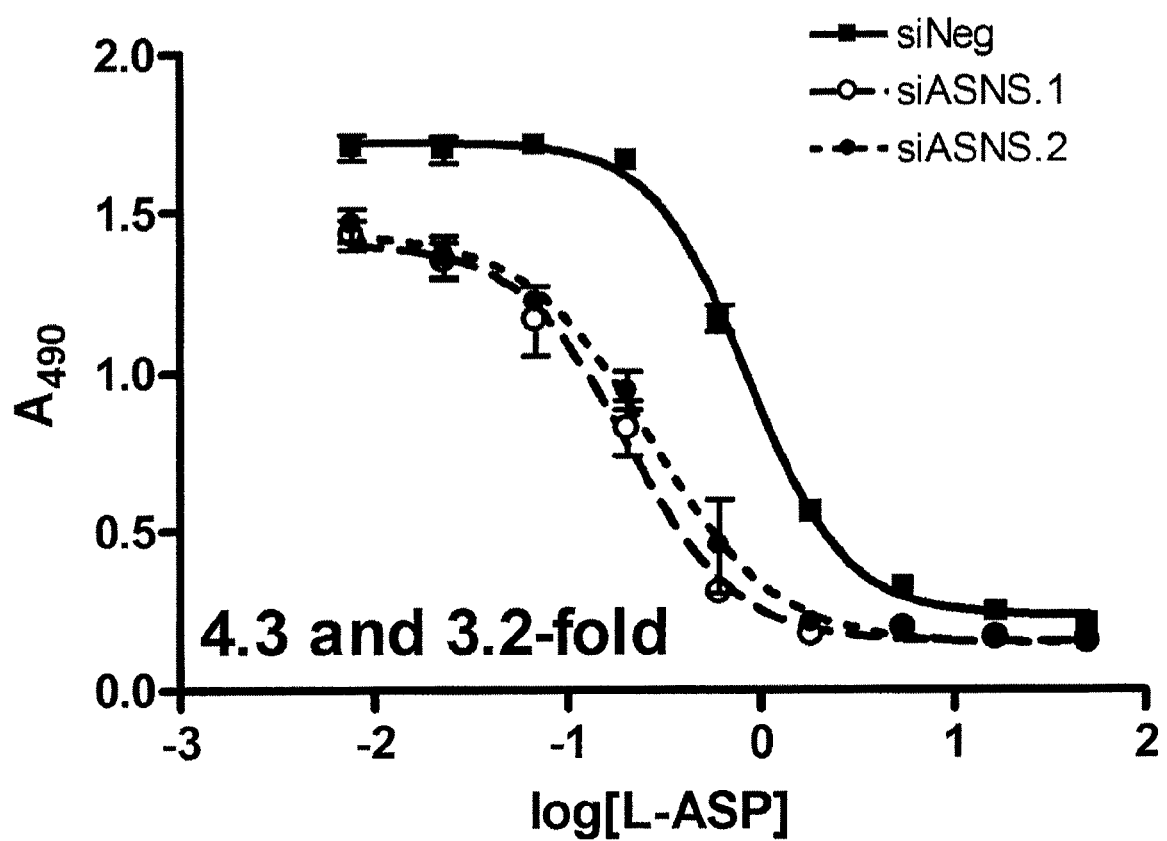

FIG. 2A depicts the synergistically enhanced inhibitory effect of L-ASP on OVCAR-4 cell proliferation in siASNS-transfected cells relative to siNeg-transfected cells. Cells are seeded with siRNA, the medium replaced with fresh medium containing drug at day 3, and MTS assay is performed three days later. Representative single experiments are shown. For FIGS. 2A, 2B, 2C, 3, 4, 5, and 6, the x-axis is log base 10 transformation of drug concentration, and the y-axis is absorbance at 490 nm wavelength to measure the formazan product of the MTS reaction.

FIG. 2B depicts the synergistically enhanced inhibitory effect of L-ASP on OVCAR-3 cell proliferation in siASNS-transfected cells relative to siNeg-transfected cells. Cells are seeded with siRNA, the medium is replaced with fresh medium containing drug at day 2, and MTS assay is performed two days later. Representative single experiments are shown.

FIG. 2C depicts the synergistically enhanced inhibitory effect of L-ASP on OVCAR-8 cell proliferation in siASNS-transfected cells relative to siNeg-transfected cells. Cells are seeded with siRNA, the medium is replaced with fresh medium containing drug at day 2, and MTS assay is performed two days later. Representative single experiments are shown.

Figure 3:
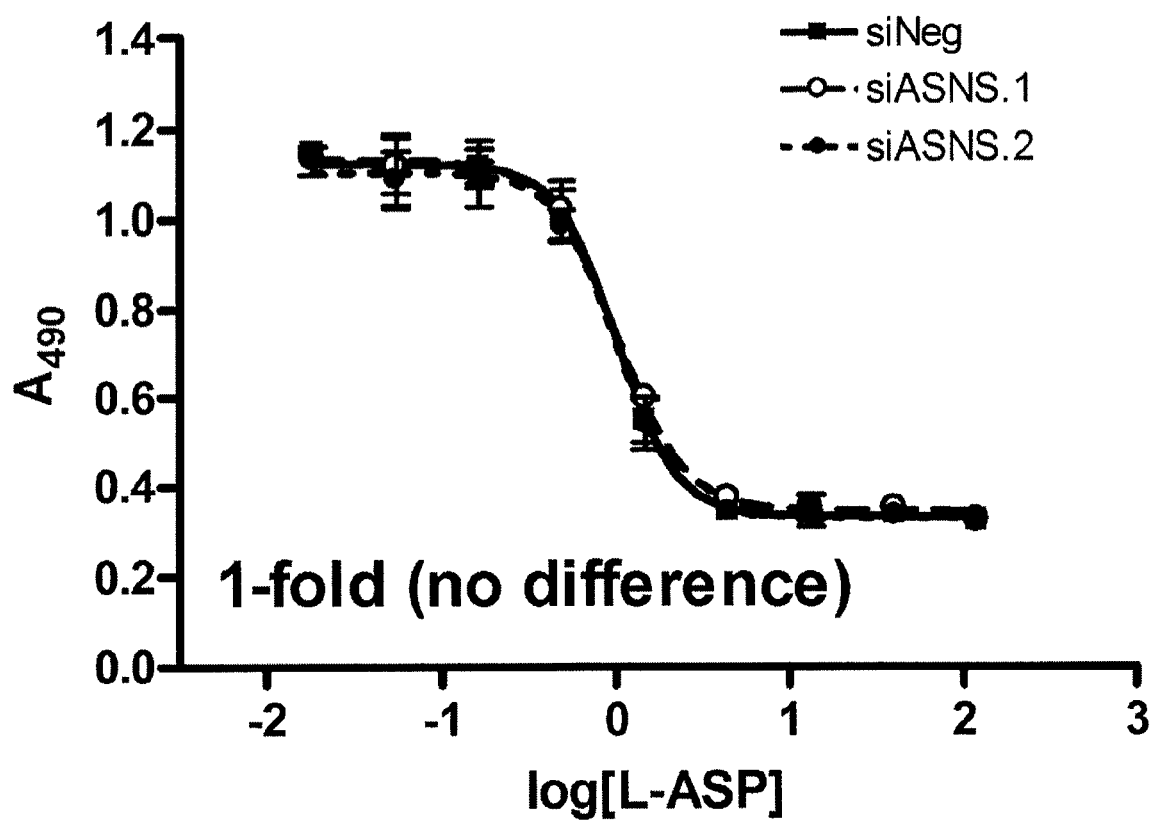

FIG. 3 depicts the effect of L-ASP on cell proliferation in siNeg-transfected and siASNS-transfected ovarian cell lines following termination of siASNS treatment. Cells are seeded with siRNA, the medium is replaced with fresh medium containing drug at day 8, and MTS assay is performed two days later. Representative single experiments are shown.

FIG. 4 depicts the synergistically enhanced inhibitory effect of L-ASP on OVCAR-8/ADR (NCI-ADR-RES) cell proliferation in siASNS-transfected cells relative to siNeg-transfected cells. Experimental conditions are substantially the same as those for OVCAR-8 cells. A representative single experiment is shown.

Figure 5A:
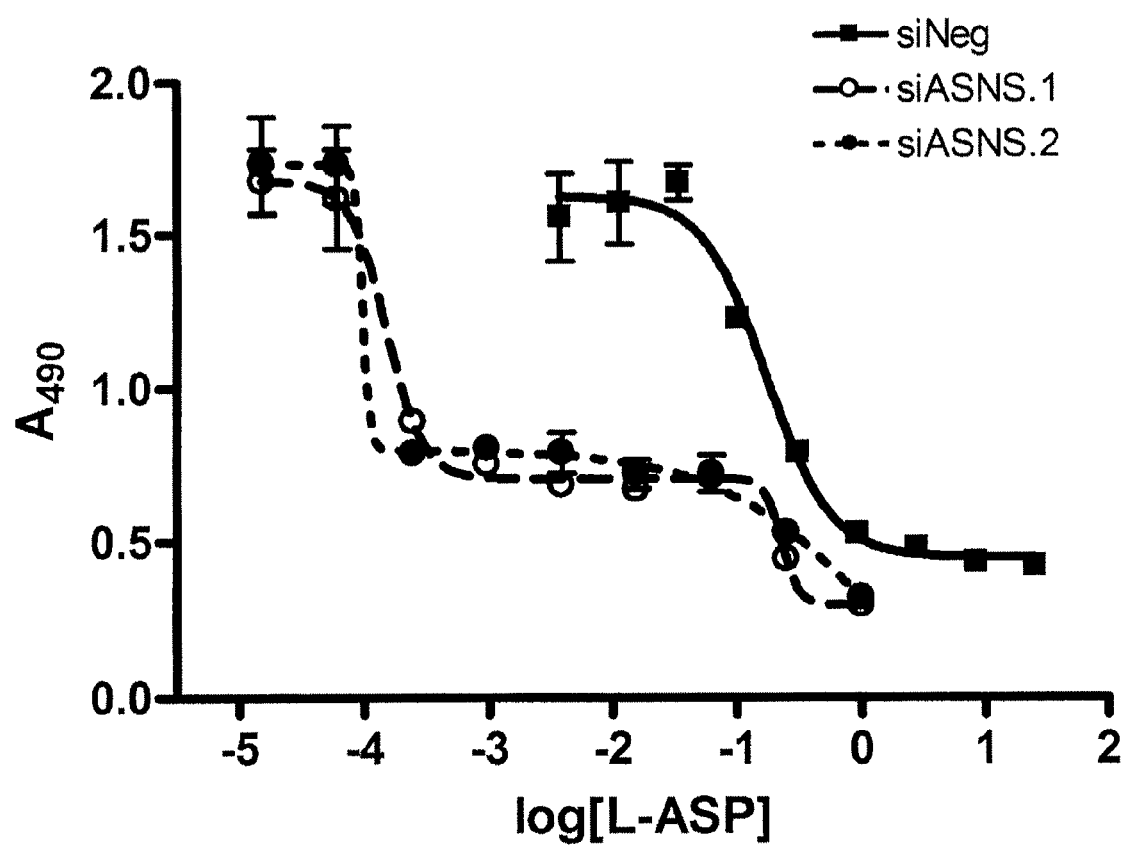
Figure 5B:
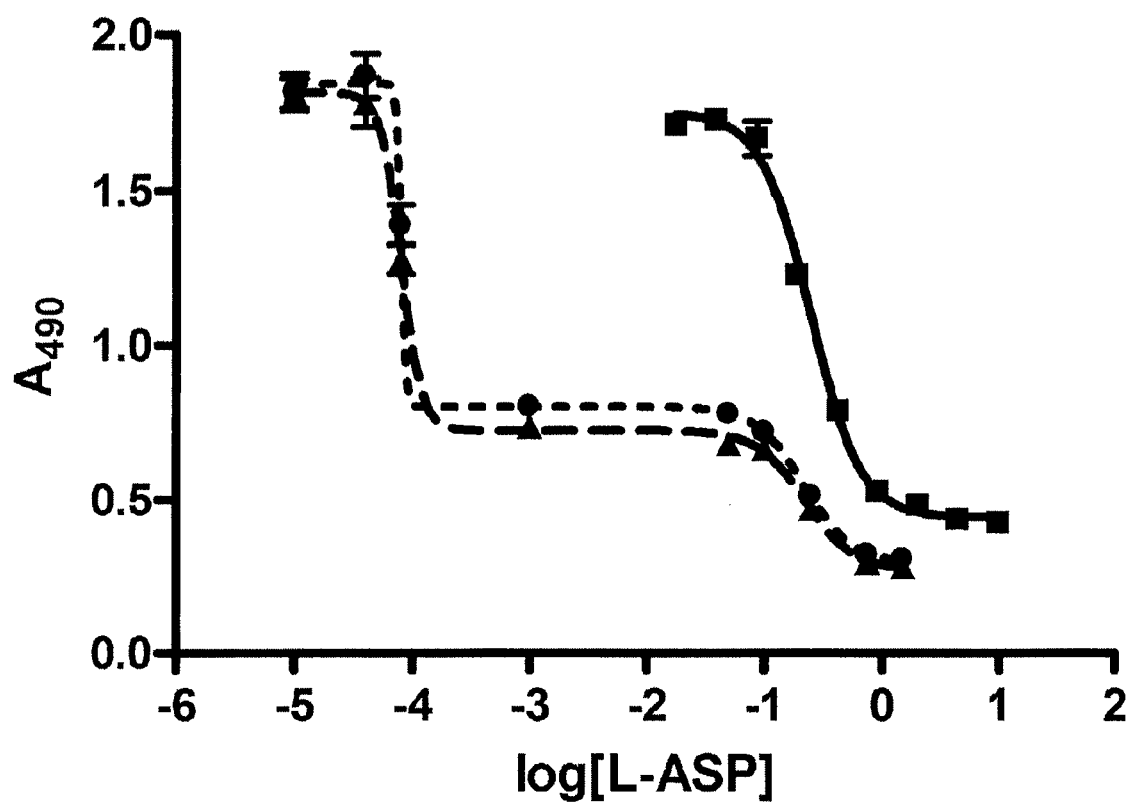

FIGS. 5A and 5B depict the synergistically enhanced inhibitory effect of L-ASP on UACC-257 cell proliferation in siASNS-transfected cells relative to siNeg-transfected cells.

FIG. 6 depicts the synergistically enhanced inhibitory effect of L-ASP on SN12C cell proliferation in siASNS-transfected cells relative to siNeg-transfected cells.

Figure 7:
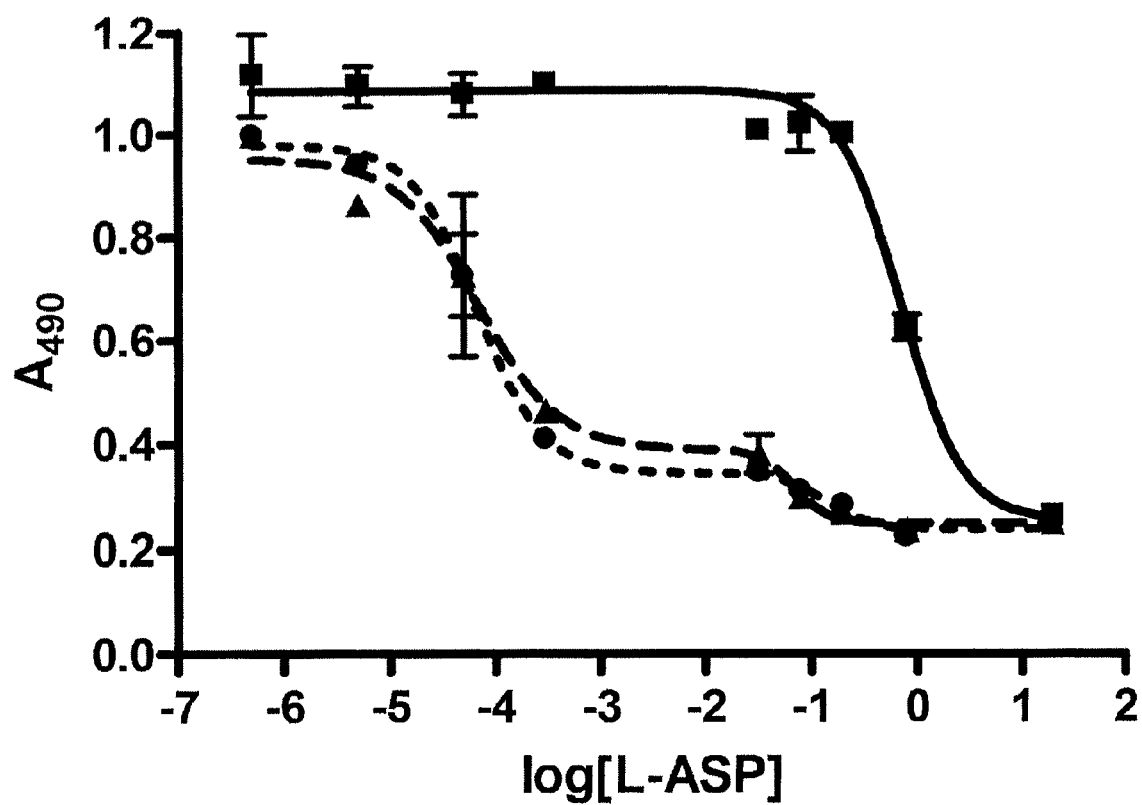

FIG. 7 depicts the synergistically enhanced inhibitory effect of L-ASP on MCF7 cell proliferation in siASNS-transfected cells relative to siNeg-transfected cells. The data shown is from a MTS assay of MCF7 cells transfected with siNeg (squares), siASNS.1 (triangles), or siASNS.2 (circles), incubated at 37° C. for 48 hours, then treated with a range of L-ASP concentrations for 48 hours, immediately followed by the MTS assay.

Figure 8:
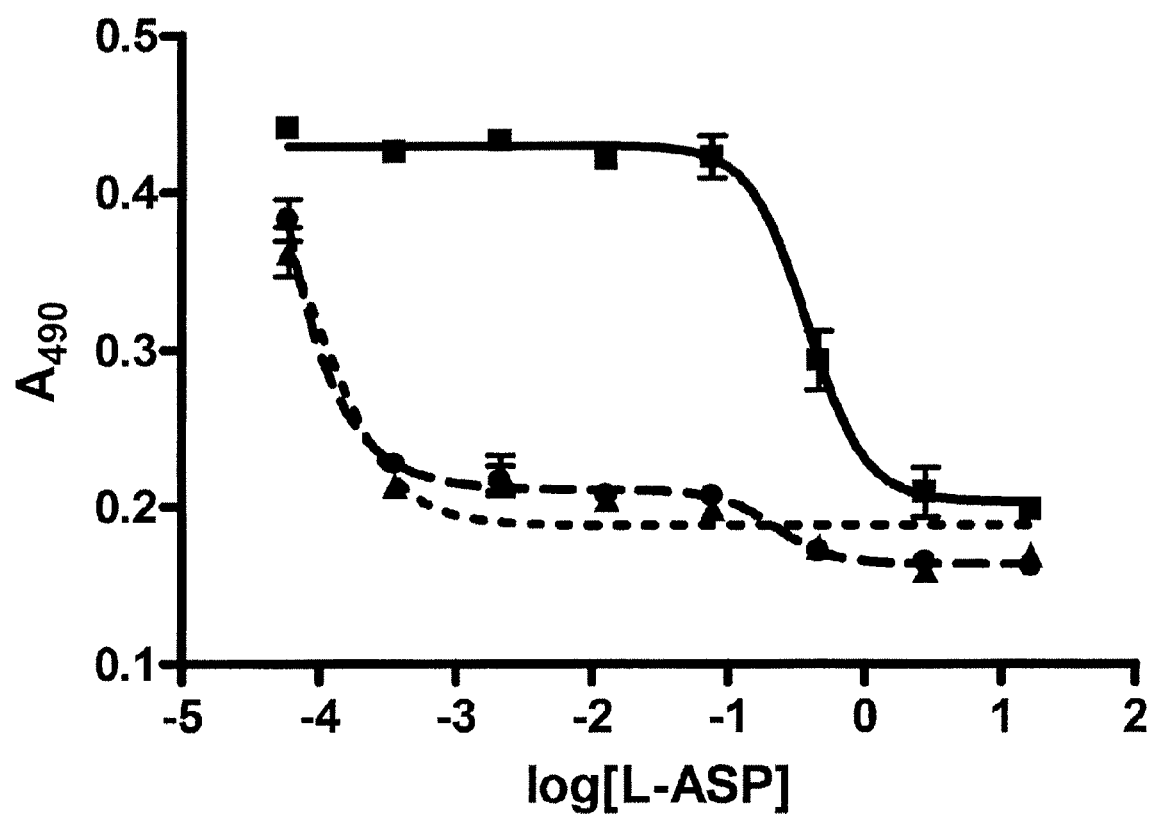

FIG. 8 depicts the synergistically enhanced inhibitory effect of L-ASP on MDA-MB-231 cell proliferation in siASNS-transfected cells relative to siNeg-transfected cells. The data shown is from a MTS assay of MDA-MB-231 cells transfected with siNeg (squares), siASNS.1 (triangles), or siASNS.2 (circles), incubated at 37° C. for 48 hours, then treated with a range of L-ASP concentrations for 48 hours, immediately followed by the MTS assay.

Figure 9:
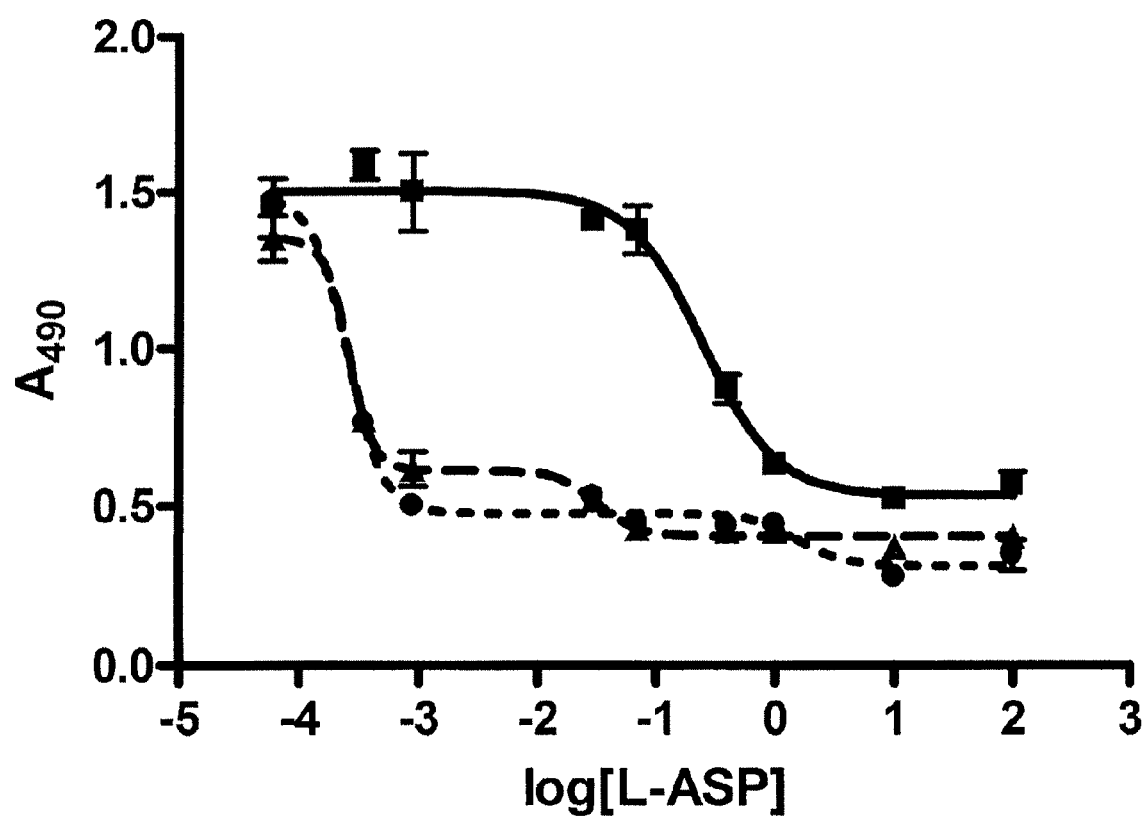

FIG. 9 depicts the synergistically enhanced inhibitory effect of L-ASP on SNB19 cell proliferation in siASNS-transfected cells relative to siNeg-transfected cells. The data shown is from a MTS assay of SNB19 cells transfected with siNeg (squares), siASNS.1 (triangles), or siASNS.2 (circles), incubated at 37° C. for 48 hours, then treated with a range of L-ASP concentrations for 48 hours, immediately followed by the MTS assay.

Figure 10:
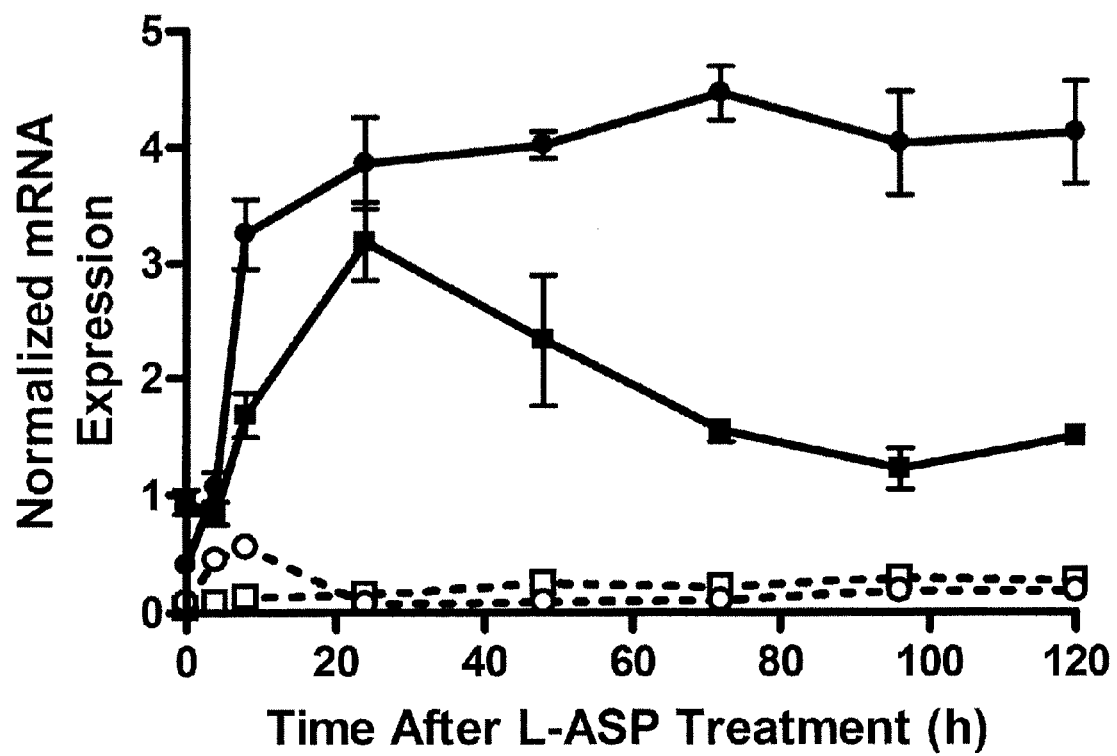

FIG. 10 depicts the time course of ASNS upregulation in response to L-ASP administration. An $EC_{50}$ dose, as described in Table 4, of L-ASP is administered to OVCAR-4 (squares) or OVCAR-8 (circles) cells transfected with either siNeg (shaded) or siASNS.1 (open), and the resulting ASNS mRNA is measured at indicated time points by branched-DNA assay. ASNS level for a given sample (n=2) is normalized to PPIB level of that sample.

DETAILED DESCRIPTION OF THE INVENTION

A method of decreasing cell proliferation in a subject in need thereof is provided, the method comprising administering to the subject an asparagine synthetase (ASNS) antagonist and at least one of a L-asparaginase (L-ASP) and a pegylated L-ASP thereby resulting in a greater decrease in cell proliferation in the subject than with the administration of the ASNS antagonist, the L-ASP, or pegylated L-ASP alone. The administration of the ASNS antagonist and at least one of a L-ASP and a pegylated L-ASP can be simultaneous, sequential or in combination. Accordingly, when both an ASNS antagonist and at least one of a L-ASP and a pegylated L-ASP are administered, they need not be administered simultaneously or in the same way or in the same dose. When administered simultaneously, the ASNS antagonist and at least one of a L-ASP and a pegylated L-ASP can be administered in the same composition or in different compositions. The ASNS antagonist and at least one of a L-ASP and a pegylated L-ASP can be administered using the same route of administration or different routes of administration. When administered at different times, the ASNS antagonist can be administered before or after the at least one of a L-ASP and a pegylated L-ASP. In some embodiments, administration of the ASNS antagonist and at least one of a L-ASP and a pegylated L-ASP is alternated. In some embodiments, the respective doses of ASNS antagonist and at least one of a L-ASP and a pegylated L-ASP are varied over time. The type of L-ASP can be varied over time. The type of ASNS antagonist can be varied over time. When administered at separate times, the separation of the ASNS antagonist administration and the L-ASP administration can be any time period. If administered multiple times, the length of the time period can vary. The separation between administration of ASNS antagonist and L-ASP or between L-ASP and ASNS antagonist can be 0 seconds, 1 second, 5 seconds, 10 seconds, 30 seconds, 1 minute, 5 minutes, 10 minutes, 15 minutes, 20 minutes, 30, minutes, 45 minutes, 1 hour, 1.5 hours, 2 hours, 2.5 hours, 3 hours, 4 hours, 5 hours, 7.5 hours, 10 hours, 12 hours, 15 hours, 18 hours, 21 hours, 24 hours, 1.5 days, 2 days, 3 days, 4 days, 5 days, 6 days, 7 days, 10 days, 2 weeks, 3 weeks, 4 weeks, one month, 6 weeks, 8 weeks, two months, three months, four months, five months, six months, 9 months, 1 year, 2 years, 5, years, 10 years, and any intermediate time period of the preceding.

In some embodiments, the effect on decreasing cell proliferation of administering both the ASNS antagonist and the at least one of a L-ASP and a pegylated L-ASP is less than additive. In some embodiments, the effect is substantially additive. However, the ASNS antagonist preferably potentiates the efficacy of the at least one of a L-ASP and a pegylated L-ASP in decreasing cell proliferation. In some embodiments, the at least one of a L-ASP and a pegylated L-ASP potentiates the efficacy of the ASNS antagonist in decreasing cell proliferation.

The ASNS antagonist and at least one of a L-ASP and a pegylated L-ASP can be administered in synergistic amounts. Accordingly, the administration of both the ASNS antagonist and at least one of a L-ASP and a pegylated L-ASP can have a synergistic effect on the decrease in cell proliferation whether administered simultaneously, sequentially, or in combination. In some embodiments, the ASNS antagonist increases the efficacy of the at least one of a L-ASP and a pegylated L-ASP greater than if the L-ASP or pegylated L-ASP were employed alone. In some embodiments, the amount that the at least one of a L-ASP and a pegylated L-ASP increases the efficacy of the ASNS antagonist is greater than if the ASNS antagonist were employed alone. The effect of administering both an ASNS inhibitor and at least one of a L-ASP and a pegylated L-ASP can be such that the effect on decreasing cell proliferation is greater than the additive effect of each being administered alone. When given in synergistic amounts, the ASNS antagonist can enhance the efficacy of the at least one of a L-ASP and a pegylated L-ASP on decreasing cell proliferation even if the amount of ASNS antagonist employed alone, without any L-ASP or pegylated L-ASP, would have no substantial effect on cell proliferation. Measurements and calculations of synergism can be performed as described in Teicher, "Assays for In Vitro and In Vivo Synergy," in Methods in Molecular Medicine, vol. 85: Novel Anticancer Drug Protocols, pp. 297-321 (2003) and/or by calculating the combination index (CI) using CalcuSyn software.

The ASNS antagonist employed in the methods and materials of the invention can cause a decrease in the expression of ASNS. An ASNS mRNA antagonist is an example of such an antagonist. The ASNS antagonist can be a nucleic acid at least 10 nucleotides in length that specifically binds to and is complementary to a target nucleic acid encoding ASNS or a complement thereof, wherein the administration of the ASNS antagonist comprises introducing the nucleic acid into a cell of the subject. In some embodiments, RNA interference (RNAi) is employed and the ASNS antagonist is a small interfering RNA (siRNA). The administration of the ASNS antagonist comprises introducing into a cell of a subject, wherein the cell is capable of expressing ASNS, an effective amount of a small interfering RNA (siRNA) nucleic acid for a time and under conditions sufficient to interfere with expression of the ASNS. siRNA nucleic acids can comprise overhangs. That is, not all nucleotides need bind to the target sequence. In some embodiments, the siRNA nucleic acids comprise exclusively RNA, that is, only ribonucleic acid nucleotides. The siRNA nucleic acid can also comprise DNA, that is, deoxyribonucleic acid nucleotides. Any type of suitable small interfering RNA can be employed. In some embodiments, endogenous microRNA (miRNA) is employed. Other RNA interference agents that can be used in accordance with the invention include short hairpin RNA (shRNA), trans-acting siRNAs (tasiRNAs), repeat-associated siRNAs (rasiRNAs), small-scan (scn)RNAs, and Piwi-interacting (pi)RNAs. RNA interference nucleic acids employed can be at least 10, at least 15, 16, 17, 18, 19, 20, 21, 22, 23, 24, 25, 26, 27, 28, 29, 30, 31, 32, 33, 34, at least 35, and/or between 40-50 nucleotides in length. RNAi agent can also comprise one or more deoxyribonucleotide. The RNAi agent, e.g., siRNA or shRNA, can be comprised as a cassette by a larger nucleic acid construct such as an appropriate vector system. Examples of such vectors systems include lentiviral and adenoviral vector systems. An example of a suitable system is described in Aagaard et al., "A Facile Lentiviral Vector System for Expression of Doxycycline-Inducible shRNAs: Knockdown of the Pre-miRNA Processing Enzyme Drosha," Mol. Ther., [Epub ahead of print] (February 2007). When present as part of a larger nucleic acid construct, the resulting nucleic acid can be longer than the comprised RNAi nucleic acid, e.g., greater than 50 nucleotides in length. In some embodiments, the RNAi agent employed cleaves the target mRNA. In other embodiments, the RNAi agent employed does not cleave the target mRNA.

In addition or in the alternative to RNA interference, other nucleic acid antagonists can be employed. The ASNS antagonist can be a ribozyme that specifically cleaves an RNA molecule transcribed from a gene encoding ASNS, wherein the ribozyme comprises a target substrate binding site, a catalytic sequence within the substrate binding site, wherein the substrate binding site is complementary to a portion of an RNA molecule transcribed from the ASNS gene. The ASNS antagonist can be an antisense nucleic acid comprising a nucleotide sequence complementary to at least 8 nucleotides of a nucleic acid encoding ASNS or a complement thereof. The antisense nucleic acid can be complementary to an ASNS sequence that is of sufficient length and sequence content such that the antisense nucleic acid does not crossreact with non-ASNS nucleotide sequences. In some embodiments, crossreaction occurs but does not cause a substantial deleterious side effect.

ASNS antagonists instead of or in addition to nucleic acids can be used in accordance with materials and methods of the invention. The ASNS antagonist can comprise an antibody that specifically binds ASNS, or the antagonist can comprise a polypeptide comprising an antigen binding fragment of the antibody. In some embodiments, the antibody or polypeptide inhibits the enzymatic activity of ASNS. In some embodiments, the ASNS antagonist comprises a small molecule (low molecular weight) drug. The antagonist can inhibit ASNS. In some embodiments, the low molecular weight drug is a N-acylsulfonamide and/or a derivative thereof. In some embodiments, the low molecular weight drug is a sulfoxamide and/or derivative thereof. ASNS small molecule inhibitors include 6-diazo-5-oxo-L-norleucine, 8-N3-ATP, N-acylsulfonamide 6 [as well as other compounds described in Koroniak, L. et al., Organic Letters, 5(12):2033-2036 (2003)], adenylated sulfoximine 7b [as well as other compounds described in Richards et al., Annu. Rev. Biochem. 75:629-54 (2006)], salts, prodrugs, and combinations thereof. One or more kind of low molecular weight drug can be employed.

A method of decreasing expression of asparagine synthetase (ASNS) in a subject in need thereof is provided, the method comprising introducing into a cell of a subject an effective amount of a therapeutic nucleic acid of at least 10 nucleotides in length that specifically binds to and is complementary to a target nucleic acid encoding ASNS, wherein the introduction of the therapeutic nucleic acid results in a decrease in the expression of a gene encoding ASNS. In some embodiments, at least one of the therapeutic nucleic acid and target nucleic acid is RNA. A method for interfering with expression of asparagine synthetase (ASNS) is provided, the method comprising introducing into a cell of a subject in need of ASNS inhibition, wherein the cell is capable of expressing ASNS, an effective amount of a small interfering RNA (siRNA) nucleic acid for a time and under conditions sufficient to interfere with expression of the ASNS. In some embodiments, the RNA interference therapies further comprise administering an effective amount of at least one of a L-ASP and a pegylated L-ASP to the subject. One of need of ASNS inhibition includes, for example, a subject that suffers from a disorder characterized by undesirable cell proliferation. A subject in need of ASNS inhibition can also include one that would benefit from enhancing the efficacy of treatment with L-ASP. These methods can be used to identify ovarian cancer, leukemia, melanoma, head and neck cancer pancreatic cancer, and other patients that are more apt to respond positively to L-ASP treatment. In accordance with the methods of the invention, expression can comprise transcription and/or translation. Expression can include further processes in addition or in the alternative.

A method of decreasing cell proliferation in a subject in need thereof is provided. The method can comprise administering to the subject synergistic amounts of an ASNS mRNA antagonist and at least one of a L-ASP and a pegylated L-ASP thereby resulting in a greater decrease in undesirable cell proliferation in the subject than with the administration of the ASNS mRNA antagonist, L-ASP, or pegylated L-ASP alone. The decrease in undesirable cell proliferation can comprise a decrease in cancer cell proliferation. The decrease in cancer cell proliferation can comprise a decrease in cell proliferation of a cancer selected from the group consisting of an ovarian cancer, a renal cancer, a melanoma, a breast cancer, a brain cancer and any combination thereof. The ASNS mRNA antagonist can be an antagonist of an ASNS mRNA of the subject to which the antagonist is administered. The ASNS mRNA antagonist recognizes one or more ASNS mRNA. In some embodiments, the ASNS mRNA antagonist recognizes one or more of SEQ ID NOS: 1, 3, 5 as described herein. An ASNS mRNA antagonist can inhibit an ASNS mRNA in one or more stage of the mRNA lifecycle, e.g., mRNA transcription by a RNA polymerase, as a primary transcript, mRNA being processed, mRNA once processed with one or more exon and/or intron retained or excised and/or a poly-A tail added, and mRNA translation to protein by a ribosome. In some embodiments, the mRNA inhibitor targets a RNA polymerase. In some embodiments, a ribosomal inhibitor is employed.

The ASNS mRNA antagonist can comprise a nucleic acid. In some embodiments, the ASNS mRNA antagonist comprises a small interfering RNA (siRNA). In some embodiments, the siRNA comprises a nucleic acid comprising at least 19 consecutive ribonucleotides nucleotides adjacent to at least two deoxyribonucleotides. The deoxyribonucleotides are located at the 3' end of each nucleic acid. In some embodiments, the ASNS mRNA antagonist comprises an antisense nucleic acid comprising a nucleotide sequence complementary to at least 8 nucleotides of a nucleic acid encoding ASNS or a complement thereof. In some embodiments, the ASNS mRNA antagonist comprises a ribozyme that specifically cleaves the ASNS mRNA, wherein the ribozyme comprises a target substrate binding site, a catalytic sequence within the substrate binding site, and wherein the substrate binding site is complementary to a portion of the ASNS mRNA. In some embodiments, the ASNS mRNA antagonist comprises a short hairpin RNA (shRNA):

Any suitable natural or artificially constructed or modified L-ASP can be employed in the methods and materials of the present application. References to L-ASP herein refer to L-ASPs in general unless otherwise specified. Bacterial L-ASPs can be used in accordance with the materials and methods of the invention. In some embodiments, the bacterial L-ASP is *E. coli* L-ASP, e.g., Merck's Elspar®. Other suitable L-ASPs include those obtained from *Erwinia chrysanthemi*, e.g., Erwinase, *Serratia marcescens*, guinea pig, and Caviodea. In some embodiments, the L-ASP contains alternative or additional groups. Such groups can be selected for increasing the stability of the L-ASP. In some embodiments, the L-ASP is pegylated. Suitable L-ASP enzymes are described in Chabner et al., Cancer Chemotherapy and Biotherapy: Principles and Practice, XV, p. 879 (Philadelphia: Lippincott, Williams & Wilkins 2006). In some embodiments, the L-ASP contains alternative or additional groups. Pegylated-asparaginase is described in Hak et al., Leukemia 18: 1072-1077 (2004). Oncospar® is an example of a pegylated L-ASP. A L-ASP can be employed in the invention even though it has been modified in sequence or otherwise. The L-ASP employed should retain at least partial enzymatic activity in regards to the degradation of asparagine.

Any suitable ASNS antagonist can be used. The antagonist can be one that inhibits or downregulates to some degree the expression of the protein encoded by an ASNS gene, e.g., at the DNA, RNA, or other level of regulation. In some embodiments, the ASNS antagonist acts as an enzymatic inhibitor of ASNS. In accordance with the invention, the ASNS antagonist, such as a therapeutic nucleic acid, such as a siRNA, can target a nucleotide sequence of a ASNS gene or mRNA encoded by the same. In some embodiments, the ASNS sequence is a human sequence. For example, human ASNS is assigned Gene NCBI Entrez Gene ID No. 440, and an Online Mendelian Inheritance in Man (OMIM) No. *108370. The human ASNS gene is found on chromosome 7 at 7q21.3. Three transcriptional variants include mRNAs: NM_001673, NM_133436, and NM_183356, with corresponding protein sequences NP_001664, NP_597680, and NP_899199, respectively. Accordingly, NM_001673 is provided as SEQ ID NO: 1 with SEQ ID NO: 2 providing the amino acid sequence encoded thereby. NM_133436 is provided as SEQ ID NO: 3 with SEQ ID NO: 4 providing the amino acid sequence encoded thereby. NM_183356 is provided as SEQ ID NO: 5 with SEQ ID NO: 6 providing the amino acid sequence encoded thereby. Human genomic ASNS sequences include AC079781, CH236949, L35946, and M27054. Human ASNS mRNA sequences include AK000379, BC008723, BC014621, BC030024, BG718826, BT007113, M15798, and M27396. Human ASNS amino acid sequences include AAQ96856, EAL24115, AAA52756, AAA63266, AAH08723, AAH14621, AAP35777, AAA36781, and AAA51789. Other human sequences, as well as other species ASNSs can be employed in accordance with the invention.

In some embodiments, the subject being treated in accordance with the invention has been diagnosed with a disorder associated with altered ASNS expression. In some embodiments, the expression is high or increased relative to a standard. In some embodiments, the expression is moderate or substantially the same as a standard. In some embodiments, the expression is low or decreased relative to a standard. In some embodiments, the subject has been diagnosed with a proliferative disease such as a cancer.

In accordance with the invention, the ASNS antagonist, such as a therapeutic nucleic acid, such as a siRNA, can target a nucleotide sequence selected from the group consisting of CTGGATACTGCCAATAAGAAA (SEQ ID NO: 7), CAGAAGCTAAAGGTCTTGTTA (SEQ ID NO: 8), complements thereof, and any combination thereof. Any suitable ASNS sequence can be employed. The ASNS target sequences of the synthetic siRNAs can be designed against a human ASNS with Accession No. NM_001673 (SEQ ID NO: 1) but recognize all three ASNS transcript variants. In some embodiments, the siRNA is designated siASNS.1 and comprises a sense sequence r(GGAUACUGCCAAUAA-GAAA)dTdT (SEQ ID NO: 9) and an antisense sequence r(UUUCUUAUUGGCAGUAUCC)dAdG (SEQ ID NO: 10), designed against the gene target CT<u>GGATACTGCCAATAAGAAA</u> (SEQ ID NO: 7) (Exon 5, nt 556). In some embodiments, the siRNA is designated siASNS.2 and comprises a sense r(GAAGCUAAAGGUCU-UGUUA)dTdT (SEQ ID NO: 11) and an antisense sequence r(UAACAAGACCUUUAGCUUC)dTdG (SEQ ID NO: 12), designed against the gene target CA<u>GAAGCTAAAGGTCTTGTTA</u> (SEQ ID NO: 8) (Exon 5/6, nt 658). A negative control (siNeg) sequence can comprise r(UUCUCCGAACGUGUCACGU)dTdT (SEQ ID NO: 13) and r(ACGUGACACGUUCGGAGAA)dTdT (SEQ ID NO: 14) strands. The negative control siNeg target sequence can be AATTCTCGAACGTGTCACGT (SEQ ID NO: 15) (Qiagen Inc., Germantown Md.). The formula sense r(N19) dTdT, antisense r(N19)dX,dY, can be used in general in producing siRNAs for use with methods of the invention. Underlined portions of sequence identify the specific bases to which the siRNA molecules can be designed. siRNA molecules can be designed against any appropriate ASNS mRNA sequence.

An isolated molecule is one that has been removed from the environment in which it naturally occurs, e.g., without purposeful human intervention. An isolated molecule can be returned to the environment in which it occurs and still be considered an isolated molecule as it had been previously separated from its natural environment. Isolated molecules include isolated nucleic acids, isolated proteins, isolated polypeptides, and isolated antibodies.

A nucleic acid or nucleotide includes one or more nucleotides. Exemplary nucleic acids include RNA, DNA, and combinations thereof. Nucleic acids can include both naturally occurring as well non-naturally occurring nucleotides, ribonucleic acid nucleotides as well as deoxyribonucleic acid nucleotides. When a nucleic acid is recited it refers generically to nucleic acids include DNA and RNA unless the recitation explicitly states that the nucleic acid is a specific one, e.g., DNA or RNA. If a nucleic acid refers to a sequence that contains thymine (t), that does not necessarily indicate that the nucleic acid is DNA; in some embodiments the nucleic acid is RNA and/or DNA. Similarly, if a nucleic acid refers to a sequence that contains uracil (u) that does not necessarily indicate that the nucleic acid is RNA; in some embodiments the nucleic acid is DNA and/or RNA.

The nucleic acid molecules relevant to the invention can readily be obtained in a variety of ways, including, without limitation, chemical synthesis, cDNA or genomic library screening, expression library screening, and/or PCR amplification of cDNA. These methods and others useful for isolating such DNA are set forth, for example, by Sambrook et al., "Molecular Cloning: A Laboratory Manual," Cold Spring Harbor Laboratory Press, Cold Spring Harbor, N.Y. (1989), by Ausubel, et al., eds., "Current Protocols In Molecular Biology," Current Protocols Press (1994), and by Berger and Kimmel, "Methods In Enzymology: Guide To Molecular Cloning Techniques," vol. 152, Academic Press, Inc., San Diego, Calif. (1987).

Chemical synthesis of a nucleic acid molecule can be accomplished using methods well known in the art, such as those set forth by Engels et al., Angew. Chem. Intl. Ed., 28:716-734 (1989). These methods include, inter alia, the phosphotriester, phosphoramidite and H-phosphonate methods of nucleic acid synthesis. Nucleic acids larger than about 100 nucleotides in length can be synthesized as several fragments, each fragment being up to about 100 nucleotides in length. The fragments can then be ligated together to form a full length nucleic acid encoding the polypeptide. One method is polymer-supported synthesis using standard phosphoramidite chemistry.

Alternatively, the nucleic acid can be obtained by screening an appropriate cDNA library prepared from one or more tissue source(s) that express the polypeptide, or a genomic library from any subspecies. The source of the genomic library may be any tissue or tissues from a mammalian or other species believed to harbor a gene encoding a protein relevant to the invention. The library can be screened for the presence of a cDNA/gene using one or more nucleic acid probes (oligonucleotides, cDNA or genomic DNA fragments that possess an acceptable level of homology to the gene or gene homologue cDNA or gene to be cloned) that will hybridize selectively with the gene or gene homologue cDNA(s) or gene(s) that is (are) present in the library. The probes preferably are complementary to or encode a small region of the DNA sequence from the same or a similar species as the species from which the library was prepared. Alternatively, the probes can be degenerate. After hybridization, the blot containing the library is washed at a suitable stringency, depending on several factors such as probe size, expected homology of probe to clone, type of library being screened, number of clones being screened, and the like. Stringent washing solutions can be low in ionic strength and are used at relatively high temperatures.

Another suitable method for obtaining a nucleic acid in accordance with the invention is the polymerase chain reaction (PCR). In this method, poly(A)+ RNA or total RNA is extracted from a tissue that expresses the gene product. cDNA is then prepared from the RNA using the enzyme reverse transcriptase. Two primers typically complementary to two separate regions of the cDNA (oligonucleotides) are then added to the cDNA along with a polymerase such as Taq polymerase, and the polymerase amplifies the cDNA region between the two primers.

The invention provides for the use of isolated, purified or enriched nucleic acid sequences of 15 to 500 nucleotides in length, 15 to 100 nucleotides in length, 15 to 50 nucleotides in length, and 15 to 30 nucleotides in length, which have sequence that corresponds to a portion of one of the nucleotides described herein. The nucleic acid can be at least 17, 20, 22, or 25 nucleotides in length. The nucleic acid sequence can be 30 to 300 nucleotides in length, or 45 to 200 nucleotides in length, or 45 to 100 nucleotides in length. The nucleic acid can be at least 5, 6, 7, 8, 9, 10, 12, 15, 17, 20, 22, 25, 30, 35, 40, 50, 100, 150, 200, 250, 300, 350, 400, 450, 500, 1000, 10,000, 50,000, 100,000 or more nucleotides in length, or 100,000, 75,000, 50,000, 10,000, 5,000, 1000, 750, 500, 250, 200, 100, 50, 40, 30, 25, 22, 20, 17, 15, 12, 10, 9, 8, 7, 6, 5, or fewer nucleotides in length. The nucleic acid can have a length in a range from any one of the above lengths to any other of the above lengths including endpoints.

A nucleic acid in accordance with the invention can be 25%, 30%, 35%, 40%, 45%, 50%, 55%, 60%, 65%, 70%, 75%, 80%, 82%, 84%, 86%, 88%, 90%, 91%, 92%, 93%, 94%, 95%, 96%, 97%, 98%, 99%, and 100% identical to reference sequences provided herein. A nucleotide that hybridizes under stringent conditions to a nucleotide described herein can be employed. Unless otherwise specified, percent identities for nucleic acids and amino acid sequences are determined as follows. Percent identity of two nucleic acid sequence or two amino acid sequences is determined using the algorithm of Karlin and Altschul (Proc. Natl. Acad. Sci. USA, 87:2264-2268 (2002), modified as in Karlin and Altschul et al., Proc. Nat. Acad. Sci. USA, 90:5873-5877 (1993). Such an algorithm is incorporated into the NBLAST and XBLAST programs of Altschul et al., J. Mol. Biol. 215: 403-410 (1990). BLAST nucleotide searches are performed with the NBLAST program, score=100, wordlength=1, to obtain nucleotide sequences with a percent identity to a nucleic acid employed in the invention. BLAST protein searches are performed with the XBLAST program, score=50, wordlength=3, to obtain amino acid sequences with a percent identity to a reference polypeptide. To obtain gapped alignments for comparison purposes, Gapped BLAST is utilized as described in Altschul et al., Nucleic Acids Res., 25:3389-3402 (1997). When utilizing BLAST and Gapped BLAST programs, the default parameters of the respective programs (e.g., XBLAST and NBLAST) are used. See <www.ncbi.nih.gov>.

A nucleic acid with a sequence as described herein can be utilized as a primer or amplification oligonucleotide. Another example is a nucleic acid hybridization probe comprised of such a sequence. Unless otherwise specified, a nucleic acid and nucleic acid probe can include one or more nucleic acid analogs, labels or other substituents or moieties so long as the base-pairing function is retained. The nucleic acid probe can comprise a detectable label, such as a radioactive or fluorescent label. A variety of other detectable labels are known to those skilled in the art. Unless otherwise specified, where the sequence for a given strand is provided, the invention also includes its complement in addition or in the alternative.

In connection with nucleic acid hybridization, the term "specifically hybridizes" indicates that the probe hybridizes to a sufficiently greater degree to the target sequence than to a non-target sequence, e.g., at a level which allows ready identification of probe/target sequence hybridization under selective hybridization conditions. "Selective hybridization conditions" refer to conditions that allow such differential binding. Similarly, the terms "specifically binds" and "selective binding conditions" refer to such differential binding of any type of probe, and to the conditions that allow such differential binding.

Variables can be adjusted to optimize the specificity of a nucleic acid probe, including changes in salt concentration, temperature, pH and addition of various compounds that affect the differential affinity of GC vs. AT base pairs, such as tetramethyl ammonium chloride. [See Current Protocols in Molecular Biology, Ausubel et al. (Editors), John Wiley & Sons.] Hybridization conditions should be sufficiently stringent such that there is a significant difference in hybridization intensity between alleles, and preferably an essentially binary response, whereby a probe hybridizes to only one of the alleles. Hybridizations can be performed under stringent conditions that allow for specific binding between an oligonucleotide and a target nucleic acid. Stringent conditions are defined as any suitable buffer concentrations and temperatures that allow specific hybridization of the oligonucleotide and any washing conditions that remove non-specific binding of the oligonucleotide. For example, conditions of 5×SSPE (750 mM NaCl, 50 mM Na Phosphate, 5 mM EDTA, pH 7.4) and a temperature of 25-30° C. are suitable for allele-specific probe hybridizations. The washing conditions can range from room temperature to 60° C.

One use of probe(s) is as a primer(s) that hybridizes to a target nucleic acid sequence. Preferably such primers hybridize to a sequence not more than 300 nucleotides, more preferably not more than 200 nucleotides, still more preferably not more than 100 nucleotides, and most preferably not more than 50 nucleotides away from a site which is to be analyzed. Preferably, a primer is 100 nucleotides or fewer in length, more preferably 50 nucleotides or fewer, still more preferable 30 nucleotides or fewer, and most preferably 20 or fewer nucleotides in length. Primers or amplification oligonucleotides can be adapted to bind to or extend through a plurality of target sequences in a gene(s) identified herein. Nucleic acid probes can be provided in any suitable form. Examples include free nucleic acids as well as nucleic acids attached to a substrate such as an array. Arrays may be provided in the form of a multiplex chip. Various arrays can be employed such as cDNA arrays, spotted oligonucleotide arrays, and Affymetrix oligonucleotide arrays.

Polypeptides or fragments thereof can be expressed in an expression vector in which a gene or coding segment thereof or related construct thereof is operably linked to a native or other promoter. The promoter can be a eukaryotic promoter for expression in a mammalian cell. The transcription regulation sequences typically include a heterologous promoter and optionally an enhancer that is recognized by the host. The selection of an appropriate promoter, for example trp, lac, phage promoters, glycolytic enzyme promoters and tRNA promoters, depends on the host selected. Commercially available expression vectors can be used. Vectors can include host-recognized replication systems, amplifiable genes, selectable markers, host sequences useful for insertion into the host genome, and the like.

The expression construct can be introduced into a host cell in a number of ways depending upon the particular construction and the target host, for example, fusion, conjugation, transfection, transduction, electroporation, or injection, as described in Sambrook, supra. A wide variety of host cells can be employed for expression of the gene or coding segment thereof or related construct thereof including both prokaryotic and eukaryotic. Suitable host cells include bacteria such as E. coli, yeast, filamentous fungi, insect cells, mammalian cells, typically immortalized, e.g., mouse, CHO, human and monkey cell lines and derivatives thereof. Host cells can be selected to process the translated product to produce an appropriate mature polypeptide. Processing includes glycosylation, ubiquitination, disulfide bond formation, and general post-translational modification.

The protein can be isolated by conventional means of protein biochemistry and purification to obtain a substantially pure product, i.e., 80, 95 or 99% free of cell component contaminants, as described in Jacoby, Methods in Enzymology Volume 104, Academic Press, New York (1984); Scopes, Protein Purification, Principles and Practice, 2nd Edition, Springer-Verlag, New York (1987); and Deutscher (ed), Guide to Protein Purification, Methods in Enzymology, Vol. 182 (1990). If the protein is secreted, it can be isolated from the supernatant in which the host cell is grown. If not secreted, the protein can be isolated from a lysate of the host cells.

In addition to substantially full-length polypeptides expressed by genes or coding segments thereof, the invention includes use of biologically active fragments of the polypeptides, or analogs thereof, including organic molecules that simulate the interactions of the peptides. Biologically active fragments include any portion of the full-length polypeptide that confers a biological function on the expressed product, including ligand binding and antibody binding. Ligand binding includes binding by nucleic acids, proteins or polypeptides, small biologically active molecules or large cellular structures. In some embodiments, the polypeptide is at least 5, 6, 7, 8, 9, 10, 12, 15, 17, 20, 22, 25, 30, 35, 40, 50, 100, 150, 200, 250, 300, 350, 400, 450, 500, 1000, 10,000, 50,000, 100,000 or more amino acids in length, or 100,000, 75,000, 50,000, 10,000, 5,000, 1000, 750, 500, 250, 200, 100, 50, 40, 30, 25, 22, 20, 17, 15, 12, 10, 9, 8, 7, 6, 5, or fewer amino acids in length. A polypeptide can have a length in a range from any one of the above lengths to any other of the above lengths including endpoints. A polypeptide in accordance with the invention can be 25%, 30%, 35%, 40%, 45%, 50%, 55%, 60%, 65%, 70%, 75%, 80%, 82%, 84%, 86%, 88%, 90%, 91%, 92%, 93%, 94%, 95%, 96%, 97%, 98%, 99%, and 100% identical to reference sequence provided herein.

For uses, methods, and materials of this invention, cell proliferation can be of any suitable kind. Examples include both benign and malignant, metastatic, and hyperplasic. Cell proliferation can be normal, abnormal, controlled, uncontrolled, partially controlled, physiological, cancerous, and pathogenic. The subject treated in accordance with the invention has been diagnosed with a cancer or an increased susceptibility for a cancer. Any cancer susceptible to the treatments of the invention can be treated. As used herein, the term "cancer" is meant any malignant growth or tumor caused by abnormal and uncontrolled cell division that may spread to other parts of the body through the lymphatic system or the blood stream. The cancer can be, for example, breast cancer, prostate cancer, lung cancer, colon cancer, rectal cancer, urinary bladder cancer, non-Hodgkin lymphoma, melanoma, renal cancer, pancreatic cancer, cancer of the oral cavity, pharynx cancer, ovarian cancer, thyroid cancer, stomach cancer, brain cancer, multiple myeloma, esophageal cancer, liver cancer, cervical cancer, larynx cancer, cancer of the intrahepatic bile duct, acute myeloid leukemia, soft tissue cancer, small intestine cancer, testicular cancer, chronic lymphocytic leukemia, Hodgkin lymphoma, chronic myeloid cancer, acute lymphocytic cancer, cancer of the anus, anal canal, or anorectum, cancer of the vulva or cancer of the neck, gallbladder, or pleura, malignant mesothelioma, bone cancer, cancer of the joints, hypopharynx cancer, cancer of the eye, cancer of the nose, nasal cavity, neck, or middle ear, nasopharynx cancer, ureter cancer, peritoneum, omentum, or mesentery cancer, or gastrointestinal carcinoid tumor. The cancer can be a tumor. The tumor can be a solid tumor. The cancer can be a hematogeous malignancy. The cancer can be a leukemia. In some embodiments, the leukemia is an acute lymphoblastic leukemia. In some embodiments, the leukemia is a L-ASP sensitive leukemia. The cancer can be an ovarian cancer. In some embodiments, the ovarian cancer is an ovarian adenocarcinoma, ovarian carcinoma, clear cell ovarian cancer, endometrioid ovarian cancer, mucinous ovarian cancer, serous ovarian cancer, mixed ovarian cancer, or any combination thereof. The cancer can be a pancreatic cancer. In some embodiments, the pancreatic cancer is a pancreatic adenocarcinoma. The cancer can be a brain cancer. In some embodiments, the cancer is a glioblastoma. The cancer can be a renal cancer. In some embodiments, the renal cancer is a clear cell renal carcinoma. In some embodiments, the cancer is a breast cancer. In some embodiments, the cancer is an estrogen receptor negative breast cancer. In some embodiments, the cancer is a head and neck cancer. In some embodiments, the cancer is a melanoma. The cancer can be in an early, intermediate, or late stage. In some embodiments, the early stage cancer is an early stage ovarian cancer. The cancer can be benign or malignant. In some embodiments, the cancer is metastatic. In accordance with the present invention, the Oncomine database (http://www.oncomine.org) can be searched to identify additional cases in which L-ASP could be effective if its relationship with ASNS is dominant. In those cases, where ASNS expression is the dominant prognostic marker, L-ASP utility can be greatly optimized based on the teachings of the present invention. Other relevant cancers are described in the examples appended hereto.

A method of screening for the efficacy of L-ASP in a subject is provided. The L-ASP efficacy screened for can be for any type of L-ASP. In some embodiments, the L-ASP is pegylated L-ASP. The method can comprise detecting a level of expression of an ASNS gene in a sample from the subject, wherein the level is associated with an efficacy of L-asparaginase in decreasing cell proliferation, and identifying the efficacy based on the level of expression. In some embodiments, the level is low compared to a chosen standard and the low level is associated with an increased efficacy of L-asparginase in decreasing cell proliferation. In some embodiments, the level is high compared to a chosen standard and the high level is associated with a decreased efficacy of L-asparginase in decreasing cell proliferation. In some embodiments, the level is moderate and identical or substantially similar to a chosen standard and moderate level is associated with an acceptable efficacy of L-asparginase in decreasing cell proliferation. The level of expression can be detected based on a measurement on the amount of ASNS mRNA expressed by the ASNS gene. In some embodiments, the level of expression is detected based on a measurement on the amount of ASNS protein expressed by the ASNS gene. In some embodiments, immunohistochemistry is used to measure the amount of ASNS protein expressed. The sample can comprise cancer cells and the detecting the level of expression of ASNS protein comprises incubating the sample with a first antibody that specifically binds ASNS protein and a second antibody that binds the first antibody and allows for staining of the sample. The primary antibody and/or secondary antibody can be replaced with a polypeptide(s) comprising an antigen binding fragment of the primary and/or secondary antibody respectively. In some embodiments, a staining score of 0 or +1 on a four point scale is designated as low expression and a staining score of +2 or +3 is designated as high expression. Analysis of screening assays can be performed visually, that is, by eye, or may be automated using a spectrophotometer. In the case of immunoassays, an ELISA-based reader can be employed. Fluorometers can be employed with fluorescent labels and scintillation counters with radiolabels. In some embodiments, a homogenous phase assay is employed.

In some embodiments, the subject has been diagnosed with a disorder associated with low ASNS expression. In some embodiments, the sample screened contains cancer cells. The cells can be from any kind of cancer. In some embodiments, the sample is from a subject who has been diagnosed with and/or has a predisposition for a cell proliferative disease. In some embodiments, the proliferative disease is a cancer. In some embodiments, the subject has been diagnosed with an increased susceptibility for a cancer. The cancer can be any cancer. In some embodiments, the cancer is a tumor.

In some embodiments, the screening comprises detecting an altered level of ASNS mRNA or protein encoded by the ASNS gene. In some embodiments, the subject has been diagnosed with an ovarian cancer. In some embodiments, the subject has been diagnosed with a leukemia. In some embodiments, the subject has been diagnosed with another cancer or other cell proliferative disease. With level of ASNS expressed considered a first biomarker, the sample screened can also be screened for a second biomarker associated with efficacy of L-ASP. In some embodiments, the biomarker is associated with decreased ASNS expression. Examples of biomarkers include ovarian and leukemia biomarkers. In some embodiments, the screening and identifying steps are supplemented with an administering of L-ASP to the subject based on an identification of an increased efficacy of treatment with L-ASP. The level of expression of ASNS constitutes a biomarker for L-ASP efficacy in accordance with the invention. Other suitable biomarkers that can be used in conjunction with the biomarker of the invention are discussed in Ludwig, J. A. Nature Reviews Cancer 2005; 5: 845-856, which can be adapted for use in the invention.

In some embodiments, the sample is screened for the level of expression of a second gene associated with efficacy of L-ASP. In some embodiments, the subject possesses one or more characteristics from the group consisting of a p53 mutation, altered HER-2/neu expression, altered EGFR expression, CD10 negativity, MLL gene rearrangements, carboplatin sensitivity, taxane resistance, adriamycin resistance, and any combination thereof. A subject possesses one or more characteristic from the group consisting of a p53 mutation, altered HER-2/neu expression, altered EGFR expression, CD10 negativity, MLL gene rearrangements, carboplatin sensitivity, taxane resistance, adriamycin resistance, and any combination thereof. The biomarkers of the invention can be used to complement other biomarkers or be used when those biomarkers fail.

In some embodiments, the method of screening further comprises administering an ASNS inhibitor to the subject. In some embodiments, the method of screening further comprises administering at least one of a L-ASP and a pegylated L-ASP to the subject based on an identification of an increased efficacy for treatment with a L-ASP or pegylated L-ASP.

Kits, compositions, unit doses, drug containers, and various medical paraphernalia are provided. These items can be used in accordance with method of the invention. The kits, compositions, doses, containers, and other paraphernalia can include instructions for use. In some embodiments, the kit comprises at least one of an ASNS antagonist and at least one of a L-ASP and a pegylated L-ASP. Such a kit can be used, for example, as part of a combination therapy. A combination therapy can combine methods of the invention. A combination therapy can also combine a method of the invention with another method.

A composition is provided comprising an ASNS antagonist and at least one of a L-ASP and a pegylated L-ASP. The composition can further comprise a pharmaceutically acceptable carrier. The composition can further comprise other suitable components as well. The ASNS antagonist of the composition can be any suitable ASNS antagonist such as those described herein for the methods of the invention. The L-ASP of the composition can be any suitable L-ASP such as those described herein for the methods of the invention. The methods of the invention can employ the compositions of the invention. A composition comprising an ASNS mRNA antagonist and at least one of a L-ASP and a pegylated-L-ASP is provided. The ASNS mRNA antagonist of the composition can be a small interfering RNA (siRNA). In some embodiments, the ASNS mRNA antagonist is selected from the group consisting of an antisense nucleic acid, a ribozyme, a short hairpin mRNA (shRNA), and any combination thereof. The composition can further comprise a pharmaceutically acceptable carrier.

A kit is provided that comprises a probe for detecting a level of expression of the asparagine synthetase (ASNS) gene in a sample from a subject, wherein the level is associated with an efficacy of L-asparaginase in decreasing cell proliferation and the efficacy is identified based on the level of expression. In some embodiments, the probe is a nucleic acid that specifically binds to an ASNS nucleic acid. The probe nucleic acid can specifically bind to a sequence selected from the group consisting of 10 or more continuous nucleotides of any one of SEQ ID NOS: 1, 3, and 5. In some embodiments, the probe is an antibody or an antigen binding fragment thereof that specifically binds to an ASNS polypeptide. In some embodiments, the antibody binds an ASNS epitope comprised by SEQ ID NO: 2, 4, and/or 6 and optionally comprises the four amino acid sequence Thr-Asp-Pro-Ser (TDPS) (SEQ ID NO: 16).

The antibody or fragment thereof further can comprise a detectable label. In some embodiments, the label is selected from the group consisting of a radiolabel, a fluorescent label, an epitope recognizable by a secondary antibody, and a combination thereof. The kit can comprise a secondary antibody or antigen binding fragment thereof that specifically binds the probe antibody. In some embodiments, the kit further comprises an L-ASP. In some embodiments, the L-ASP is pegylated. The kit can further comprise an ASNS antagonist, in addition to or in the alternative to a L-ASP.

A kit comprising an asparagine synthetase (ASNS) mRNA antagonist and at least one of a L-asparaginase (L-ASP) and a pegylated-L-ASP is provided. The ASNS mRNA antagonist of the kit can be a small interfering RNA (siRNA). In some embodiments, the ASNS mRNA antagonist is selected from the group consisting of an antisense nucleic acid, a ribozyme, a short hairpin mRNA (shRNA), and any combination thereof.

Uses of an ASNS antagonist and at least one of a L-ASP and a pegylated L-ASP to manufacture a medicament for treatment of cell proliferation are provided. Uses of a nucleic acid that interferes with the expression of ASNS to manufacture a medicament for treatment of cell proliferation are provided. The use can employ an ASNS mRNA antagonist, e.g., a siRNA. In some embodiments, the ASNS mRNA antagonist is an antisense nucleic acid, a ribozyme, a short hairpin RNA and/or a combination of the same. The cell proliferation treated in a subject can be undesirable, e.g., proliferation of cancer cells.

In accordance with an aspect of the invention, a L-Asparaginase (L-ASP) therapy is provided, wherein a cell, such as an acute lymphocytic leukemia cell or other cell with low asparagine synthetase (ASNS) is starved by injecting bacterial L-ASP, which catabolizes asparagine in various body compartments such as the bloodstream.

Negative correlations between ASNS expression and sensitivity to the drug L-asparaginase can be measured in such subsets as leukemias and ovarian cancers [Scherf, U. et al., Nat Genet. 24, 236-44 (2000)]. DNA copy level by array comparative genomics hybridization can also be employed in such measurements. [Bussey et al., Mol Cancer Ther 5, 853-67 (2006)].

The subjects treated, screened and otherwise related to the method of the invention can include any suitable living organism. The ASNS antagonists and L-ASPs can also be derived from such living organisms. The subject can be a eukaryotic organism such as a plant or animal. The eukaryote can be a fungus. The eukaryote can be a yeast. The yeast can be *S. cerevisiae*. The animal can be a vertebrate or invertebrate. The vertebrate can be a fish. The vertebrate can be a bird such as a chicken. The vertebrate can be a mammal such as a rodent, a rabbit, a primate, a cat, a dog, a pig, a horse, a goat, a sheep, a cow, a guinea pig, llama, or a camel. The rodent can be a mouse, a hamster, a gerbil, or a rat. The primate can be a monkey, an ape, a rhesus monkey, an orangutan, a baboon, a chimpanzee, a bonobo, or a human. The invertebrate can be an insect.

The sample from a subject tested can constitute any appropriate biological sample regardless of how the sample is obtained or how long it has been stored. Sample can contain discrete cells, single cells, tissues, or organs. A sample need not contain intact cells. The sample can include DNA, cDNA, RNA, protein, and any combination thereof. The sample tested need not be a physiological sample, but can be in the form of information, print, electronic, or other form, that was derived from a biological sample.

Methods, kits, and materials for the detection of ASNS nucleic acids and polypeptides are provided. For example, such methods, kits, and materials can be used as part of the screening and identification of candidate subjects having an altered susceptibility for L-asparaginase treatment in decreasing cell proliferation, such as one that would provide for an increased efficacy of a L-ASP treatment. A method of detecting ASNS in a sample is provided comprising contacting a sample with a nucleic acid probe under hybridizing conditions comprising at least 10 contiguous nucleotides from a ASNS sequence or a complement thereof or a combination thereof; and detecting the presence, absence, quantitative amount, and/or relative amount of ASNS sequence in the sample. The probe can be labeled. The label can be selected from the group consisting of a radiolabel, a fluorescent label, and any combination thereof. The probe can be a PCR primer, wherein the contacting step is performed as part of a PCR amplification assay, and wherein the detection step comprises determining whether the assay has resulted in an amplified product. A kit for the detection of ASNS and/or inhibition of ASNS is provided comprising a human ASNS nucleic acid can be at least one of an ASNS nucleic acid; a fragment thereof of at least 10 contiguous nucleotides; a complement of any of the preceding, and a combination of two or more of the preceding. A method of detecting human ASNS in a sample is provided comprising providing a nucleic acid encoding a ASNS polypeptide comprising an ASNS amino acid sequence or a polypeptide comprising an immunologically specific epitope thereof; expressing an ASNS polypeptide comprising an ASNS amino acid sequence or a polypeptide comprising an immunologically specific epitope thereof from the isolated nucleic acid; generating an antibody specific to the polypeptide obtained or a polypeptide comprising an antigen binding fragment thereof; contacting a sample with an antibody specific to human ASNS or the antigen binding fragment thereof generated; and detecting the presence or absence of ASNS in the sample. The antibody can be labeled. The label can be selected from the group consisting of a radiolabel, a fluorescent label, an enzyme, and any combination thereof. The antibody can be one or more of a monoclonal, polyclonal, chimeric, and humanized antibodies. A kit for the detection of ASNS and/or inhibition of ASNS is provided comprising an isolated antibody that specifically reacts with human ASNS or a polypeptide comprising an antigen binding fragment of the antibody. The antibody can be one or more of a monoclonal, polyclonal and humanized antibodies. Antibody methods, kits, and uses can employ immunohistochemistry, homogenous enzyme immunoassays, sandwich immunoassays, and immunoprecipitation-based assays.

Antibodies specific for ASNS and polypeptides comprising antigen binding fragments thereof are provided as well as methods, uses, compositions, and kits employing the same. A method of forming an antibody specific to human ASNS or a polypeptide comprising providing a nucleic acid encoding an ASNS polypeptide or a polypeptide comprising an immunologically specific epitope thereof; expressing an ASNS polypeptide comprising an ASNS amino acid sequence or a polypeptide comprising an immunologically specific epitope thereof from the isolated nucleic acid; and generating an antibody specific to the polypeptide obtained in step or a polypeptide comprising an antigen binding fragment thereof. An antibody or polypeptide comprising an antigen binding fragment thereof produced by the aforementioned method is provided. An isolated antibody or isolated polypeptide comprising an antigen binding fragment thereof that specifically binds a human ASNS comprising an ASNS amino acid sequence is provided. Such an antibody can be generated using any acceptable method(s) known in the art. The antibodies as well as kits, methods, and other aspect of the invention employing antibodies can comprise one or more of the following a polyclonal antibody, a monoclonal antibody, and a humanized antibody.

Antibodies can be used as probes, therapeutic treatments and other uses. Polyclonal and/or monoclonal antibodies and antibody fragments capable of binding to a portion of the gene product relevant for identifying a given target are provided. Antibodies can be made by injecting mice, rabbits, goats, or other animals with the translated product or synthetic peptide fragments thereof. Monoclonal antibodies are screened as are described, for example, in Harlow & Lane, Antibodies, A Laboratory Manual, Cold Spring Harbor Press, New York (1988); Goding, Monoclonal antibodies, Principles and Practice (2d ed.) Academic Press, New York (1986). Monoclonal antibodies are tested for specific immunoreactivity with a translated product and lack of immunoreactivity to the corresponding prototypical gene product. These antibodies are useful in diagnostic assays or as an active ingredient in a pharmaceutical composition.

Polyclonal or monoclonal therapeutic antibodies useful in practicing this invention can be prepared in laboratory animals or by recombinant DNA techniques using the following methods. Polyclonal antibodies are raised in animals by multiple subcutaneous (sc) or intraperitoneal (ip) injections of the gene product molecule or fragment thereof in combination with an adjuvant such as Freund's adjuvant (complete or incomplete). To enhance immunogenicity, it may be useful to first conjugate the gene product molecule or a fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl, or $R^1 N=C=NR$, where R and $R^1$ are different alkyl groups. Alternatively, immunogenic conjugates can be produced recombinantly as fusion proteins.

Animals are immunized against the immunogenic conjugates or derivatives (such as a fragment containing the target amino acid sequence) by combining about 1 mg or about 1 microgram of conjugate (for rabbits or mice, respectively) with about 3 volumes of Freund's complete adjuvant and injecting the solution intradermally at multiple sites. Approximately 7 to 14 days later, animals are bled and the serum is assayed for antibody titer. Animals are boosted with antigen repeatedly until the titer plateaus. The animal can be boosted with the same molecule or fragment thereof as was used for the initial immunization, but conjugated to a different protein and/or through a different cross-linking agent. In addition, aggregating agents such as alum are used in the injections to enhance the immune response.

Monoclonal antibodies can be prepared by recovering spleen cells from immunized animals and immortalizing the cells in conventional fashion, e.g., by fusion with myeloma cells. The clones are then screened for those expressing the desired antibody. The monoclonal antibody preferably does not cross-react with other gene products. Non-human antibodies can be humanized using any applicable method known in the art. A humanized antibody can be produced using a transgenic animal whose immune system has been partly or fully humanized. Chimeric antibodies can be produced using any known technique in the art. See, e.g., U.S. Pat. Nos. 5,169,939; 5,750,078; 6,020,153; 6,420,113; 6,423,511; 6,632,927; and 6,800,738.

Preparation of antibodies using recombinant DNA methods such as the phagemid display method, can be accomplished using commercially available kits, as for example, the Recombinant Phagemid Antibody System available from Pharmacia (Uppsala, Sweden), or the SurfZAP™ phage display system (Stratagene Inc., La Jolla, Calif.).

Bispecific antibodies that specifically bind to one protein and that specifically bind to other antigens relevant to pathology and/or treatment are produced, isolated, and tested using standard procedures that have been described in the literature. [See, e.g., Pluckthun & Pack, Immunotechnology, 3:83-105 (1997); Carter, et al., J. Hematotherapy, 4:463-470 (1995); Renner & Pfreundschuh, Immunological Reviews, 1995, No. 145, pp. 179-209; Pfreundschuh U.S. Pat. No. 5,643,759; Segal, et al., J. Hematotherapy, 4:377-382 (1995); Segal, et al., Immunobiology, 185:390-402 (1992); and Bolhuis, et al., Cancer Immunol. Immunother., 34: 1-8 (1991)].

A therapeutic agent, which can be a compound and/or a composition, relevant to the invention can comprise a small molecule, a nucleic acid, a protein, an antibody, or any other agent with one or more therapeutic property. The therapeutic agent can be formulated in any pharmaceutically acceptable manner. In some embodiments, the therapeutic agent is prepared in a depot form to allow for release into the body to which it is administered is controlled with respect to time and location within the body (see, for example, U.S. Pat. No. 4,450,150). Depot forms of therapeutic agents can be, for example, an implantable composition comprising the therapeutic agent and a porous or non-porous material, such as a polymer, wherein the therapeutic agent is encapsulated by or diffused throughout the material and/or degradation of the non-porous material. The depot is then implanted into the desired location within the body and the therapeutic agent is released from the implant at a predetermined rate.

The therapeutic agent that is used in the invention can be formed as a composition, such as a pharmaceutical composition comprising a carrier and a therapeutic compound. Pharmaceutical compositions containing the therapeutic agent can comprise more than one therapeutic agent. The pharmaceutical composition can alternatively comprise a therapeutic agent in combination with other pharmaceutically active agents or drugs, such as chemotherapeutic agents, for example, a cancer drug.

The carrier can be any suitable carrier. Preferably, the carrier is a pharmaceutically acceptable carrier. With respect to pharmaceutical compositions, the carrier can be any of those conventionally used and is limited only by chemico physical considerations, such as solubility and lack of reactivity with the active compound(s), and by the route of administration. In addition to the following described pharmaceutical composition, the therapeutic compounds of the present inventive methods can be formulated as inclusion complexes, such as cyclodextrin inclusion complexes, or liposomes.

The pharmaceutically acceptable carriers described herein, for example, vehicles, adjuvants, excipients, and diluents, are well-known to those skilled in the art and are readily available to the public. The pharmaceutically acceptable carrier can be chemically inert to the active agent(s) and one which has no detrimental side effects or toxicity under the conditions of use. The choice of carrier can be determined in part by the particular therapeutic agent, as well as by the particular method used to administer the therapeutic compound. There are a variety of suitable formulations of the pharmaceutical composition of the invention. The following formulations for oral, aerosol, parenteral, subcutaneous, transdermal, transmucosal, intestinal, intramedullary injections, direct intraventricular, intravenous, intranasal, intraocular, intramuscular, intraarterial, intrathecal, intraperitoneal, rectal, and vaginal administration are exemplary and are in no way limiting. More than one route can be used to administer the therapeutic agent, and in some instances, a particular route can provide a more immediate and more effective response than another route. Depending on the specific disorder being treated, such agents can be formulated and administered systemically or locally. Techniques for formulation and administration may be found in Remington's Pharmaceutical Sciences, 18th ed., Mack Publishing Co., Easton, Pa. (1990).

Formulations suitable for oral administration can include (a) liquid solutions, such as an effective amount of the inhibitor dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard or soft shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the inhibitor in a flavor, usually sucrose and acacia or tragacanth, as well as pastilles comprising the inhibitor in an inert base, such as gelatin and glycerin, or sucrose and acacia, emulsions, gels, and the like containing, in addition to, such excipients as are known in the art.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The therapeutic agent, alone or in combination with other suitable components, can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non pressured preparations, such as in a nebulizer or an atomizer. Such spray formulations also may be used to spray mucosa. Topical formulations are well known to those of skill in the art. Such formulations are particularly suitable in the context of the invention for application to the skin.

Injectable formulations are in accordance with the invention. The parameters for effective pharmaceutical carriers for injectable compositions are well-known to those of ordinary skill in the art [see, e.g., Pharmaceutics and Pharmacy Practice, J. B. Lippincott Company, Philadelphia, Pa., Banker and Chalmers, eds., pages 238 250 (1982), and ASHP Handbook on Injectable Drugs, Toissel, 4th ed., pages 622 630 (1986)]. For injection, the agents of the invention can be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Formulations suitable for parenteral administration include aqueous and non aqueous, isotonic sterile injection solutions, which can contain anti oxidants, buffers, bacteriostats, and solutes that render the formulation isotonic with the blood of the intended recipient, and aqueous and non aqueous sterile suspensions that can include suspending agents, solubilizers, thickening agents, stabilizers, and preservatives. The therapeutic agent can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, poly(ethyleneglycol) 400, glycerol, dimethylsulfoxide, ketals such as 2,2-dimethyl-1,3-dioxolane-4-methanol, ethers, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the drug in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The therapeutic agent can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

The exact formulation, route of administration and dosage can be chosen by the individual physician in view of the patient's condition. [See, e.g., Fingl et. al., in The Pharmacological Basis of Therapeutics, 1975, Ch. 1 p. 1]. The attending physician can determine when to terminate, interrupt, or adjust administration due to toxicity, or to organ dysfunctions. Conversely, the attending physician can also adjust treatment to higher levels if the clinical response were not adequate, precluding toxicity. The magnitude of an administrated dose in the management of disorder of interest will vary with the severity of the disorder to be treated and the route of administration. The severity of the disorder can, for example, be evaluated, in part, by standard prognostic evaluation methods. The dose and perhaps dose frequency, can vary according to the age, body weight, and response of the individual patient. A program comparable to that discussed above can be used in veterinary medicine.

Use of pharmaceutically acceptable carriers to formulate the compounds herein disclosed for the practice of the invention into dosages suitable for systemic administration is within the scope of the invention. With proper choice of carrier and suitable manufacturing practice, the compositions relevant to the invention, in particular, those formulated as solutions, can be administered parenterally, such as by intravenous injection. The compounds can be formulated readily using pharmaceutically acceptable carriers well known in the art into dosages suitable for oral administration. Such carriers enable the compounds relevant to the invention to be formulated as tablets, pills, capsules, liquids, gels, syrups, slurries, tablets, dragees, solutions, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly. Materials and methods described for one aspect of the invention can also be employed in other aspects of the invention. For example, a material such a nucleic acid or antibody described for use in screening assays can also be employed as therapeutic agents and vice versa.

The following examples further illustrate the invention but, of course, should not be construed as in any way limiting its scope. Any in vitro examples described can also be repeated in plant, animal or other models, as well as in humans.

Example 1

This example demonstrates that ASNS expression and DNA copy number, e.g., low ASNS expression and DNA copy number, are negatively correlated with L-ASP activity in respect to limiting cell growth proliferation. ASNS transcript levels are measured using four different microarray platforms: cDNA array, Affymetrix Hu6800 array, Affymetrix U95 array, and Affymetrix U133 array. ASNS copy number (relative to mean ploidy) is assessed from array CGH, based on a BAC probe on 7q near the locus of ASNS. Comparative genomic hybridization using bacterial artificial chromosome microarrays [Bussey, K. J. et al. Mol Cancer Ther 5, 853-67 (2006)] yield a correlation coefficient −0.98 (−1.00 to −0.84) for the relationship between ASNS DNA copy number (relative to mean ploidy) and L-ASP activity in the ovarian lines.

The protocol for cell harvests is as follows. Seed cultures of the 60 cell lines are drawn from aliquoted stocks, passaged once in T-162 flasks, and monitored frequently for degree of confluence. The medium is RPMI-1640 with phenol red, 2 mM glutamine, and 5% fetal bovine serum. Fetal bovine serum is obtained from the same large batches as are used by the Developmental Therapeutics Program (DTP) of the U.S. National Cancer Institute (NCI). One day before harvest, the cells are re-fed. Attached cells are harvested at ~80% confluence, as assessed for each flask by phase microscopy. Suspended cells are harvested at ~0.5×106 cells/mL. In pilot studies, samples of medium show no appreciable change in pH between re-feeding and harvest, and no color change in the medium is seen in any of the flasks harvested. The time from incubator to stabilization of the preparation is kept to <1 min. Total RNA is purified using the Qiagen (Valencia, Calif.) RNeasy Midi Kit according to manufacturer's instructions. The RNA is then quantitated spectrophotometrically and aliquoted for storage at −80° C. The samples for HG-U95 and HG-U133 microarrays are labeled and hybridized to the arrays according to standard procedures by GeneLogic, Inc. (http://www.genelogic.com/docs/pdfs/dataGenProduct-Sheet.pdf). Protocols for labeling and hybridization are carried out for cDNA microarrays as described in Scherf, et al., Nat Genet. 24, 236-44 (2000) and Ross, et al., Nat Genet. 24, 227-35 (2000), and for hybridization to Affymetrix HU6800 arrays as described in Staunton, et al., Proc Natl Acad Sci USA 98, 10787-92 (2001). Procedures for purification of DNA and its use in array CGH with "OncoBAC" DNA microarrays are carried out as described in Bussey et al., Mol Cancer Ther 5, 853-67 (2006).

ASNS expression is evaluated in seven of the NCI-60 ovarian cell lines using four different microarray platforms: cDNA [Scherf, U. et al. A gene expression database for the molecular pharmacology of cancer. Nat Genet. 24, 236-44 (2000)], Affymetrix Hu6800 [Staunton, J. E. et al. Chemosensitivity prediction by transcriptional profiling. Proc Natl Acad Sci USA 98, 10787-92 (2001)], Affymetrix U95, and Affymetrix U133 arrays. The NCI-60 panel consists of sixty human cancer cell lines used by the DTP of the U.S. NCI to screen >100,000 chemical compounds for anticancer activity since 1990. For the relationship between ASNS expression and L-ASP-activity, those platforms yield Pearson correlation coefficients and 95% confidence intervals of −0.89 (−0.98 to −0.41), −0.90 (−0.98 to −0.46), −0.85 (−0.98 to −0.28), and −0.86 (−0.98 to −0.28), respectively. Correlation data for the experiment appears in Tables 1A and 1B. In Tables 1A and 1B, cell lines are listed in the far left column and microarrays are listed in the top row. Pearson's correlation "r" values are displayed in the bottom row, which are obtained from the slope generated by the data. The $GI_{50}$ column is the amount of L-ASP required to limit cell growth proliferation by 50%, and the column values correspond to abscissa x-values of $\log_{10}$ (L-ASP Activity) for the various cell types listed in first column if the data were presented in a graph. The remaining five columns contain the ordinate y-axis values of $\log_2$ (ASNS mRNA Expression) for the various cell types listed in first column for each array.

TABLE 1A

|  | $GI_{50}$ | cDNA | Affymetrix Hu6800 | Affymetrix U95 |
|---|---|---|---|---|
| IGROV1 | −0.8540822 | −0.2045191 | −0.5307202 | −0.5892059 |
| OVCAR-8/ADR | 0.8533778 | −1.26388 | −2.033221 | −1.537439 |
| OVCAR-3 | −0.6467372 | 0.8856863 | 0.9906262 | 1.127641 |
| OVCAR-4 | −2.050402 | 1.19814 | 1.279057 | 1.382323 |
| OVCAR-5 | 0.2961678 | −1.268343 | −2.033221 | −1.36384 |
| OVCAR-8 | 0.4597178 | −1.481758 | −2.033221 | −1.084472 |
| SK-OV-3 | 0.1181578 | −0.3739908 | −1.385522 | −1.585533 |
| Pearson's Correlation (r): |  | −0.89 | −0.90 | −0.85 |

TABLE 1B

|  | $GI_{50}$ | Affymetrix U133 | aCGH |
|---|---|---|---|
| IGROV1 | −0.8540822 | −0.5702379 | 0.076347 |
| OVCAR-8/ADR | 0.8533778 | −2.228971 | −0.887441 |
| OVCAR-3 | −0.6467372 | 0.9221592 | −0.072111 |
| OVCAR-4 | −2.050402 | 1.402569 | 0.739271 |
| OVCAR-5 | 0.2961678 | −1.331497 | −0.280151 |
| OVCAR-8 | 0.4597178 | −0.520938 | −0.462259 |
| SK-OV-3 | 0.1181578 | −1.356778 | −0.324259 |
| Pearson's Correlation (r): |  | −0.86 | −0.98 |

Example 2

This example and those that follow demonstrate the efficacy of ASNS antagonists, e.g., siRNA, and the ability of ASNS siRNA to silence ASNS. A quantitative Western blot method and an optimized cell viability assay are developed for use in conjunction with RNA interference (RNAi). Those tools are applied to three ovarian cell lines covering a range of ASNS expression—OVCAR-4, OVCAR-3, and OVCAR-8, which express ASNS at high, medium and low levels, respectively. Two independent siRNAs targeted to different regions of the ASNS transcript are found to potently and specifically silence ASNS mRNA in all three cell lines, as measured by a branched-DNA or RNA assay. A decrease of ASNS mRNA expression by 80%-90% can be observed in all three cell lines, as assessed by branched-DNA assay.

For cell culture and RNA interference, the following materials and methods are employed. Cell lines are routinely maintained in RPMI-1640 containing 5% fetal bovine serum and 2 mM L-glutamine. For mRNA and MTS assays, transfections mediated by cationic lipid are performed in 96-well plates. Cells are seeded on a complex of the appropriate siRNA (Qiagen Inc., Germantown, Md.) and Oligofectamine (Invitrogen, Carlsbad, Calif.) in unsupplemented growth medium. Final amounts in each well are 50 nM siRNA, 0.475 µL Oligofectamine, and 5,000 OVCAR-4 cells in 100 µL of medium; 30 nM siRNA, 0.40 µL Oligofectamine, and 4,300 OVCAR-3 cells in 100 µL medium; 5 nM siRNA, 0.75 µL Oligofectamine, and 2,750 OVCAR-8 cells in 100 µL medium; 5 nM siRNA, 0.75 µL Oligofectamine, and 4,700 OVCAR-8/ADR cells in 100 µL medium. Three replicate wells are used in mRNA determinations. The amount of Oligofectamine is scaled to 200,000 cells per well in 6-well plates for duplicate protein determinations.

The ASNS target sequences of the synthetic siRNAs are designed against NM_001673 but recognize all three ASNS transcript variants. The siASNS.1 sequence can consist of sense r(GGAUACUGCCAAUAAGAAA)dTdT (SEQ ID NO: 9) and antisense r(UUUCUUAUUGGCAGUAUCC) dAdG (SEQ ID NO: 10), designed against the gene target CT<u>GGATACTGCCAATAAGAAA</u> (SEQ ID NO: 7) (Exon 5, nt 556). The siASNS.2 sequence can consist of sense r(GAAGCUAAAGGUCUUGUUA)dTdT (SEQ ID NO: 11) and antisense r(UAACAAGACCUUUAGCUUC)dTdG (SEQ ID NO: 12), designed against the gene target CA<u>GAAGCTAAAGGTCTTGTTA</u> (SEQ ID NO: 8) (Exon 5/6, nt 658). The negative control (siNeg) sequence consists of r(UUCUCCGAACGUGUCACGU)dTdT (SEQ ID NO: 13) and r(ACGUGACACGUUCGGAGAA)dTdT (SEQ ID NO: 14) strands (Qiagen Inc., Germantown Md.). Underlined portions of sequence identify the specific bases to which the siRNA molecules are designed. Cells and complex are incubated for 1 h at room temperature before transferring to an incubator.

For detection of ASNS mRNA, the following materials and methods are employed. ASNS mRNA levels are assayed at 48 hours using the Quantigene Branched-DNA Assay (probe set nts. 670-1321, which recognizes all three ASNS transcript variants) according to the manufacturer's protocol (Genospectra Inc, Fremont, Calif.). The luminescence of each sample is measured with a Perkin Elmer Victor3 V 1420 Multilabel Counter. Each background signal value (absence of capture probe) is subtracted from the corresponding ASNS or cyclophillin-B (PPIB; probe set nts. 74-432) value to correct for non-specific binding. ASNS levels for a given sample are then normalized to PPIB levels for that sample. Normalized ASNS levels in siASNS-transfected cells are compared with those in siNeg-transfected cells, which served as the control.

ASNS expression following synthetic siRNA transfection of ovarian cancer cell lines. Branched-DNA assay for normalized ASNS mRNA values 48 hours after transfection of siNeg, siASNS.1, or siASNS.2 for OVCAR-4, OVCAR-3, and OVCAR-8 are shown in Tables 2A-2C respectively. Values are normalized mRNA expression. "SD" refers to the standard deviation of the data.

TABLE 2A (OVCAR-4)

| siNeg | siASNS.1 | siASNS.2 |
|---|---|---|
| 0.689 | 0.125 | 0.128 |
| 0.643 | 0.11 | 0.161 |
| 0.676 | 0.108 | 0.142 |
| 0.67 (Mean) | 0.11 (Mean) | 0.14 (Mean) |
| 0.02 (SD) | 0.01 (SD) | 0.02 (SD) |

TABLE 2B (OVCAR-3)

| siNeg | siASNS.1 | siASNS.2 |
|---|---|---|
| 0.54 | 0.099 | 0.115 |
| 0.65 | 0.09 | 0.18 |
| 0.67 | 0.17 | 0.16 |
| 0.62 (Mean) | 0.12 (Mean) | 0.15 (Mean) |
| 0.07 (SD) | 0.04 (SD) | 0.03 (SD) |

TABLE 2C (OVCAR-8)

| siNeg | siASNS.1 | siASNS.2 |
|---|---|---|
| 0.168 | 0.02 | 0.029 |
| 0.178 | 0.024 | 0.035 |
| 0.191 | 0.029 | 0.043 |
| 0.18 (Mean) | 0.02 (Mean) | 0.04 (Mean) |
| 0.01 (SD) | 0.00 (SD) | 0.01 (SD) |

Example 3

This example demonstrates the decreases in protein level following RNAi using Western blots and other means, the decreases corresponding to the results described in Example 2 for mRNA reduction. The time course of ASNS protein knockdown is analyzed following RNAi.

For detection of ASNS protein, the following materials and methods are employed. At selected time points, e.g., 24, 48, 72 and 96 h, cells seeded in 6-well plates for protein determination are washed twice with ice cold PBS. Ice cold lysis buffer (20 mM Tris pH 8, 137 mM NaCl, 1 mM $MgCl_2$, 1 mM $CaCl_2$, 1% Triton X-100, 10% glycerol, 1 mM PMSF) is then added to each well, and plates are rocked for 5 min at 4° C. The lysate is centrifuged at 14,000 rpm for 10 minutes, and the supernatant is then assayed for total protein using the Bio-Rad DC Protein Assay (Bio-Rad Laboratories, Hercules, Calif.) and a BSA standard.

For Western blots, 10 μg of supernatant is loaded onto 10% acrylamide gels, with the exception that 5 μg is loaded for all OVCAR-3 samples. After electrophoresis and transfer to PVDF membranes, non-specific binding is minimized by blocking for 2 hours with TBST containing 1% (w/v) polyvinylpyrrolidone and 10% (w/v) Dextran (Sigma-Aldrich) at room temperature. The primary antibody, rabbit anti-human ASNS, is added directly to the blocking solution at 0.4 μg/mL. IRDye 800 goat anti-rabbit secondary antibody (Rockland, Gilbertsville, Pa.) is prepared at 1:6000 in fresh blocking solution. Membranes are incubated with primary antibody for 2 hours and subsequently with secondary antibody for 4 hours with gentle rocking at room temperature. The membranes are washed four times with TBST between steps. Membranes are scanned on a Li-Cor Odyssey Imager. The signal is related linearly to the amount of lysate up to at least 10 μg total protein. To confirm specificity of the primary antibody, a replicate membrane is treated with nonspecific rabbit IgG instead of primary antibody. It yields no bands. Bands are quantitated using the Odyssey version 1.2 software. Background is generally negligible but is nevertheless accounted for by the Li-Cor Odyssey software. Samples inoculated with the non-specific siNeg sequence serve as the control. Protein levels obtained for siASNS-treated cells are divided by the corresponding levels for siNeg-treated cells and multiplied by 100 to yield percent control. Percent control values are then averaged and standard deviations computed (n=3 for mRNA, n=2 for protein).

Lysates prepared from siRNA-transfected OVCAR-3, OVCAR-4, and OVCAR-8 cells are accordingly Western blotted using a polyclonal rabbit anti-human ASNS antibody for detection and quantitation. For the quantitation of ASNS protein from Western blots, relative ASNS levels for the three ovarian cell lines are determined by normalizing the ASNS intensity for siNeg- and siASNS-treated 24-, 48-, 72- and 96-h samples to the total amount of protein loaded. For comparing values between different cell lines, one can average the normalized ASNS intensity values obtained from siNeg-treatement. Values in the Table 3 represents such an example. OVCAR-4, OVCAR-3, and OVCAR-8 cells exhibited high, medium, and low protein levels, respectively, when transfected with siNeg. Results are shown in table 3. Values are normalized protein expression.

TABLE 3

| OVCAR-4 | OVCAR-3 | OVCAR-8 |
|---|---|---|
| 3.12 | 2.5 | 1.05 |
| 2.9 | 2.8 | 0.9 |
| 3.27 | 2.62 | 0.95 |
| 3.46 | 2.74 | 0.9 |
| 3.19 (Mean) | 2.67 (Mean) | 0.95 (Mean) |
| 0.24 (SD) | 0.13 (SD) | 0.07 (SD) |

Figure 1A:
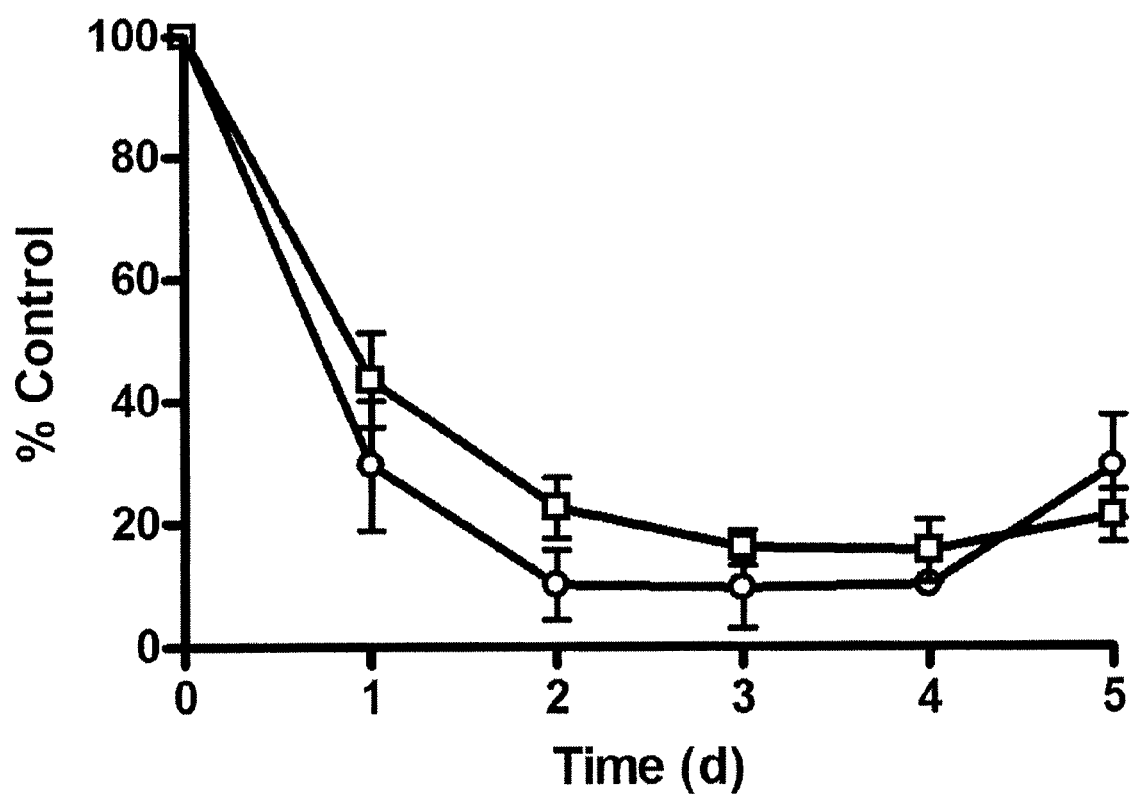
FIG. 1A depicts ASNS protein expression in the ovarian cell line OVCAR-4 following transfection of siASNS.1 (circle) or siASNS.2 (square) as percent of siNeg control as a function of time in days.
Figure 1B:
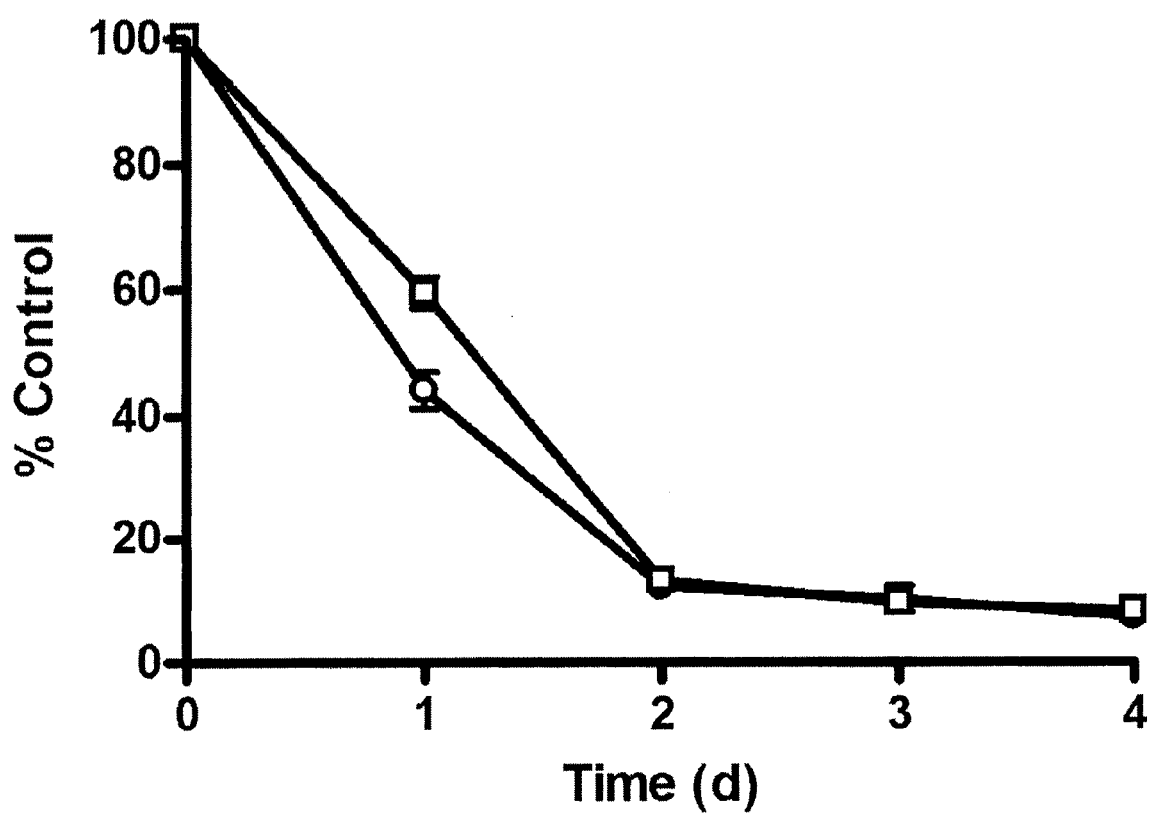
FIG. 1B depicts ASNS protein expression in the ovarian cell line OVCAR-3 following transfection of siASNS.1 (circle) or siASNS.2 (square) as percent of siNeg control as a function of time in days.
Figure 1C:
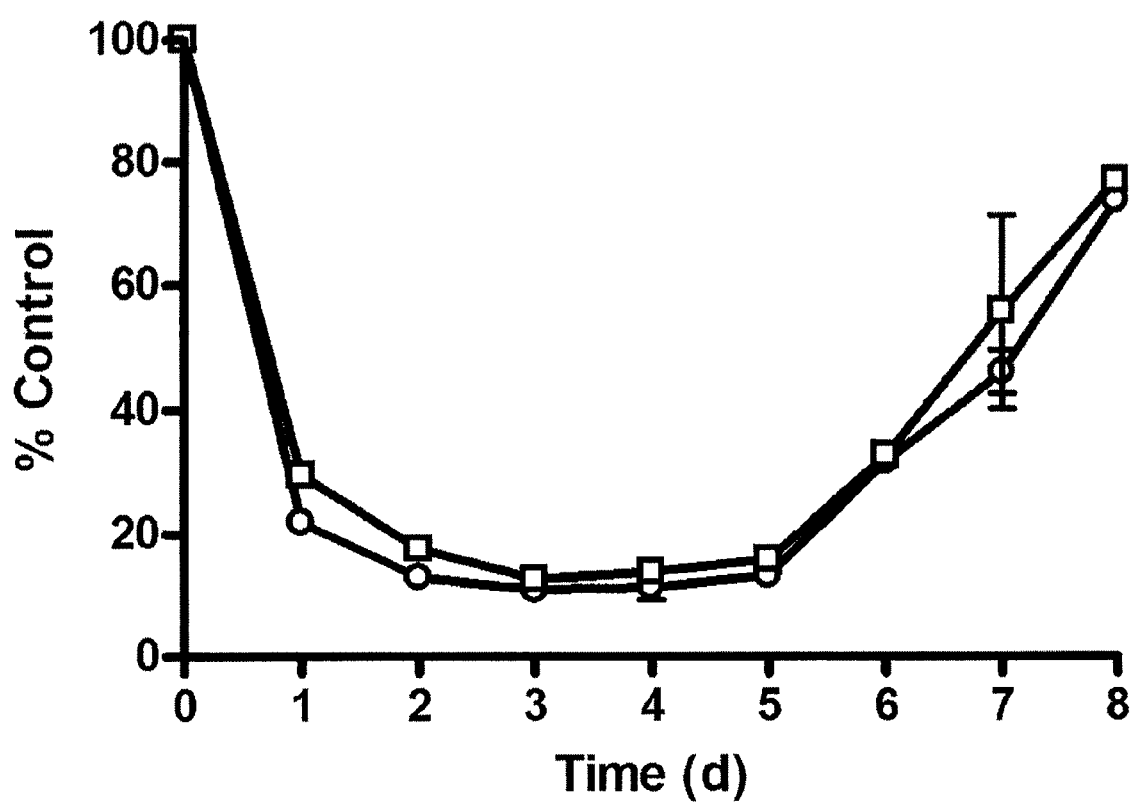
FIG. 1C depicts ASNS protein expression in the ovarian cell line OVCAR-8 following transfection of siASNS.1 (circle) or siASNS.2 (square) as percent of siNeg control as a function of time in days.

To analyze the time course of ASNS protein expression following RNAi, lysates prepared from siRNA-transfected OVCAR-4, OVCAR-3 and OVCAR-8 cells are subjected to quantitative Western blotting using a polyclonal rabbit anti-human ASNS antibody, this polyclonal antibody is directed against an epitope that includes the four amino acid sequence Thr-Asp-Pro-Ser (TDPS) (SEQ ID NO: 16). Both siRNAs yield a similar magnitude and duration (4-5 days) of ASNS silencing (FIGS. 1A, 1B, and 1C). That 4- to 5-day period provides a window of time for pharmacological experiments. Time course of protein expression is quantitated from Western blots after transfection of siASNS.1 (circles) or siASNS.2 (squares), expressed as percent of the corresponding siNeg control level. ASNS protein levels in all three of the siRNA-treated cell lines exhibit the same trend as that of mRNA, and these protein levels remain silenced throughout the time frame of pharmacological assays. The half-life of ASNS as measured by protein recovery in ASNS-silenced OVCAR-8 cells is 34±1 h (FIG. 1C). ASNS protein is assessed over eight days in the OVCAR-8 cell line to confirm that the transfection is transient; protein levels return to near-control levels by day 8.

Example 4

This example and those that follow demonstrate the ability of an ASNS antagonist, e.g., siRNA, to synergistically enhance the efficacy of L-ASP in decreasing undesirable cell proliferation, e.g., in ovarian cell lines. L-ASP activity can be aspirated and 120 μL MTS-containing medium added according to the manufacturer's protocol (Promega #G3580, Madison, Wis.). The plates are incubated at 37° C. and read at 490 nm between 1 and 4 hours.

Initially using GraphPad Prism 4.02, drug concentrations can be log transformed and nonlinear regression applied to the $A_{490}$ data using the sigmoidal dose response model with variable slope. Mean $EC_{50}$ values, standard errors, and 95% confidence intervals are determined from the logistic fits.

ASNS mRNA is silenced by RNAi in three ovarian cell lines. Two synthetic small interfering RNAs (siRNAs) corresponding to ASNS (siASNS.1 and siASNS.2) are transfected into OVCAR-4, OVCAR-3 and OVCAR-8. The branched-DNA assay indicates that the former two cell lines express relatively high levels of ASNS mRNA, while OVCAR-8 express the least. FIGS. 2A-2C and Table 4 shows the results for branched-DNA (RNA) assay for normalized ASNS mRNA 48 hours after transfection of siNeg, siASNS.1, or siASNS.2. A branched-DNA (RNA) assay for mRNA expression indicated that OVCAR-3 and OVCAR-4 express approximately 3.5 and 3 times as much ASNS mRNA as do OVCAR-8 cells. Forty eight hours following transfection of siASNS.1 or siASNS.2, ASNS mRNA levels are reduced by approximately 83% or 79% in OVCAR-4, 81% or 76% in OVCAR-3, and 87% or 80% in OVCAR-8 cells relative to transfection of the control siRNA (siNeg). Effect of RNAi against ASNS on L-ASP activity.

TABLE 4

| FIG # | Cell Line | siRNA used | non-variable slope model mean $EC_{50}$ (U/mL) | variable slope model mean $EC_{50}$ (U/mL) | non-variable slope model Mean Potentiation "synergism" (-fold difference) | variable slope model Mean Potentiation "synergism" (-fold difference) |
|---|---|---|---|---|---|---|
| 2A | OVCAR-4 | siNeg | 5.75 | 6.35 | — | — |
| | | siASNS.1 | 1.00 | 1.31 | 5.8 | 4.9 |
| | | siASNS.2 | 1.07 | 1.54 | 5.4 | 4.1 |
| 2B | OVCAR-3 | siNeg | 0.90 | 0.87 | — | — |
| | | siASNS.1 | 0.22 | 0.20 | 4.1 | 4.3 |
| | | siASNS.2 | 0.28 | 0.27 | 3.2 | 3.2 |
| 2C | OVCAR-8 | siNeg | 0.41 | 0.45 | — | — |
| | | siASNS.1 | 0.00071 | 0.00074 | 580 | 610 |
| | | siASNS.2 | 0.00077 | 0.00079 | 530 | 570 |
| 3 | OVCAR-8 (after ASNS reconst.) | siNeg | 0.95 | 0.99 | — | — |
| | | siASNS.1 | 1.05 | 1.09 | 0.9 | 0.9 |
| | | siASNS.2 | 0.93 | 0.98 | 1.0 | 1.0 |
| 4 | OVCAR-8/ADR | siNeg | 0.14 | 0.19 | — | — |
| | | siASNS.1 | 0.00023 | 0.00027 | 610 | 710 |
| | | siASNS.2 | 0.00023 | 0.00027 | 610 | 710 | directly associated with ASNS expression in ovarian cell lines via a negative correlation. The results in this example are consistent with those shown in the other Examples. The results further demonstrate that ASNS expression can serve as a biomarker for prediction of ovarian cancer sensitivity to L-ASP as well as the utility of therapies employing pegylated L-ASP. L-ASP activity is potentiated in all three cell lines following RNAi, for example.

For the MTS proliferation assay, the following materials and methods are employed. L-ASP activity is determined by measuring formazan production from MTS (Promega, Madison, Wis.), with drug concentrations tested in triplicate in each experiment. Serial dilutions of E. coli asparaginase (stock 500 U/mL in molecular biology grade $H_2O$; Sigma #A3809, St. Louis, Mo.) are prepared in medium at room temperature. At 48 hours after seeding, cells are washed by aspiration of the supernatant, and 150 μL of drug-containing medium is added. Another 48 hours later, the drug solution is The three ovarian cell lines are transfected with siRNA targeted to ASNS mRNA, administered L-ASP two days later, and measured L-ASP activity with an MTS-based cytotoxicity assay after two or three days (48-72 hours) of exposure to the enzyme. The baseline sensitivities of the three lines to L-ASP in the MTS assay (as assessed in siNeg-transfected cells) are consistent with previous results obtained using a sulforhodamine B assay in the NCI-60 screen [Scherf, U. et al., Nat Genet. 24, 236-44 (2000); Alley, M. C. et al., Cancer Res. 48, 589-601 (1988)]; OVCAR-4 shows the greatest resistance to L-ASP, and OVCAR-8 the greatest sensitivity (FIGS. 2A-2C). Transfection of OVCAR-4 cells with siASNS yields 4.1- to 4.9-fold potentiation of L-ASP activity. This result indicates that ASNS RNAi can affect drug response even in the presence of relatively high ASNS levels. OVCAR-3 cells, which express slightly less ASNS, yield a similar degree of L-ASP potentiation, 3.2- to 4.3-fold. The potentiation in both OVCAR-4 and OVCAR-3 is roughly proportional to the observed degree of ASNS silencing, which is 4- to 5-fold. The low-ASNS OVCAR-8 cells potentiate L-ASP more than 500-fold, an extent far greater than the ~5-fold ASNS silencing. That potentiation is highly reproducible; a second, independent experiment yields 560- and 550-fold potentiation with siASNS.1 and siASNS.2, respectively. These results demonstrate a causal link between ASNS expression and sensitivity to L-ASP in ovarian cancer cell lines. The link is clear-cut over a wide range of ASNS expression. The degree of potentiation in OVCAR-4 and OVCAR-3 cells is consistent with degree of ASNS knockdown (4- to 5-fold). That same level of ASNS knockdown in OVCAR-8 cells, on the other hand, which express the least ASNS of the three lines tested, yield >500-fold potentiation.

Accordingly, the combination of L-ASP and ASNS mRNA targeted siRNA synergistically decreases proliferation in all three cell types: OVCAR-4, OVCAR-3, and OVCAR-8. This synergism is individually true regardless of whether siASNS.1 or siASNS.2 is employed, and presumably holds true for other effective siRNAs as well. These results are representative of a general phenomenon of a synergistically increased efficacy of L-ASP in decreasing cell proliferation by use of ASNS targeted siRNA. These results can hold true not just for these three ovarian cell lines, but also for ovarian cancer cells generally and cancer and other proliferative-disease cells generally. This synergistic relationship holds true even if siRNA treatment alone has no substantial effect on cell proliferation. Measurements and calculations of synergism can be performed as described in Teicher, "Assays for In Vitro and In Vivo Synergy," in Methods in Molecular Medicine, vol. 85: Novel Anticancer Drug Protocols, pp. 297-321 (2003).

Example 5

This example demonstrates the reconstitution of ASNS expression abrogates L-ASP potentiation. OVCAR-8 resistance to L-ASP is completely reconstituted by nine days after the initial siRNA transfection, indicating that ASNS expression has returned to its natural level. Time course studies show that baseline ASNS expression as well as resistance to L-ASP are completely reconstituted within ten days after siRNA transfection, indicating that the observed potentiation is specifically associated with decreased ASNS levels.

To test for reversibility of the potentiation, L-ASP activity is assayed after ASNS protein has returned to near-baseline levels eight days after siASNS transfection. The cells are exposed to L-ASP for two days starting on day 8. Results are shown in Table 4. The MTS assay on day 10 indicates that the previously observed 500-fold potentiation had been abolished upon reconstitution of ASNS expression. OVCAR-8 cells exposed to L-ASP starting on day 8 after the transient siRNA transfection (i.e., when ASNS levels had returned essentially to baseline) and assayed with MTS on day 10. Resistance to L-ASP is reconstituted following transient transfection of ASNS siRNA. Silencing of ASNS potentiates activity of L-ASP in ovarian cell lines. To assess the relationship between ASNS and L-ASP-mediated cytotoxicity, the effect of the aforementioned silencing of ASNS in ovarian cell lines on L-ASP activity in an MTS-based cell proliferation assay is tested. Baseline sensitivity to L-ASP is measured by control (siNeg). OVCAR-4 shows the highest resistance to L-ASP and OVCAR-8 the highest sensitivity (FIGS. 2A-2C, 3). siASNS transfection of OVCAR-4 cells yields 5.2- to 5.5-fold potentiation of L-ASP activity, pointing to an effect on tumor growth even in the presence of relatively high ASNS levels. OVCAR-3 cells, which express slightly less ASNS, yield a similar degree of L-ASP potentiation, 3.3- to 4.1-fold. OVCAR-8 cells exhibit the greatest L-ASP potentiation following ASNS RNAi—greater than 500-fold; a potentiation that is highly reproducible. These results demonstrate a direct relationship between ASNS expression and sensitivity to L-ASP in ovarian cancer cell lines.

Transfection of siRNA targeted to ASNS yields substantial silencing of both mRNA and protein (Tables 2A-2C; FIGS. 1A-1C), and that silencing yields potentiation of L-ASP activity in all three ovarian cell lines tested (FIGS. 2A-2C, 3). Although the degree of potentiation in OVCAR-4 and OVCAR-3 cells is consistent with the degree of ASNS knockdown (4- to 5-fold), that same level of ASNS knockdown in OVCAR-8 cells, on the other hand, yields greater than 500-fold potentiation. L-ASP activity can be exponentially potentiated to the point of being synergistic. Because siRNA targeted to ASNS in the absence of L-ASP does not affect the proliferation/metabolic activity of any of the tested cell lines (compared to un-transfected cells), the potentiation that results from combination with L-ASP qualifies as synergistic. The combination index (CI) is calculated for all three cell lines using CalcuSyn software. The resulting CI is below 1.0 for all three cell lines, confirming that the combination of siASNS and L-ASP is synergistic.

The correlation between ASNS expression (Tables 2A-2C; FIGS. 1A-1C) and L-ASP activity in the tested ovarian cell lines OVCAR-4, OVCAR-3, and OVCAR-8 (FIGS. 2A-2C, 3, and Table 4) is relatively low, r=0.56. Use of these three cell lines is advantageous because they exhibit the lowest levels of toxicity upon siNeg transfection. ASNS is identified as a dominant predictor of L-ASP activity in leukemic and ovarian subsets of the NCI-60 cell lines. The role of other genes on the predictive value of ASNS on L-ASP activity can also be examined. For example, since OVCAR-3 expresses AKT2 at levels 4- and 8-fold greater than OVCAR-4 and OVCAR-8, AKT2 expression, if it were involved in the mechanism of L-ASP activity, can be looked at for as to why OVCAR-3 sensitivity to L-ASP is slightly greater than expected based on ASNS expression alone. Learner of Functional Enrichment (LeFE) is an algorithm that can be used to rank genes in order of significance for L-ASP activity.

This example, along with Example 4 and the other examples provided, demonstrates the power of pharmacogenomic data analysis and a direct relationship between ASNS protein expression and L-ASP efficacy in three ovarian cell lines. The results demonstrate that ovarian tumors with moderate to low levels of ASNS can be sensitive to depletion of extracellular asparagine, and further support the rationale for clinical testing of L-ASP in a subset of ovarian cancer patients.

Example 6

This example demonstrates that L-ASP activity is potentiated by siRNA targeted to ASNS in a multidrug-resistant cell line, and that L-ASP can be effective in ovarian cancers with low to moderate ASNS despite evidence of chemotherapeutic resistance. This demonstration is significant as the majority of ovarian cancer patients develop resistance to chemotherapeutics. OVCAR-8/ADR, also known as NCI-ADR-RES, is an OVCAR-8 variant, which is selected for pleiotropic drug resistance by chronic exposure to Adriamycin (doxorubicin). [Batist, G. et al., J Biol Chem 261, 15544-9 (1986); Cowan, K. H., et al., Proc Natl Acad Sci USA 83, 9328-32 (1986).] ASNS levels in NCI-ADR-RES cells are similar to those of the parental OVCAR-8, precluding ASNS upregulation as part of the pleiotropic response to anticancer agents such as Adriamycin. As observed with OVCAR-8, NCI-ADR-RES cells demonstrate >500-fold potentiation of L-ASP activity upon 80-90% ASNS knockdown. Representative single experiments are shown. L-ASP activity is potentiated greater than 700 or 800-fold following ASNS silencing in NCI-ADR-RES cells (Table 4; FIG. 4).

ASNS expression in OVCAR-8/ADR is approximately the same as in the parental OVCAR-8 cell line, suggesting that acquisition of multidrug drug resistance does not affect ASNS expression. Significantly, siASNS transfection yields more than 700-fold potentiation of L-ASP activity in OVCAR-8/ADR cells (Table 4; FIG. 4), demonstrating that the causal link between ASNS expression and L-ASP activity survives the development of classical multidrug resistance. That potentiation is reproducible; a second, independent experiment yields 840- and 880-fold potentiation with siASNS.1 and siASNS.2, respectively. Accordingly, the potentiation of siRNA on L-ASP for decreasing cell proliferation is synergistic for OVCAR-8/ADR cells. This synergism is individually true regardless of whether siASNS.1 or siASNS.2 is employed, and presumably holds true for other effective siRNAs as well. These results are representative of a general phenomenon of a synergistically increased efficacy of L-ASP in decreasing cell proliferation by use of ASNS targeted siRNA. These results can hold true not just for OVCAR-8/ADR cells, but also for ovarian cancer cells generally and cancer and other proliferative-disease cells generally. This synergistic relationship holds true even if siRNA treatment alone has no substantial effect on cell proliferation. Measurements and calculations of synergism can be performed as described in Teicher, "Assays for In Vitro and In Vivo Synergy," in Methods in Molecular Medicine, vol. 85: Novel Anticancer Drug Protocols, pp. 297-321 (2003). Synergism can also be confirmed by calculating the CI using CalcuSyn Software.

Example 7

This example demonstrates the that ASNS antibody stains ovarian cell lines differentially in accord with microarray and Western blot data described in the other examples. ASNS levels are assessed by immunohistochemical staining of ovarian cell lines with a rabbit polyclonal antibody. Images obtained are consistent with the findings from multiple microarray platforms; OVCAR-3 and OVCAR-4 express relatively high levels of ASNS, whereas OVCAR-5 expresses less, and OVCAR-8 expresses the least (40×/0.75 and 100×/1.30 objectives). Immunohistochemical staining using a rabbit polyclonal antibody against ASNS exhibits differential staining of the ovarian cell lines. The order of staining intensities is OVCAR-4>OVCAR-3>OVCAR-5>OVCAR-8, consistent with the relative expression levels determined for ASNS mRNA by microarray in Example 1, by branched-DNA assay, and for ASNS protein by Western blot in Example 3. In each culture, all cells stain to about the same intensity. For cell pellet immunohistochemistry, cultured ovarian cells are harvested and clotted with thrombin (thrombin, Topical USP). After fixation in 10% formalin, cells are embedded in paraffin and 5 µm sections are cut. Deparaffinized slides are placed in 10 mM citrate buffer pH 6.0 containing 0.1% Tween-20, and heat-induced antigen retrieval is performed using a microwavable pressure cooker (Nordicware, Minneapolis, Minn.) under maximum heat and pressure for 20 minutes. Following antigen retrieval, the slides are incubated with a rabbit polyclonal, affinity-purified antibody produced against asparagine synthetase (1:3000). Signal is detected using an automated immunostainer (Dako-Cytomation, Carpinteria, Calif.) and an HRP/DAB polymer-based rabbit antibody detection system (Envision+, DakoCytomation) according to the manufacturer's recommendations. Images are visualized under an Olympus BX41 microscope equipped with an Olympus UPlan Fl 20×/0.5 (∞/0.17), captured with an Olympus DP12 digital camera, and processed with Photoshop 6.0 software (Adobe Systems, San Jose, Calif.). Ovarian tumor tissue arrays show a broad range of ASNS staining intensities.

Example 8

The example demonstrates the detection of clinical cancers low in ASNS using tissue array screening with immunohistochemistry. To begin assessment of the potential of ASNS as a biomarker in clinical tumors, ASNS expression is examined in a variety of cancer types using tissue microarrays from the NCI Tissue Array Research Program (TARP) [Kononen, J. et al. Tissue microarrays for high-throughput molecular profiling of tumor specimens. Nat Med 4, 844-7 (1998)]. For qualitative analysis, each tumor specimen is scored as 0, 1+, 2+, or 3+ depending on the intensity (negative, weak, moderate, strong) and pervasiveness of staining. For heuristic purposes, 0 and 1+ are considered "low." ASNS levels are scored as low in 15% (8/54) of ovarian cancers, 2% (1/46) of prostate cancers, 17% (6/35) of breast cancers, 19% (12/63) of colon cancers, 23% (18/77) of lung cancers, 55% (12/22) of lymphomas, and 64% (7/11) of head and neck tumors. Intensity of staining for any particular tumor core can be influenced by the way in which the core is fixed and embedded. The cut-off at 1+ staining is arbitrary; other cut-offs can also be used. Comparison of tumor types is performed and information obtained from that comparison. Lymphomas show a greater percentage of low-expressors. 64% of head and neck tumors are found unexpectedly to be low-expressors. At the other end of the spectrum are the prostate cancers; ovarian are found to be near the middle. In one embodiment, 15% of ovarian cancers are responsive to L-ASP on the basis of low ASNS, responders are identified in a clinical trial of moderate size using ASNS as a biomarker for patient selection or in analysis of the responses. TARPS-T-BO-1, T-CL-1, and MTA-5 tumor tissue microarrays, produced as previously described [Hewitt, S. M., Methods Mol Biol 264, 61-72 (2004)], are obtained from the NCI Tissue Array Research Program (TARP). Sections (5 µm) are cut from the array blocks using tape sectioning materials from Instrumedics (Hackensack, N.J., USA). Immunohistochemical staining is performed as described for the cell blocks as described in Example 7, with the exception that two antibody dilutions are used (1:1500 and 1:3000). Staining intensity is graded on an arbitrary four-point scale: 0, no staining; 1+, faint or weak staining; 2+, moderate staining; and 3+, strong staining. Only intact cores containing tumor cells are scored.

The TARPS-T-BO-1 array can contain 54 scoreable ovarian cancers and 35 scoreable breast cancers. The T-CL-1 array can contain 63 scoreable colon cancers and 77 scoreable lung cancers. The MTA-5 array can contain 46 scoreable prostate cancers, 22 scoreable lymphomas, and 11 scoreable head and neck tumors. The tissue microarray from Cybrdi, Inc. (catalogue #CC11-01-002) includes 69 ovarian cancers and 3 normal ovarian samples (all scoreable) and the array from US BioMax, Inc. (catalogue #OV2001) contains 173 primary ovarian cancers (172 scoreable) and 8 normal ovarian samples. Tissue microrrays are scanned with an Epson perfection 4800 scanner; individual core images are visualized as described for cell blocks.

Studies can also be performed with ovarian cancer tissue arrays from Cybrdi, Inc. (60 primary ovarian tumors) and US Biomax (172 primary ovarian tumors). Six and seven percent, respectively, of the ovarian cancers are arbitrarily scored as low-expressers, but no other tumor types are present for comparison. A range of staining intensity can be observed, and that intensity can be essentially uniform across all tumor cells in a given core. When ASNS levels in an ovarian cancer tissue microarray are detected immunohistochemically using a rabbit polyclonal antibody, an overview scan of US Biomax array of squamous cell tumors can be performed. Magnification (10×/0.3 objective) of images of ASNS-positive and ASNS-negative cores can be performed. Higher-magnification (40×/0.75 objective) images of respective cores can also be performed. Other arrays that can be employed include a head and neck cancer array such as the Cybrdi's head and neck squamous carcinoma (multi-sites, grade I-III) tissue arrays CC34-01-001, and a pancreatic cancer array such as Cybrdi's Pancreatic carcinoma (Duct adenocarcinoma/islet cell carcinoma/mucinous carcinoma) with normal controls tissue arrays CC14-01-002.

Cybrdi's head and neck squamous carcinoma (multi-sites, grade I-III) tissue arrays CC34-01-001 contains the following kinds of cancers (including various grades thereof): squamous cell carcinoma of cheek part, squamous cell carcinoma of tongue, squamous cell carcinoma of larynx, squamous cell carcinoma of upper jaw, squamous cell carcinoma of nasopharynx, mucitis of gingival, mucosa tissue of gingival, and mucitis of gingival. Cybrdi's Pancreatic carcinoma (Duct adenocarcinoma/islet cell carcinoma/mucinous carcinoma) with normal controls tissue arrays CC14-01-002 contains the following kinds of cancers (including various grades thereof): duct adenocarcinoma, islet cell carcinoma, mucus and disintegrative tumor cell, mucinous adenocarcinoma, fibrous tissue and fatty tissue, chronic pancreatitis, and papillary duct adenocarcinoma. Cybrdi's Ovary carcinoma (adenocarcinoma, serous, endometrial, clear cell, small cell, granular cell, etc.) with normal ovary tissue controls tissue arrays CC11-01-002 contains the following kinds of cancers (including various grades thereof): endometrioid adenocarcinoma, serous papillary adenocarcinoma, clear cell carcinoma, serous adenocarcinoma, serous papillary adenocarcinoma with necrosis, granular cell tumor, dysgerminoma, Krukenberg's tumor, metastatic adenocarcinoma, malignant Brenner tumor, squamous cell carcinoma, endodermal sinus tumor, mucous papillary adenocarcinoma, metastatic adenocarcinoma with necrosis, malignant theca cell tumor, mucinous adenocarcinoma, metastatic adnocarcinoma, undifferentiated carcinoma, granular cell tumor, A little carcinoma tissue. Biomax's OV2001 Ovarian cancer high-density (200 core) tissue array contains the following kinds of cancers (including various grades thereof): mucous papillary adenocarcinoma, mucous papillary adenocarcinoma with necrosis, serous papillary adenocarcinoma, serous papillary adenocarcinoma with necrosis, borderline serous tumor, endometrioid adenocarcinoma, endometrioid adenocarcinoma with squamous metaplasia, endometrioid adenocarcinoma, A little serous papillary adenocarcinoma, transitional cell carcinoma, tumoral necrosis, serous papillary adenocarcinoma with lymphocytes infiltration, metastatic signet-ring cell carcinoma, metastatic undifferentiated adenocarcinoma, metastatic mucous adenocarcinoma, metastatic adenocarcinoma, mucous secretion, and metastatic mucous adenocarcinoma. The various arrays can also contain healthy tissues.

Example 9

This example demonstrates the effect of ASNS expression on resistance of melanoma cells to L-Asparaginase (L-ASP), and that the effect of RNAi and L-ASP is synergistic. ASNS expression is shown to be causally linked to L-ASP activity in these melanoma cells. For the experiment, UACC-257 cells can be employed. The efficacy ($EC_{50}$) of L-ASP in control vs. ASNS-silenced (via RNAi) UACC-257 cells is quantitated. Silencing in UACC-257 cells is optimized at 0.025 µL siRNA (5 nM), 0.75 µl Oligofectamine (Invitrogen, Carlsbad, Calif.), and 4200 cells/well (100 µL medium). A 48 hour RNAi treatment can be employed followed by 48 hour L-ASP treatment (3-fold dilutions). [L-ASP] concentrations in U/mL indicated for two plates (siNeg, siASNS.1 and siASNS.2 as described in Example 2) are employed, e.g., a series of concentrations of 10.0, 4.5, 2.1, 0.9, 0.43, 0.19, 0.088, 0.040, 0.018 for siNeg; and 1.0, 0.25, 0.06, 0.016, 0.0039, 0.0010, 0.00024, 0.00006, and 0.000015 for siASNS.1 and siASNS.2.

All cells are routinely maintained in RPMI-1640 (BioWhittaker) containing 5% fetal bovine serum (FBS) and 1% (2 mM) L-glutamine (Invitrogen, Carlsbad, Calif.). Cultures are grown in an atmosphere of 5% $CO_2$ and 90% relative humidity at 37° C. For cell plating, the siRNAs and Oligofectamine are gathered on ice, and R0 and R10 media at room temp. For the three siRNA preparations, three microfuge and three 50 mL tubes are used to prepare the transfection complexes. Into one microfuge tube per siRNA, is added 3×14×25 µL=1050 µL, R0 medium (RPMI-1640, NO Gln or FBS), then 3×14×0.025 µL=1.05 µL appropriate siRNA tube and mixed. Same volume of R0 medium is added to a complimentary 50 mL Falcon tube followed by 3×14×0.75 µL=31.5 µL Oligofectamine and gently mixed. Each siRNA tube is combined with complimentary lipid tube and incubated 45 min at room temp (3 tubes total now).

Meanwhile, one 80-90% confluent T-75 flask of UACC-257 cells is aspirated and washed twice with PBS, then trypsinized, neutralized, clarified and resuspended in 5 mL of R10 medium (RPMI-1640, 2% Gln, 10% FBS). Cells are counted with a hemacytometer and trypan blue yielding 0.58×10$^6$ cells/mL. If 869 µL of this suspension yields the requisite 4200 cells/well×120 wells (overestimate)=0.504×10$^6$ cells total, 869 µL of the cell suspension are brought to 120 wells×50 µL/well=6.0 mL with R10 medium. Using a pipettor that does not create air bubbles, 50 µL of R0/siRNA suspension is added to appropriate wells of the two 96-well plates, followed by 50 µL of the R10/cell suspension. Transfections mediated by cationic lipid are performed in the 96-well plates. Cells are seeded on a complex of the appropriate siRNA (Qiagen Inc., Germantown, Md.) and Oligofectamine (Invitrogen, Carlsbad, Calif.) in unsupplemented RPMI-1640. The plates are incubated 45 min at room temp, then moved to an incubator. Incubation occurs for 48 hours before drug treatment. At 48 hours, serial dilutions of *E. coli* asparaginase (stock 500 U/mL in molecular biology grade $H_2O$; Sigma #A3809, St. Louis, Mo.) is prepared in medium from lyophilized powder immediately prior to use for n=12 (n=15 for calculations) as shown in Table 5.

TABLE 5

| [L-ASP] (U/mL) | V prev. line (μL) | +medium (μL) | V total (μL) | [L-ASP] (U/mL) | V prev. line (μL) | +medium (μL) | V total (μL) |
|---|---|---|---|---|---|---|---|
| 10 | — | — | — | 500 | — | — | — |
| 1 | 140.0 | 1260.0 | 1400.0 | 10 | 24.8 | 1214.3 | 1239.1 |
| 0.25 | 350.0 | 1050.0 | 1400.0 | 4.54545 | 499.1 | 598.9 | 1098.0 |
| 0.0625 | 350.0 | 1049.9 | 1399.9 | 2.06612 | 498.0 | 597.6 | 1095.6 |
| 0.01563 | 349.9 | 1049.7 | 1399.7 | 0.93914 | 495.6 | 594.7 | 1090.3 |
| 0.00391 | 349.7 | 1049.0 | 1398.6 | 0.42688 | 490.3 | 588.4 | 1078.7 |
| 0.00098 | 348.6 | 1045.9 | 1394.5 | 0.19404 | 478.7 | 574.4 | 1053.0 |
| 0.00024 | 344.5 | 1033.6 | 1378.1 | 0.0882 | 453.0 | 543.7 | 996.7 |
| 6.1E−05 | 328.1 | 984.4 | 1312.5 | 0.04009 | 396.7 | 476.0 | 872.7 |
| 1.5E−05 | 262.5 | 787.5 | 1050.0 | 0.01822 | 272.7 | 327.3 | 600.0 |
| 0 | — | 1050.0 | 1050.0 | 0 | — | 600.0 | 600.0 | siRNA-transfected cells are aspirated and 150 μL of drug solution is added (concentrations indicated in Table 5). Incubation then occurs for 48 hours. The drug solution is aspirated and 120 μL of [100 μL fresh media+20 μL MTS] (Promega #G3580, Madison, Wis.) is added to each of the cell containing wells. Each plate is incubated at 37° C., then the plate is read at 490 nm directly from incubator to keep media as close to 37° C. as possible. Readings are taken at 1 and 1.5 hours to determine optimal development time.

GraphPad Prism 4.02 is used to log transform drug concentrations (x-values). Nonlinear regression is applied to that data using the sigmoidal dose response model with variable slope. Mean $EC_{50}$ values are shown with error determined from the 95% Confidence Interval. Fitting employs the biphasic dose-response model in Prism, and initial estimates of the $LogEC_{50}$ are supplied (−3.9 for $LogEC_{50}1$ and −0.6 for $LogEC_{50}2$). Best fit $EC_{50}$ for siNeg is 0.1731 U/mL. For siASNS.1 and siASNS.2, $EC_{50}1$ is 0.000151 and 0.0000971 U/mL, and $EC_{50}2$ is 0.23 and 1.40 U/mL. The results are shown in FIG. 5A. The 1.40 U/mL is the result of sub-optimal fitting due to limited data. The second $EC_{50}$ is near siNeg, because whatever component is responsible for that phase of the curve is not silenced. Comparing $EC_{50}1$ to the $EC_{50}$ for siNeg reveals that silencing ASNS yielded 1100- and 1800-fold potentiation of L-ASP.

The experiment is repeated and GraphPad Prism 4.02 is again used to log transform drug concentrations (x-values). Nonlinear regression is applied to that data using the sigmoidal dose response model with variable slope. Mean $EC_{50}$ values are shown with error determined from the 95% Confidence Interval. Fitting employs the biphasic dose-response model in Prism, and initial estimates of the $LogEC_{50}$ are supplied (−4.0 for $LogEC_{50}1$ and −0.66 for $LogEC_{50}2$). Best fit $EC_{50}$ values are shown in Table 15-0.25 U/mL for siNeg, and 0.000081 for both siASNS.1 and siASNS.2. The individual data points are shown in FIG. 5B as well as in Table 6. In siASNS-transfected cells, the second $EC_{50}$ is near siNeg, because whatever component is responsible for that phase of the curve is not silenced. Comparing $EC_{50}1$ to the $EC_{50}$ for siNeg reveals that silencing ASNS yielded 3100- and 3100-fold potentiation of L-ASP (also indicated in Table 15).

TABLE 6

UACC-257 (si values are $A_{490}$)

| log[L-ASP] | siNeg | siASNS.1 | siASNS.2 |
|---|---|---|---|
| 1 | 0.424 | 0.280333 | 0.305667 |
| 0.657577 | 0.43366667 | 0.295 | 0.319 |
| 0.315155 | 0.48133333 | 0.470333 | 0.514 |
| −0.02727 | 0.52533333 | 0.667 | 0.72 |

TABLE 6-continued

UACC-257 (si values are $A_{490}$)

| log[L-ASP] | siNeg | siASNS.1 | siASNS.2 |
|---|---|---|---|
| −0.36969 | 0.78933333 | 0.684333 | 0.779667 |
| −0.71211 | 1.22233333 | 0.741 | 0.804667 |
| −1.05454 | 1.66466667 | 1.279333 | 1.388 |
| −1.39696 | 1.72366667 | 1.782 | 1.866667 |
| −1.73938 | 1.706 | 1.812 | 1.816 |

The effect of RNAi on ASNS expression is also examined using an in-cell Western analysis of ASNS protein demonstrating the efficacy of ASNS antagonists, e.g., siRNA, and the ability of ASNS siRNA to silence ASNS. This analysis is performed in a manner analogous to that described in Example 3. Cells are transfected with siNeg or siASNS.1, incubated for 48 hours, treated with vehicle-only or the $EC_{50}$ dose of L-ASP for 48 hours, then assessed for ASNS protein expression by in-cell Western assay. ASNS levels for three replicate samples are normalized to total DNA content of that sample, background-corrected, and finally expressed as percent of siNeg-transfected control for that cell line. If the rabbit polyclonal ASNS antibody employed exhibits high specificity for ASNS compared to non-specific rabbit IgG in western blotting applications, the Li-Cor Odyssey In-Cell Western protocol (Document #988-08339; Li-Cor Biosciences, Lincoln, Nebr.) can be used to detect ASNS protein levels with the following modifications. One manner of setting up wells is as follows: 1=rabbit IgG (to assess specificity of primary antibody), 2=WT, 3=siNeg, 4=siASNS, 5=siNeg+L-AS-$P_{EC50}$, 6=siASNS+L-ASP$_{EC50}$ (L-ASP~$_{EX90}$ for UACC-257), 7=siASNS+L-ASP$_{EC50}$ for UACC-257. The primary antibody is rabbit anti-hASNS used at 2.0 μg/mL, and non-specific rabbit IgG is used at 2.0 μg/mL for assessment of background. The secondary antibody solution contains goat anti-rabbit IR Dye 800CW (Rockland, Gilbertsville, Pa.) and TO-PRO-3 iodide (Invitrogen) at 1:600 and 1:1000, respectively. For data analysis, ASNS levels for a given sample are first normalized to total DNA levels for that sample as measured by TO-PRO-3 iodide, then background-corrected, and finally expressed as percent of siNeg-transfected control. The in-cell Western ASNS data are shown in Table 7 with mean values and standard deviation (SD) of relative expression determined by pixel density.

TABLE 7

| UACC-257 | siNeg + vehicle | siNeg + L-ASP | siASNS + vehicle | siASNS + L-ASP |
|---|---|---|---|---|
| mean | 100 | 333 | 95 | 88 |
| SD | 5 | 11 | 2 | 2 |

Accordingly, the potentiation of siRNA on L-ASP for decreasing cell proliferation is synergistic for UACC-257 cells. This synergism is individually true regardless of whether siASNS.1 or siASNS.2 is employed, and presumably holds true for other effective siRNAs as well. These results are representative of a general phenomenon of a synergistically increased efficacy of L-ASP in decreasing cell proliferation by use of ASNS targeted siRNA. These results can hold true not just for UACC-257 cells, but also for melanoma cells generally and cancer and other proliferative-disease cells generally. This synergistic relationship holds true even if siRNA treatment alone has no substantial effect on cell proliferation. Measurements and calculations of synergism can be performed as described in Teicher, "Assays for In Vitro and In Vivo Synergy," in Methods in Molecular Medicine, vol. 85: Novel Anticancer Drug Protocols, pp. 297-321 (2003). Synergism can also be confirmed by calculating the CI using CalcuSyn Software.

Example 10

This example demonstrates the effect of ASNS expression on resistance of renal cancer cells to L-Asparaginase (L-ASP), and that the effect of RNAi and L-ASP is synergistic. ASNS expression is shown to be causally linked to L-ASP activity in these renal cancer cells. For the experiment, SN12C cells can be employed. Procedures and calculations are analogous to that described in Example 9. Final amounts in each well of the 96 well plates can be 5 nM siRNA, 0.50 µL Oligofectamine, and 6,000 SN12C cells in 100 µL medium. The results are shown in FIG. 6 and Table 8. The effect of RNAi on ASNS expression can be examined using an in-cell Western analysis of ASNS protein as described in Example 9 to yield analogous results.

TABLE 8

SN12C (si values are $A_{490}$)

| log[L-ASP] | siNeg | siASNS.1 | siASNS.2 |
|---|---|---|---|
| 0.90309 | 0.51966667 | 0.546333 | 0.588667 |
| 0.30103 | 0.57033333 | 0.639667 | 0.79 |
| −0.30103 | 0.76833333 | 0.783667 | 0.866667 |
| −0.90309 | 1.14633333 | 0.662667 | 0.948 |
| −1.50515 | 1.212 | 0.768667 | 0.949667 |
| −2.10721 | 1.17966667 | 0.984333 | 1.135667 |
| −2.70927 | 1.228 | 1.442333 | 1.362333 |
| −3.31133 | 1.12433333 | 1.397333 | 1.283333 |
| −3.91339 | 1.046 | 1.322667 | 1.215 |

Accordingly, siRNA potentiates the L-ASP decrease in SN12C cell proliferation synergistically. This synergism is individually true regardless of whether siASNS.1 or siASNS.2 is employed, and presumably holds true for other effective siRNAs as well. These results are representative of a general phenomenon of a synergistically increased efficacy of L-ASP in decreasing cell proliferation by use of ASNS targeted siRNA. These results can hold true not just for SN12C cells, but also for renal cancer cells generally and cancer and other proliferative-disease cells generally. This synergistic relationship holds true even if siRNA treatment alone has no substantial effect on cell proliferation. Measurements and calculations of synergism can be performed as described in Teicher, "Assays for In Vitro and In Vivo Synergy," in Methods in Molecular Medicine, vol. 85: Novel Anticancer Drug Protocols, pp. 297-321 (2003). Synergism can also be confirmed by calculating the CI using CalcuSyn Software.

Example 11

This example demonstrates that the effect of ASNS expression on resistance of breast and brain cancer cells to L-Asparaginase (L-ASP), and that the effect of RNAi and L-ASP is synergistic. ASNS expression is shown to be causally linked to L-ASP activity in these cell types.

MTS assays analogous to those performed in Example 9 are performed on two breast cancer cells lines, MCF7 and MDA-MB-231, and a brain cancer (glioblastoma) cell line, SNB19 with slight variations. Final amounts in each well of the 96 well plates can be 5 nM siRNA, 0.70 µL Oligofectamine, and 5,000 MCF7 cells in 100 µL of medium; 30 nM siRNA, 0.70 µA Oligofectamine, and 3,500 MDA-MB-231 cells in 100 µL medium; 5 nM siRNA, 0.50 µL Oligofectamine, and 3,000 SNB-19 cells in 100 µL medium. Results are shown in FIGS. 7, 8, and 9 as well as Tables 9, 10, 11 for MCF7, MDA-MB-231 and SNB19 respectively. For FIGS. 7, 8, and 9, results are shown as siNeg (squares), siASNS.1 (triangles), or siASNS.2 (circles), for the cells incubated at 37° C. for 48 h, then treated with a range of L-ASP concentrations for 48 h, immediately followed by MTS assay.

TABLE 9

MCF7 (si values are $A_{490}$)

| log[L-ASP] | siNeg | siASNS.1 | siASNS.2 |
|---|---|---|---|
| 1 | 0.262 | 0.248333 | 0.247333 |
| 0.657577 | 0.62266667 | 0.235333 | 0.222333 |
| 0.315155 | 0.998 | 0.268333 | 0.282 |
| −0.02727 | 1.01733333 | 0.297333 | 0.307667 |
| −0.36969 | 1.004 | 0.378333 | 0.343 |
| −0.71211 | 1.098 | 0.461 | 0.408 |
| −1.05454 | 1.0775 | 0.725667 | 0.724667 |
| −1.39696 | 1.0935 | 0.863 | 0.94 |
| −1.73938 | 1.0355 | 0.998 | 0.87 |

TABLE 10

MDA-MB-231 (si values are $A_{490}$)

| log[L-ASP] | siNeg | siASNS.1 | siASNS.2 |
|---|---|---|---|
| 1.221849 | 0.262 | 0.169 | 0.162 |
| 0.443697 | 0.62266667 | 0.159667 | 0.164333 |
| −0.33445 | 0.998 | 0.174667 | 0.171333 |
| −1.11261 | 1.01733333 | 0.198333 | 0.206333 |
| −1.89076 | 1.004 | 0.205 | 0.207 |
| −2.66891 | 1.098 | 0.221333 | 0.216333 |
| −3.44706 | 1.0775 | 0.213667 | 0.227333 |
| −4.22521 | 1.0935 | 0.362667 | 0.382667 |

TABLE 11

SNB-19 (si values are $A_{490}$)

| log[L-ASP] | siNeg | siASNS.1 | siASNS.2 |
|---|---|---|---|
| 2 | 0.5715 | 0.407333 | 0.349 |
| 1 | 0.52566667 | 0.373667 | 0.2785 |
| 0 | 0.63166667 | 0.424333 | 0.444 |
| −0.39794 | 0.87266667 | 0.424333 | 0.441 |
| −1.1549 | 1.37966667 | 0.431 | 0.449 |
| −1.52288 | 1.40733333 | 0.521333 | 0.532 |
| −3.04576 | 1.50066667 | 0.6175 | 0.4815 |
| −3.45593 | 1.58633333 | 0.773333 | 0.7625 |
| −4.22185 | 1.452 | 1.354 | 1.4705 |

The effect of RNAi on ASNS expression is also examined using an in-cell Western analysis of ASNS protein, in a manner consistent with that described in Example 3, demonstrating the efficacy of ASNS antagonists, e.g., siRNA, and the ability of ASNS siRNA to silence ASNS. Results for MCF7 and SNB19 cells are shown in Tables 12 and 13 respectively with mean values and standard deviation (SD) of relative expression determined by pixel density. Results for similar analysis on OVCAR-8 cells are shown in Table 14 with mean values and standard deviation (SD) of relative expression determined by pixel density, confirming results in Example 3. This type of analysis can also be performed for MDA-MB-231 cells.

TABLE 12

| MCF7 | siNeg + vehicle | siNeg + L-ASP | siASNS + vehicle | siASNS + L-ASP |
|---|---|---|---|---|
| mean | 100 | 202 | 52 | 53 |
| SD | 2 | 8 | 2 | 3 |

TABLE 13

| SNB19 | siNeg + vehicle | siNeg + L-ASP | siASNS + vehicle | siASNS + L-ASP |
|---|---|---|---|---|
| mean | 100 | 490 | 69 | 112 |
| SD | 1 | 12 | 3 | 8 |

TABLE 14

| OVCAR-8 | siNeg + vehicle | siNeg + L-ASP | siASNS + vehicle | siASNS + L-ASP |
|---|---|---|---|---|
| mean | 100 | 251 | 37 | 84 |
| SD | 8 | 7 | 20 | 23 |

Accordingly, the potentiation of siRNA on L-ASP for decreasing cell proliferation is synergistic for MCF7, MDA-MB-231, and SNB19 cells. This synergism is individually true regardless of whether siASNS.1 or siASNS.2 is employed, and can hold true for other effective siRNAs as well. These results are representative of a general phenomenon of a synergistically increased efficacy of L-ASP in decreasing cell proliferation by use of ASNS targeted siRNA. These results can hold true not just for MCF7, MDA-MB-231, and SNB19 cells, but also for breast and brain cancer cells generally and cancer and other proliferative-disease cells generally. This synergistic relationship can hold true even if siRNA treatment alone has no substantial effect on cell proliferation. Measurements and calculations of synergism can be performed as described in Teicher, "Assays for In Vitro and In Vivo Synergy," in Methods in Molecular Medicine, vol. 85: Novel Anticancer Drug Protocols, pp. 297-321 (2003). Synergism can also be confirmed by calculating the CI using CalcuSyn Software.

Examples 9, 10, and 11 collectively demonstrate the ability of siRNA to potentiate the activity of L-ASP in a variety of different cancer cell types. In-cell Western assays for ASNS protein in siRNA-transfected MCF7 (breast cancer), SNB19 (glioblastoma), UACC-257 (melanoma), and OVCAR-8 (ovarian cancer) cells show that RNAi with siASNS yielded 48%, 31%, 5%, and 63% knockdown of baseline ASNS expression relative to the siNeg/vehicle-treated control, respectively. Treatment with siNeg and an $EC_{50}$ dose of L-ASP causes ASNS expression to be upregulated to 202%, 490%, 333%, and 151% of siNeg/vehicle-treated control, respectively. ASNS levels in cells treated with siASNS and an $EC_{50}$ dose of L-ASP, however, are 53%, 112%, 88%, and 84% of siNeg/vehicle-treated control, respectively. These data indicate that L-ASP treatment causes ASNS upregulation in all tissue types, siASNS treatment prevented much of that upregulation, and in most cell lines RNAi was able to overpower the L-ASP-induced upregulation of ASNS. Analogous in-cell Western assays can be performed using MDA-MB-231 (breast cancer) and SN12C (renal cancer) cell lines.

Examples 9, 10, and 11 also demonstrate that ASNS expression is causally linked to L-ASP activity in non-leukemic and non-ovarian NCI-60 subsets based on MTS assay that involves silencing of ASNS and administering L-ASP to MCF7 and MDA-MB-231 (breast cancer), SNB-19 (glioblastoma), UACC-257 (melanoma), and SN12C (renal cancer) cell lines. Results are summarized in Table 15. The MTS assay reveals that combination with siASNS yielded large L-ASP potentiation: 3500-fold in the breast cancer MDA-MB-231, 10,000-fold in the breast cancer MCF7, 1000-fold in the glioblastoma SNB-19, 3100-fold in the melanoma UACC-257, and 1100-fold in the renal carcinoma SN12C, thereby demonstrating a causal link between ASNS expression and L-ASP activity in those tissue types. Higher doses of L-ASP can be employed. For example, a dose intermediate between the $EC50_{siNeg}$ and either of the $EC50_{siASNS}$ doses (Table 15) can be employed.

TABLE 15

STATISTICAL SUMMARY OF RNAi PHARMACOLOGY EXPERIMENTS
All $EC_{50}$ values are reported in units of U/mL

| Tissue: Cell Line | $EC50_{siNeg}$ | $EC50_{siASNS.1}$ (fold-potentiation) | $EC50_{siASNS.2}$ (fold-potentiation) |
|---|---|---|---|
| BR:MCF7 | $7.0 \cdot 10^{-1}$ | $6.8 \cdot 10^{-5}$ ($1.0 \cdot 10^4$) | $6.6 \cdot 10^{-5}$ ($1.1 \cdot 10^4$) |
| BR:MDA-MB-231 | $3.8 \cdot 10^{-1}$ | $1.1 \cdot 10^{-4}$ ($3.5 \cdot 10^3$) | $1.1 \cdot 10^{-4}$ ($3.5 \cdot 10^3$) |
| CNS:SNB-19 | $2.5 \cdot 10^{-1}$ | $2.6 \cdot 10^{-4}$ ($9.6 \cdot 10^2$) | $2.5 \cdot 10^{-4}$ ($1.0 \cdot 10^3$) |
| ME:UACC-257 | $2.5 \cdot 10^{-1}$ | $8.1 \cdot 10^{-5}$ ($3.1 \cdot 10^3$) | $8.1 \cdot 10^{-5}$ ($3.1 \cdot 10^3$) |
| RE:SN12C | $3.7 \cdot 10^{-1}$ | $2.9 \cdot 10^{-4}$ ($1.3 \cdot 10^3$) | $3.6 \cdot 10^{-4}$ ($1.0 \cdot 10^3$) |

Example 12

This example demonstrates, when viewed in the context of the above examples, that the ability of siRNA treatment to potentiate L-ASP activity is not necessarily dependent on baseline expression level of ASNS mRNA. To determine the correlation of L-ASP activity with ASNS expression in various breast cancer, central nervous system (CNS), melanoma and renal cancer cell lines, ASNS transcript levels are measured using Affymetrix U133 array as described above in Example 1 and shown in Table 1B. The results are shown in Tables 16-19.

TABLE 16

| Breast Cancer Cell Line Name | L-ASP $GI_{50}$ ($\log_{10}$) | ASNS expression ($\log_2$) |
|---|---|---|
| BT-549 | −1.31 | 1.53 |
| T47D | −1.08 | −1.34 |
| MDA-MB-231 | −0.93 | 1.55 |
| HS-578T | −0.87 | 2.01 |
| MCF7 | −0.13 | 0.33 |
| Pearson's correlation: | | −0.10 |

TABLE 17

| CNS Cancer Cell Line Name | L-ASP GI$_{50}$ (log$_{10}$) | ASNS expression (log$_2$) |
|---|---|---|
| SF-268 | −0.41 | 1.07 |
| SF-295 | −0.03 | −0.41 |
| SF-539 | −0.25 | −0.35 |
| SNB-19 | −0.64 | −0.84 |
| SNB-75 | −0.82 | −0.18 |
| U251 | 0.03 | 0.15 |
| Pearson's correlation: | | 0.15 |

TABLE 18

| Melanoma Cell Line Name | L-ASP GI$_{50}$ (log$_{10}$) | ASNS expression (log$_2$) |
|---|---|---|
| MALME-3M | −1.23 | −2.16 |
| MDA-MB-435 | −0.96 | −0.12 |
| MDA-N | −0.88 | 0.28 |
| SK-MEL-5 | −0.82 | 2.15 |
| M14 | −0.79 | −0.84 |
| UACC-257 | −0.54 | −3.06 |
| UACC-62 | −0.52 | 0.18 |
| LOX_IMVI | −0.06 | −0.11 |
| SK-MEL-2 | −0.05 | −0.93 |
| SK-MEL-28 | 0.06 | −2.39 |
| Pearson's correlation: | | −0.19 |

TABLE 19

| Renal Cancer Cell Line Name | L-ASP GI$_{50}$ (log$_{10}$) | ASNS expression (log$_2$) |
|---|---|---|
| UO-31 | −0.70 | −2.16 |
| TK-10 | −0.68 | 0.04 |
| ACHN | −0.58 | 0.16 |
| 786-0 | −0.17 | −1.65 |
| CAKI-1 | 0.02 | −0.18 |
| RXF-393 | 0.04 | −0.06 |
| A498 | 0.29 | 1.12 |
| SN12C | 0.42 | −1.72 |
| Pearson's correlation: | | −0.05 |

Although L-ASP treatment induces ASNS protein in each of the cell lines tested, none of those tissue types exhibit a strong correlation between L-ASP activity and ASNS expression as measured with Affymetrix U133 microarrays. The Pearson's correlations are −0.10 in breast, 0.15 in CNS, −0.19 in melanoma, and −0.05 in renal subsets of the NCI-60. However, when exemplary cell lines are treated with L-ASP in combination with siRNA as described in Examples 9-11 above, siRNA is able to effectively reduce ASNS expression. Accordingly, the ability of siRNA treatment to potentiate L-ASP activity is not dependent on baseline expression level of ASNS mRNA.

Example 13

This example demonstrates that the rapid increase in ASNS expression following L-ASP administration is suppressed by co-treatment with ASNS mRNA-targeted siRNA. The time course of ASNS expression following L-ASP administration is determined in siNeg- and siASNS.1-treated OVCAR-4 and OVCAR-8 cells. siNeg and siASNS.1 used are described in Example 2. ASNS mRNA levels are assayed consistent with the description in Example 2. The administered L-ASP dose can be a previously EC$_{50}$ value determined in Example 4 (Table 4)—1.31 U/mL for siASNS-treated OVCAR-4 cells, 6.35 U/mL for siNeg-treated OVCAR-4 cells, 0.0007 U/mL for siASNS-treated OVCAR-8 cells, and 0.45 U/mL for siNeg-treated OVCAR-8 cells. Transfections mediated by cationic lipid are performed in 96 well plates as described above. Cells are seeded on a complex of the appropriate siRNA (Qiagen Inc., Germantown, Md.) and Oligofectamine (Invitrogen, Carlsbad, Calif.) in unsupplemented RPMI-1640. Final amounts in each well are 50 nM siRNA, 0.475 µL Oligofectamine, and 5,000 OVCAR-4 cells in 100 µL of medium; 5 nM siRNA, 0.75 µL Oligofectamine, and 2,750 OVCAR-8 cells in 100 µL medium. Three replicate wells are used in mRNA determinations.

The time course of ASNS mRNA expression upregulation following administration of L-ASP is shown in FIG. 10. ASNS level for a given sample (n=2) are normalized to PPIB level of that sample. An EC$_{50}$ dose of L-ASP is administered to OVCAR-4 (squares) or OVCAR-8 (circles) cells transfected with either siNeg (shaded) or siASNS.1 (open), and the resulting ASNS mRNA is measured at indicated time points by branched-DNA assay. ASNS transcript is rapidly and extensively induced in both siNeg-transfected cell lines, whereas siASNS prevents ASNS upregulation.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A kit comprising (a) at least one probe for detecting a level of expression of an endogenous asparagine synthetase (ASNS) gene protein product in a sample from a human subject and (b) at least one standard comprising at least one human cell expressing a level of an ASNS protein, wherein the level of expression in the sample is associated with an efficacy of L-asparaginase (L-ASP) in decreasing cell proliferation and the efficacy is identified based on comparison of the level of expression detected by the probe in the sample to the level of expression detected by the probe in the standard, wherein a higher level of expression in the sample compared to the standard indicates a lower efficacy of L-ASP in decreasing cell proliferation in the sample compared to the standard and wherein a lower level of expression in the sample compared to the standard indicates a higher efficacy of L-ASP in decreasing cell proliferation in the sample compared to the standard, wherein the probe is a non-human antibody or an antigen binding fragment thereof that specifically binds to an epitope of an ASNS protein.

2. The kit of claim 1, wherein the epitope comprises SEQ ID NO: 16.

3. The kit of claim 1, wherein the antibody or fragment thereof further comprises a detectable label.

4. The kit of claim 3, wherein the label is selected from the group consisting of a radiolabel, a fluorescent label, an epitope recognizable by a secondary antibody, and any combination thereof.

5. The kit of claim 1, wherein the kit further comprises a secondary antibody or antigen binding fragment thereof that specifically binds the probe antibody or antigen binding fragment thereof.

6. The kit of claim 1, wherein the antibody or antigen binding fragment thereof is humanized.

7. The kit of claim 1, wherein the kit further comprises an ASNS antagonist, wherein the ASNS antagonist is siRNA.

8. The kit of claim 7, wherein the siRNA targets a nucleotide sequence of SEQ ID NO 7, SEQ ID NO 8, or a full complement thereof.

9. The kit of claim 7, wherein the siRNA is siASNS.1 or siASNS.2.

10. A kit comprising (a) at least one probe for detecting a level of expression of an endogenous asparagine synthetase (ASNS) gene protein product in a sample from a human subject, (b) at least one standard comprising at least one human cell expressing a level of an ASNS protein, wherein the level of expression in the sample is associated with an efficacy of L-asparaginase (L-ASP) in decreasing cell proliferation and the efficacy is identified based on comparison of the level of expression detected by the probe in the sample to the level of expression detected by the probe in the standard, wherein a higher level of expression in the sample compared to the standard indicates a lower efficacy of L-ASP in decreasing cell proliferation in the sample compared to the standard and wherein a lower level of expression in the sample compared to the standard indicates a higher efficacy of L-ASP in decreasing cell proliferation in the sample compared to the standard, wherein the probe is a non-human antibody or an antigen binding fragment thereof that specifically binds to an epitope of an ASNS protein, and (c) at least one L-ASP.

11. The kit of claim 10, wherein the at least one L-ASP is pegylated.

12. The kit of claim 10, wherein the epitope comprises SEQ ID NO: 16.

13. The kit of claim 10, wherein the antibody or antigen binding fragment thereof is humanized.

* * * * *

SEQUENCE LISTING

<160> NUMBER OF SEQ ID NOS: 16

<210> SEQ ID NO 1
<211> LENGTH: 1994
<212> TYPE: DNA
<213> ORGANISM: Homo sapiens

<400> SEQUENCE: 1

```
aaacttcccg cacgcgttac aggagccagg tcggtataag cgccagcggc ctcgccgccc      60
gtcaagctgt ccacatccct ggcctcagcc cgccacatca ccctgacctg cttacgccca     120
gattttcttc aatcacatct gaataaatca cttgaagaaa gcttatagct tcattgcacc     180
atgtgtggca tttgggcgct gtttggcagt gatgattgcc tttctgttca gtgtctgagt     240
gctatgaaga ttgcacacag aggtccagat gcattccgtt ttgagaatgt caatggatac     300
accaactgct gctttggatt tcaccggttg gcggtagttg acccgctgtt tggaatgcag     360
ccaattcgag tgaagaaata tccgtatttg tggctctgtt acaatggtga aatctacaac     420
cataagaaga tgcaacagca ttttgaattt gaataccaga ccaaagtgga tggtgagata     480
atccttcatc tttatgacaa aggaggaatt gagcaaacaa tttgtatgtt ggatggtgtg     540
tttgcatttg ttttactgga tactgccaat aagaaagtgt cctgggtag  agatacatat     600
ggagtcagac ctttgtttaa agcaatgaca gaagatggat tttggctgt  atgttcagaa     660
gctaaaggtc ttgttacatt gaagcactcc gcgactccct ttttaaaagt ggagcctttt     720
cttcctggac actatgaagt tttggattta agcccaaatg gcaaagttgc atccgtggaa     780
atggttaaat atcatcactg tcgggatgaa cccctgcacg ccctctatga caatgtggag     840
aaactctttc caggttttga gatagaaact gtgaagaaca acctcaggat ccttttttaat     900
aatgctgtaa agaaacgttt gatgacagac agaaggattg gctgcctttt atcaggggc     960
ttggactcca gcttggttgc tgccactctg ttgaagcagc tgaaagaagc ccaagtacag    1020
tatcctctcc agacatttgc aattggcatg gaagacagcc ccgatttact ggctgctaga    1080
aaggtggcag atcatattgg aagtgaacat tatgaagtcc ttttta actc tgaggaaggc    1140
attcaggctc tggatgaagt catattttcc ttggaaactt atgacattac aacagttcgt    1200
gcttcagtag gtatgtattt aatttccaag tatattcgga gaacacaga  tagcgtggtg    1260
atcttctctg gagaaggatc agatgaactt acgcagggtt acatatattt tcacaaggct    1320
ccttctcctg aaaaagccga ggaggagagt gagaggcttc tgagggaact ctatttgttt    1380
gatgttctcc gcgcagatcg aactactgct gcccatggtc ttgaactgag agtcccattt    1440
ctagatcatc gattttcttc ctattacttg tctctgccac cagaaatgag aattccaaag    1500
aatgggatag aaaaacatct cctgagagag acgtttgagg attccaatct gatacccaaa    1560
gagattctct ggcgaccaaa agaagccttc agtgatggaa taacttcagt taagaattcc    1620
tggtttaaga ttttacagga atacgttgaa catcaggttg atgatgcaat gatggcaaat    1680
gcagcccaga aatttccctt caatactcct aaaaccaaag aaggatatta ctaccgtcaa    1740
gtctttgaac gccattaccc aggccgggct gactggctga gccattactg gatgcccaag    1800
tggatcaatg ccactgaccc ttctgcccgc acgctgaccc actacaagtc agctgtcaaa    1860
gcttaggtgg tctttatgct gtaatgtgaa agcaaatatt tcttcgtgtt ggatggggac    1920
tgtgggtaga taggggaaca atgagagtca actcaggcta acttgggtgt gaaaaaaata    1980
aaagtcctaa atct                                                       1994
```

```
-continued

<210> SEQ ID NO 2
<211> LENGTH: 561
<212> TYPE: PRT
<213> ORGANISM: Homo sapiens

<400> SEQUENCE: 2

Met Cys Gly Ile Trp Ala Leu Phe Gly Ser Asp Asp Cys Leu Ser Val
1               5                   10                  15

Gln Cys Leu Ser Ala Met Lys Ile Ala His Arg Gly Pro Asp Ala Phe
            20                  25                  30

Arg Phe Glu Asn Val Asn Gly Tyr Thr Asn Cys Cys Phe Gly Phe His
        35                  40                  45

Arg Leu Ala Val Val Asp Pro Leu Phe Gly Met Gln Pro Ile Arg Val
    50                  55                  60

Lys Lys Tyr Pro Tyr Leu Trp Leu Cys Tyr Asn Gly Glu Ile Tyr Asn
65                  70                  75                  80

His Lys Lys Met Gln Gln His Phe Glu Phe Glu Tyr Gln Thr Lys Val
                85                  90                  95

Asp Gly Glu Ile Ile Leu His Leu Tyr Asp Lys Gly Gly Ile Glu Gln
            100                 105                 110

Thr Ile Cys Met Leu Asp Gly Val Phe Ala Phe Val Leu Leu Asp Thr
        115                 120                 125

Ala Asn Lys Lys Val Phe Leu Gly Arg Asp Thr Tyr Gly Val Arg Pro
    130                 135                 140

Leu Phe Lys Ala Met Thr Glu Asp Gly Phe Leu Ala Val Cys Ser Glu
145                 150                 155                 160

Ala Lys Gly Leu Val Thr Leu Lys His Ser Ala Thr Pro Phe Leu Lys
                165                 170                 175

Val Glu Pro Phe Leu Pro Gly His Tyr Glu Val Leu Asp Leu Lys Pro
            180                 185                 190

Asn Gly Lys Val Ala Ser Val Glu Met Val Lys Tyr His His Cys Arg
        195                 200                 205

Asp Glu Pro Leu His Ala Leu Tyr Asp Asn Val Glu Lys Leu Phe Pro
    210                 215                 220

Gly Phe Glu Ile Glu Thr Val Lys Asn Asn Leu Arg Ile Leu Phe Asn
225                 230                 235                 240

Asn Ala Val Lys Lys Arg Leu Met Thr Asp Arg Arg Ile Gly Cys Leu
                245                 250                 255

Leu Ser Gly Gly Leu Asp Ser Ser Leu Val Ala Ala Thr Leu Leu Lys
            260                 265                 270

Gln Leu Lys Glu Ala Gln Val Gln Tyr Pro Leu Gln Thr Phe Ala Ile
        275                 280                 285

Gly Met Glu Asp Ser Pro Asp Leu Leu Ala Ala Arg Lys Val Ala Asp
    290                 295                 300

His Ile Gly Ser Glu His Tyr Glu Val Leu Phe Asn Ser Glu Glu Gly
305                 310                 315                 320

Ile Gln Ala Leu Asp Glu Val Ile Phe Ser Leu Glu Thr Tyr Asp Ile
                325                 330                 335

Thr Thr Val Arg Ala Ser Val Gly Met Tyr Leu Ile Ser Lys Tyr Ile
            340                 345                 350

Arg Lys Asn Thr Asp Ser Val Val Ile Phe Ser Gly Glu Gly Ser Asp
        355                 360                 365

Glu Leu Thr Gln Gly Tyr Ile Tyr Phe His Lys Ala Pro Ser Pro Glu
    370                 375                 380
```

-continued

```
Lys Ala Glu Glu Ser Glu Arg Leu Leu Arg Glu Leu Tyr Leu Phe
385                 390                 395                 400

Asp Val Leu Arg Ala Asp Arg Thr Thr Ala Ala His Gly Leu Glu Leu
            405                 410                 415

Arg Val Pro Phe Leu Asp His Arg Phe Ser Ser Tyr Tyr Leu Ser Leu
        420                 425                 430

Pro Pro Glu Met Arg Ile Pro Lys Asn Gly Ile Glu Lys His Leu Leu
    435                 440                 445

Arg Glu Thr Phe Glu Asp Ser Asn Leu Ile Pro Lys Glu Ile Leu Trp
450                 455                 460

Arg Pro Lys Glu Ala Phe Ser Asp Gly Ile Thr Ser Val Lys Asn Ser
465                 470                 475                 480

Trp Phe Lys Ile Leu Gln Glu Tyr Val Glu His Gln Val Asp Asp Ala
            485                 490                 495

Met Met Ala Asn Ala Ala Gln Lys Phe Pro Phe Asn Thr Pro Lys Thr
        500                 505                 510

Lys Glu Gly Tyr Tyr Tyr Arg Gln Val Phe Glu Arg His Tyr Pro Gly
    515                 520                 525

Arg Ala Asp Trp Leu Ser His Tyr Trp Met Pro Lys Trp Ile Asn Ala
    530                 535                 540

Thr Asp Pro Ser Ala Arg Thr Leu Thr His Tyr Lys Ser Ala Val Lys
545                 550                 555                 560

Ala
```

```
<210> SEQ ID NO 3
<211> LENGTH: 2348
<212> TYPE: DNA
<213> ORGANISM: Homo sapiens

<400> SEQUENCE: 3
cctttctgtc ctggttccct gaagcatcga gagggaaccg cggccggcag gccggaccgc      60
tccggagagg aggcagcggc agtttgagcc cctgtaaatg ttatatgtgt acttttttt     120 actatgtggc gtcgaagcct gtggacattt tcgcggtccg ggtccctgcg gcggacgggt     180
cggatcgtgc tcgtggccag ggcgcagtca ggtgtcgcgt ggtcctgatc taggaagaga     240
ctgcggcctt atcaccgtct cggtgtctgc tttcaccttc aactgccccc ctcctcacct     300
ggaccgctca ccctcctcct cccctctcac cccgccatcc ccaccagtcc ccacctgtct     360
ctgtagactg caagactcat caagtgactt gctgagcaaa ccctgccgag aagagatttt     420
cttcaatcac atctgaataa atcacttgaa gaaagcttat agcttcattg caccatgtgt     480
ggcatttggg cgctgtttgg cagtgatgat tgcctttctg ttcagtgtct gagtgctatg     540
aagattgcac acagaggtcc agatgcattc cgttttgaga atgtcaatgg atacaccaac     600
tgctgctttg gatttcaccg gttggcggta gttgacccgc tgtttggaat gcagccaatt     660
cgagtgaaga aatatccgta tttgtggctc tgttacaatg gtgaaatcta caaccataag     720
aagatgcaac agcattttga atttgaatac agaccaaagt ggatggtgat aatccttt     780 catctttatg acaaggagg aattgagcaa acaatttgta tgttggatgg tgtgtttgca     840 tttgtttac tggatactgc caataagaaa gtgttcctgg gtagagatac atatggagtc     900
agacctttgt ttaaagcaat gacagaagat ggattttgg ctgtatgttc agaagctaaa     960
ggtcttgtta cattgaagca ctccgcgact cccttttaa aagtggagcc ttttcttcct    1020
ggacactatg aagttttgga tttaaagcca atggcaaag ttgcatccgt ggaaatggtt    1080
```

```
aaatatcatc actgtcggga tgaacccctg cacgccctct atgacaatgt ggagaaactc    1140
tttccaggtt ttgagataga aactgtgaag aacaacctca ggatcctttt taataatgct    1200
gtaaagaaac gtttgatgac agacagaagg attggctgcc ttttatcagg gggcttggac    1260
tccagcttgg ttgctgccac tctgttgaag cagctgaaag aagcccaagt acagtatcct    1320
ctccagacat ttgcaattgg catggaagac agccccgatt tactggctgc tagaaaggtg    1380
gcagatcata ttggaagtga acattatgaa gtccttttta actctgagga aggcattcag    1440
gctctggatg aagtcatatt ttccttggaa acttatgaca ttacaacagt tcgtgcttca    1500
gtaggtatgt atttaatttc caagtatatt cggaagaaca cagatagcgt ggtgatcttc    1560
tctggagaag gatcagatga acttacgcag ggttacatat attttcacaa ggctccttct    1620
cctgaaaaag ccgaggagga gagtgagagg cttctgaggg aactctattt gtttgatgtt    1680
ctccgcgcag atcgaactac tgctgcccat ggtcttgaac tgagagtccc atttctagat    1740
catcgatttt cttcctatta cttgtctctg ccaccagaaa tgagaattcc aaagaatggg    1800
atagaaaaac atcctgag agagacgttt gaggattcca atctgatacc aaagagatt     1860 ctctggcgac aaaagaagc cttcagtgat ggaataactt cagttaagaa ttcctggttt    1920
aagattttac aggaatacgt tgaacatcag gttgatgatg caatgatggc aaatgcagcc    1980
cagaaatttc ccttcaatac tcctaaaacc aagaaggat attactaccg tcaagtcttt    2040
gaacgccatt acccaggccg ggctgactgg ctgagccatt actggatgcc aagtggatc     2100 aatgccactg acccttctgc ccgcacgctg acccactaca agtcagctgt caaagcttag    2160
gtggtcttta tgctgtaatg tgaaagcaaa tatttcttcg tgttggatgg ggactgtggg    2220
tagatagggg aacaatgaga gtcaactcag gctaacttgg gtgtgaaaaa aataaaagtc    2280
ctaaatctaa aaaaaaaaaa aaaaaaaaaa aaaaaaaaaa aaaaaaaaaa aaaaaaaaaa    2340
aaaaaaaa                                                            2348
```

<210> SEQ ID NO 4
<211> LENGTH: 561
<212> TYPE: PRT
<213> ORGANISM: Homo sapiens

<400> SEQUENCE: 4

```
Met Cys Gly Ile Trp Ala Leu Phe Gly Ser Asp Asp Cys Leu Ser Val
1               5                   10                  15

Gln Cys Leu Ser Ala Met Lys Ile Ala His Arg Gly Pro Asp Ala Phe
            20                  25                  30

Arg Phe Glu Asn Val Asn Gly Tyr Thr Asn Cys Cys Phe Gly Phe His
        35                  40                  45

Arg Leu Ala Val Val Asp Pro Leu Phe Gly Met Gln Pro Ile Arg Val
    50                  55                  60

Lys Lys Tyr Pro Tyr Leu Trp Leu Cys Tyr Asn Gly Glu Ile Tyr Asn
65                  70                  75                  80

His Lys Lys Met Gln Gln His Phe Glu Phe Glu Tyr Gln Thr Lys Val
                85                  90                  95

Asp Gly Glu Ile Ile Leu His Leu Tyr Asp Lys Gly Gly Ile Glu Gln
            100                 105                 110

Thr Ile Cys Met Leu Asp Gly Val Phe Ala Phe Val Leu Leu Asp Thr
        115                 120                 125

Ala Asn Lys Lys Val Phe Leu Gly Arg Asp Thr Tyr Gly Val Arg Pro
    130                 135                 140
```

-continued

```
Leu Phe Lys Ala Met Thr Glu Asp Gly Phe Leu Ala Val Cys Ser Glu
145                 150                 155                 160

Ala Lys Gly Leu Val Thr Leu Lys His Ser Ala Thr Pro Phe Leu Lys
            165                 170                 175

Val Glu Pro Phe Leu Pro Gly His Tyr Glu Val Leu Asp Leu Lys Pro
        180                 185                 190

Asn Gly Lys Val Ala Ser Val Glu Met Val Lys Tyr His His Cys Arg
    195                 200                 205

Asp Glu Pro Leu His Ala Leu Tyr Asp Asn Val Glu Lys Leu Phe Pro
210                 215                 220

Gly Phe Glu Ile Glu Thr Val Lys Asn Leu Arg Ile Leu Phe Asn
225                 230                 235                 240

Asn Ala Val Lys Lys Arg Leu Met Thr Asp Arg Ile Gly Cys Leu
            245                 250                 255

Leu Ser Gly Gly Leu Asp Ser Ser Leu Val Ala Ala Thr Leu Leu Lys
            260                 265                 270

Gln Leu Lys Glu Ala Gln Val Gln Tyr Pro Leu Gln Thr Phe Ala Ile
        275                 280                 285

Gly Met Glu Asp Ser Pro Asp Leu Leu Ala Ala Arg Lys Val Ala Asp
290                 295                 300

His Ile Gly Ser Glu His Tyr Glu Val Leu Phe Asn Ser Glu Glu Gly
305                 310                 315                 320

Ile Gln Ala Leu Asp Glu Val Ile Phe Ser Leu Glu Thr Tyr Asp Ile
                325                 330                 335

Thr Thr Val Arg Ala Ser Val Gly Met Tyr Leu Ile Ser Lys Tyr Ile
            340                 345                 350

Arg Lys Asn Thr Asp Ser Val Val Ile Phe Ser Gly Glu Gly Ser Asp
            355                 360                 365

Glu Leu Thr Gln Gly Tyr Ile Tyr Phe His Lys Ala Pro Ser Pro Glu
370                 375                 380

Lys Ala Glu Glu Glu Ser Glu Arg Leu Leu Arg Glu Leu Tyr Leu Phe
385                 390                 395                 400

Asp Val Leu Arg Ala Asp Arg Thr Thr Ala Ala His Gly Leu Glu Leu
                405                 410                 415

Arg Val Pro Phe Leu Asp His Arg Phe Ser Ser Tyr Tyr Leu Ser Leu
            420                 425                 430

Pro Pro Glu Met Arg Ile Pro Lys Asn Gly Ile Glu Lys His Leu Leu
        435                 440                 445

Arg Glu Thr Phe Glu Asp Ser Asn Leu Ile Pro Lys Glu Ile Leu Trp
450                 455                 460

Arg Pro Lys Glu Ala Phe Ser Asp Gly Ile Thr Ser Val Lys Asn Ser
465                 470                 475                 480

Trp Phe Lys Ile Leu Gln Glu Tyr Val Glu His Gln Val Asp Asp Ala
            485                 490                 495

Met Met Ala Asn Ala Ala Gln Lys Phe Pro Phe Asn Thr Pro Lys Thr
            500                 505                 510

Lys Glu Gly Tyr Tyr Tyr Arg Gln Val Phe Glu Arg His Tyr Pro Gly
        515                 520                 525

Arg Ala Asp Trp Leu Ser His Tyr Trp Met Pro Lys Trp Ile Asn Ala
            530                 535                 540

Thr Asp Pro Ser Ala Arg Thr Leu Thr His Tyr Lys Ser Ala Val Lys
545                 550                 555                 560

Ala
```

<210> SEQ ID NO 5
<211> LENGTH: 2345
<212> TYPE: DNA
<213> ORGANISM: Homo sapiens

<400> SEQUENCE: 5

```
cgcaggcatg atgaaacttc ccgcacgcgt tacaggagcc aggtcggtat aagcgccagc      60
ggcctcgccg cccgtcaagc tgtccacatc cctggcctca gcccgccaca tcaccctgac     120
ctgcttacgc ccagcctgtg acattttcg cggtccgggt ccctgcggcg acgggtcgg      180
atcgtgctcg tggccagggc gcagtcaggt gtcgcgtggt cctgatctag aagagactg      240
cggccttatc accgtctcgg tgtctgcttt caccttcaac tgccccctc ctcacctgga      300
ccgctcaccc tcctcctccc ctctcacccc gccatcccca ccagtccca cctgtctctg     360
tagactgcaa gactcatcaa gtgacttgct gagcaaaccc tgccgagaag atttttctt     420
caatcacatc tgaataaatc acttgaagaa agcttatagc ttcattgcac catgtgtggc     480
atttgggcgc tgtttggcag tgatgattgc ctttctgttc agtgtctgag tgctatgaag     540
attgcacaca gaggtccaga tgcattccgt tttgagaatg tcaatggata caccaactgc     600
tgctttggat tcaccggtt ggcggtagtt gacccgctgt ttggaatgca gccaattcga     660
gtgaagaaat atccgtattt gtggctctgt tacaatggtg aaatctacaa ccataagaag     720
atgcaacagc attttgaatt tgaataccag accaaagtgg atggtgagat aatccttcat     780
ctttatgaca aggaggaat tgagcaaaca atttgtatgt tggatggtgt gtttgcattt     840
gttttactgg atactgccaa taagaaagtg ttcctgggta gagatacata tggagtcaga     900
cctttgttta aagcaatgac agaagatgga ttttggctg tatgttcaga agctaaaggt     960
cttgttacat tgaagcactc cgcgactccc ttttaaaag tggagccttt tcttcctgga    1020
cactatgaag ttttggattt aaagccaaat ggcaaagttg catccgtgga atggttaaa    1080
tatcatcact gtcgggatga acccctgcac gccctctatg acaatgtgga gaaactcttt    1140
ccaggttttg atagaaaac tgtgaagaac aacctcagga tccttttaa taatgctgta    1200
aagaaacgtt tgatgacaga cagaaggatt ggctgccttt tatcagggg cttggactcc    1260
agcttggttg ctgccactct gttgaagcag ctgaaagaag cccaagtaca gtatcctctc    1320
cagacatttg caattggcat ggaagacagc cccgatttac tggctgctag aaaggtggca    1380
gatcatattg gaagtgaaca ttatgaagtc ctttttaact ctgaggaagg cattcaggct    1440
ctggatgaag tcatattttc cttggaaact tatgacatta caacagttcg tgcttcagta    1500
ggtatgtatt taatttccaa gtatattcgg aagaacacag atagcgtggt gatcttctct    1560
ggagaaggat cagatgaact tacgcagggt tacatatatt ttcacaaggc tccttctcct    1620
gaaaaagccg aggaggagag tgagaggctt ctgagggaac tctatttgtt tgatgttctc    1680
cgcgcagatc gaactactgc tgcccatggt cttgaactga gagtcccatt tctagatcat    1740
cgattttctt cctattactt gtctctgcca ccagaaatga aattccaaa gaatgggata    1800
gaaaaacatc tcctgagaga gacgtttgag gattccaatc tgatacccaa agagattctc    1860
tggcgaccaa aagaagcctt cagtgatgga ataacttcag ttaagaattc ctggtttaag    1920
attttacagg aatacgttga acatcaggtt gatgatgcaa tgatggcaaa tgcagcccag    1980
aaatttccct tcaatactcc taaaaccaaa gaaggatatt actaccgtca agtctttgaa    2040
cgccattacc caggccgggc tgactggctg agccattact ggatgccaa gtggatcaat    2100
```

-continued

```
gccactgacc cttctgcccg cacgctgacc cactacaagt cagctgtcaa agcttaggtg    2160
gtctttatgc tgtaatgtga aagcaaatat ttcttcgtgt tggatgggga ctgtgggtag    2220
ataggggaac aatgagagtc aactcaggct aacttgggtg tgaaaaaaat aaaagtccta    2280
aatctaaaaa aaaaaaaaa aaaaaaaaa aaaaaaaaa aaaaaaaaa aaaaaaaaaa       2340 aaaaa                                                               2345

<210> SEQ ID NO 6
<211> LENGTH: 561
<212> TYPE: PRT
<213> ORGANISM: Homo sapiens

<400> SEQUENCE: 6

Met Cys Gly Ile Trp Ala Leu Phe Gly Ser Asp Asp Cys Leu Ser Val
1               5                   10                  15

Gln Cys Leu Ser Ala Met Lys Ile Ala His Arg Gly Pro Asp Ala Phe
            20                  25                  30

Arg Phe Glu Asn Val Asn Gly Tyr Thr Asn Cys Cys Phe Gly Phe His
        35                  40                  45

Arg Leu Ala Val Val Asp Pro Leu Phe Gly Met Gln Pro Ile Arg Val
    50                  55                  60

Lys Lys Tyr Pro Tyr Leu Trp Leu Cys Tyr Asn Gly Glu Ile Tyr Asn
65                  70                  75                  80

His Lys Lys Met Gln Gln His Phe Glu Phe Glu Tyr Gln Thr Lys Val
                85                  90                  95

Asp Gly Glu Ile Ile Leu His Leu Tyr Asp Lys Gly Gly Ile Glu Gln
            100                 105                 110

Thr Ile Cys Met Leu Asp Gly Val Phe Ala Phe Val Leu Leu Asp Thr
        115                 120                 125

Ala Asn Lys Lys Val Phe Leu Gly Arg Asp Thr Tyr Gly Val Arg Pro
    130                 135                 140

Leu Phe Lys Ala Met Thr Glu Asp Gly Phe Leu Ala Val Cys Ser Glu
145                 150                 155                 160

Ala Lys Gly Leu Val Thr Leu Lys His Ser Ala Thr Pro Phe Leu Lys
                165                 170                 175

Val Glu Pro Phe Leu Pro Gly His Tyr Glu Val Leu Asp Leu Lys Pro
            180                 185                 190

Asn Gly Lys Val Ala Ser Val Glu Met Val Lys Tyr His Cys Arg
                195                 200                 205

Asp Glu Pro Leu His Ala Leu Tyr Asp Asn Val Glu Lys Leu Phe Pro
    210                 215                 220

Gly Phe Glu Ile Glu Thr Val Lys Asn Asn Leu Arg Ile Leu Phe Asn
225                 230                 235                 240

Asn Ala Val Lys Lys Arg Leu Met Thr Asp Arg Ile Gly Cys Leu
                245                 250                 255

Leu Ser Gly Gly Leu Asp Ser Ser Leu Val Ala Ala Thr Leu Leu Lys
            260                 265                 270

Gln Leu Lys Glu Ala Gln Val Gln Tyr Pro Leu Gln Thr Phe Ala Ile
        275                 280                 285

Gly Met Glu Asp Ser Pro Asp Leu Leu Ala Ala Arg Lys Val Ala Asp
    290                 295                 300

His Ile Gly Ser Glu His Tyr Glu Val Leu Phe Asn Ser Glu Glu Gly
305                 310                 315                 320

Ile Gln Ala Leu Asp Glu Val Ile Phe Ser Leu Glu Thr Tyr Asp Ile
```

```
                    325                 330                 335
Thr Thr Val Arg Ala Ser Val Gly Met Tyr Leu Ile Ser Lys Tyr Ile
                340                 345                 350
Arg Lys Asn Thr Asp Ser Val Val Ile Phe Ser Gly Glu Gly Ser Asp
            355                 360                 365
Glu Leu Thr Gln Gly Tyr Ile Tyr Phe His Lys Ala Pro Ser Pro Glu
        370                 375                 380
Lys Ala Glu Glu Ser Glu Arg Leu Leu Arg Glu Leu Tyr Leu Phe
385                 390                 395                 400
Asp Val Leu Arg Ala Asp Arg Thr Thr Ala Ala His Gly Leu Glu Leu
                405                 410                 415
Arg Val Pro Phe Leu Asp His Arg Phe Ser Ser Tyr Tyr Leu Ser Leu
                420                 425                 430
Pro Pro Glu Met Arg Ile Pro Lys Asn Gly Ile Glu Lys His Leu Leu
            435                 440                 445
Arg Glu Thr Phe Glu Asp Ser Asn Leu Ile Pro Lys Glu Ile Leu Trp
        450                 455                 460
Arg Pro Lys Glu Ala Phe Ser Asp Gly Ile Thr Ser Val Lys Asn Ser
465                 470                 475                 480
Trp Phe Lys Ile Leu Gln Glu Tyr Val Glu His Gln Val Asp Asp Ala
                485                 490                 495
Met Met Ala Asn Ala Ala Gln Lys Phe Pro Phe Asn Thr Pro Lys Thr
            500                 505                 510
Lys Glu Gly Tyr Tyr Tyr Arg Gln Val Phe Glu Arg His Tyr Pro Gly
        515                 520                 525
Arg Ala Asp Trp Leu Ser His Tyr Trp Met Pro Lys Trp Ile Asn Ala
    530                 535                 540
Thr Asp Pro Ser Ala Arg Thr Leu Thr His Tyr Lys Ser Ala Val Lys
545                 550                 555                 560
Ala

<210> SEQ ID NO 7
<211> LENGTH: 21
<212> TYPE: DNA
<213> ORGANISM: Homo sapiens

<400> SEQUENCE: 7
ctggatactg ccaataagaa a                                           21

<210> SEQ ID NO 8
<211> LENGTH: 21
<212> TYPE: DNA
<213> ORGANISM: Homo sapiens

<400> SEQUENCE: 8
cagaagctaa aggtcttgtt a                                           21

<210> SEQ ID NO 9
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' terminal two nucleotides are
      deoxyribonucleic acids.

<400> SEQUENCE: 9
```
ggauacugcc aauaagaaat t                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' terminal two nucleotides are
      deoxyribonucleic acids.

<400> SEQUENCE: 10
uuucuuauug gcaguaucca g                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' terminal two nucleotides are
      deoxyribonucleic acids.

<400> SEQUENCE: 11
gaagcuaaag gucuuguuat t                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' terminal two nucleotides are
      deoxyribonucleic acids.

<400> SEQUENCE: 12
uaacaagacc uuuagcuuct g                                              21

<210> SEQ ID NO 13
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' terminal two nucleotides are
      deoxyribonucleic acids.

<400> SEQUENCE: 13
uucuccgaac gugucacgut t                                              21

<210> SEQ ID NO 14
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' terminal two nucleotides are
      deoxyribonucleic acids.

```
<400> SEQUENCE: 14
acgugacacg uucggagaat t                                              21

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
aattctcgaa cgtgtcacgt                                                20

<210> SEQ ID NO 16
<211> LENGTH: 4
<212> TYPE: PRT
<213> ORGANISM: Homo sapiens

<400> SEQUENCE: 16

Thr Asp Pro Ser
1
```